(12) United States Patent
Krueger

(10) Patent No.: US 10,231,614 B2
(45) Date of Patent: *Mar. 19, 2019

(54) SYSTEMS AND METHODS FOR USING VIRTUAL REALITY, AUGMENTED REALITY, AND/OR A SYNTHETIC 3-DIMENSIONAL INFORMATION FOR THE MEASUREMENT OF HUMAN OCULAR PERFORMANCE

(71) Applicant: Wesley W. O. Krueger, San Antonio, TX (US)

(72) Inventor: Wesley W. O. Krueger, San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/713,418

(22) Filed: Sep. 22, 2017

(65) Prior Publication Data

US 2018/0008141 A1    Jan. 11, 2018

Related U.S. Application Data

(63) Continuation-in-part of application No. 15/162,300, filed on May 23, 2016, now Pat. No. 9,788,714, (Continued)

(51) Int. Cl.
*A61B 3/14* (2006.01)
*A61B 3/00* (2006.01)
(Continued)

(52) U.S. Cl.
CPC .......... *A61B 3/0041* (2013.01); *A61B 3/0025* (2013.01); *A61B 3/032* (2013.01);
(Continued)

(58) Field of Classification Search
CPC ........... A61B 3/113; A61B 3/14; A61B 3/102; G06K 9/00604; G06F 3/013
(Continued)

(56) References Cited

U.S. PATENT DOCUMENTS 4,817,633 A    4/1989  McStravick et al.
5,180,907 A    1/1993  Udden et al.
(Continued)

FOREIGN PATENT DOCUMENTS

WO    WO 2013117727    8/2013

OTHER PUBLICATIONS

Allison et al. Combined Head and Eye Tracking System for Dynamic Testing of the Vestibular System. IEEE Transactions on Biometical Engineering, vol. 43 No. 11 Nov. 1996. (USA).

*Primary Examiner* — Mohammed A Hasan
(74) *Attorney, Agent, or Firm* — Kilpatrick Townsend & Stockton LLP

(57) ABSTRACT

A system or method for measuring human ocular performance can be implemented using an eye sensor, a head orientation sensor, an electronic circuit and a display that presents one of virtual reality information, augmented reality information, or synthetic computer-generated 3-dimensional information. The device is configured for measuring saccades, pursuit tracking during visual pursuit, nystagmus, vergence, eyelid closure, or focused position of the eyes. The eye sensor comprises a video camera that senses vertical movement and horizontal movement of at least one eye. The head orientation sensor senses pitch and yaw in the range of frequencies between 0.01 Hertz and 15 Hertz. The system uses a Fourier transform to generate a vertical gain signal and a horizontal gain signal.

20 Claims, 16 Drawing Sheets

Related U.S. Application Data which is a continuation-in-part of application No. 14/326,335, filed on Jul. 8, 2014, now Pat. No. 9,370,302.

(51) Int. Cl.

| | | |
|---|---|---|
| *A61B 3/113* | (2006.01) | |
| *A61B 5/11* | (2006.01) | |
| *A61B 5/00* | (2006.01) | |
| *A61B 3/18* | (2006.01) | |
| *A61B 3/032* | (2006.01) | |
| *G06F 3/01* | (2006.01) | |
| *G06T 19/00* | (2011.01) | |
| *G02B 27/01* | (2006.01) | |
| *A61B 5/16* | (2006.01) | |
| *G16H 50/30* | (2018.01) | |
| *A61B 3/11* | (2006.01) | |

(52) U.S. Cl.
CPC ............ *A61B 3/113* (2013.01); *A61B 3/14* (2013.01); *A61B 3/18* (2013.01); *A61B 5/0071* (2013.01); *A61B 5/11* (2013.01); *A61B 5/1121* (2013.01); *A61B 5/163* (2017.08); *A61B 5/4023* (2013.01); *A61B 5/4064* (2013.01); *A61B 5/4863* (2013.01); *A61B 5/6803* (2013.01); *A61B 5/6814* (2013.01); *A61B 5/7257* (2013.01); *A61B 5/744* (2013.01); *G02B 27/017* (2013.01); *G06F 3/012* (2013.01); *G06T 19/006* (2013.01); *G16H 50/30* (2018.01); *A61B 3/112* (2013.01); *A61B 5/0002* (2013.01); *A61B 2562/0219* (2013.01); *A61B 2562/0223* (2013.01); *G06F 3/013* (2013.01)

(58) Field of Classification Search
USPC .................................................. 351/209, 210
See application file for complete search history.

(56) References Cited

U.S. PATENT DOCUMENTS

| | | |
|---|---|---|
| 5,550,601 A | 8/1996 | Donaldson |
| 5,555,895 A | 9/1996 | Ulmer et al. |
| 5,838,420 A | 11/1998 | MacGregor Donaldson |
| 5,919,149 A | 7/1999 | Allum |
| 5,942,954 A | 8/1999 | Galiana et al. |
| 5,953,102 A | 9/1999 | Berry |
| 6,796,947 B2 | 9/2004 | Watt et al. |
| 7,380,938 B2 | 6/2008 | Chmielewski et al. |
| 7,401,920 B1 | 7/2008 | Kranz et al. |
| 7,448,751 B2 | 11/2008 | Kiderman et al. |
| 7,500,752 B2 | 3/2009 | Nashner |
| 7,651,224 B2 | 1/2010 | Wood et al. |
| 7,682,024 B2 | 3/2010 | Plant et al. |
| 7,727,162 B2 | 6/2010 | Peterka |
| 7,731,360 B2 | 6/2010 | MacDougall et al. |
| 7,753,523 B2 | 7/2010 | Kiderman et al. |
| 7,866,818 B2 | 1/2011 | Schroeder et al. |
| 7,931,370 B2 | 4/2011 | Bartomeu |
| 7,988,287 B1 | 8/2011 | Butler et al. |
| 8,253,814 B2 | 8/2012 | Zhang et al. |
| 8,285,416 B2 | 10/2012 | Cho et al. |
| 8,510,166 B2 | 8/2013 | Neven |
| 8,529,463 B2 | 9/2013 | Della Santina et al. |
| 8,696,126 B2 | 4/2014 | Yeo et al. |
| 8,764,193 B2 | 7/2014 | Kiderman et al. |
| 2002/0118339 A1 | 8/2002 | Lowe |
| 2006/0098087 A1 | 5/2006 | Brandt et al. |
| 2006/0206175 A1* | 9/2006 | Fernandez Tournier .................... A63B 26/003 607/88 |
| 2006/0270945 A1 | 11/2006 | Ghajar |
| 2009/0021695 A1 | 1/2009 | Scarpino |
| 2010/0036289 A1 | 2/2010 | White et al. |
| 2010/0092049 A1 | 4/2010 | Schroeder et al. |
| 2010/0198104 A1 | 8/2010 | Schubert et al. |
| 2010/0280372 A1 | 11/2010 | Poolman et al. |
| 2011/0176106 A1 | 7/2011 | Lewkowski |
| 2012/0133892 A1 | 5/2012 | Furman et al. |
| 2013/0278899 A1 | 10/2013 | Waldorf et al. |
| 2014/0111771 A1 | 4/2014 | Liu |
| 2014/0192326 A1 | 7/2014 | Kiderman et al. |
| 2014/0327880 A1 | 11/2014 | Kiderman et al. |
| 2015/0038803 A1 | 2/2015 | Uhlig et al. |
| 2015/0212576 A1 | 7/2015 | Ambrus et al. |
| 2015/0223683 A1 | 8/2015 | Davidovics et al. |
| 2015/0243099 A1 | 8/2015 | Schowengerdt |
| 2015/0245766 A1 | 9/2015 | Rennaker et al. |
| 2015/0335239 A1 | 11/2015 | Macfougall |
| 2016/0033750 A1 | 2/2016 | Nunnink et al. |
| 2016/0062459 A1 | 3/2016 | Publicover et al. |
| 2016/0081546 A1 | 3/2016 | MacDougall |
| 2016/0085302 A1 | 3/2016 | Publicover et al. |
| 2016/0106315 A1 | 4/2016 | Kempinski |
| 2016/0110920 A1 | 4/2016 | Schowengerdt |
| 2016/0132726 A1 | 5/2016 | Kempinski et al. |
| 2016/0242642 A1* | 8/2016 | Migliaccio ............ A61B 3/113 |

* cited by examiner

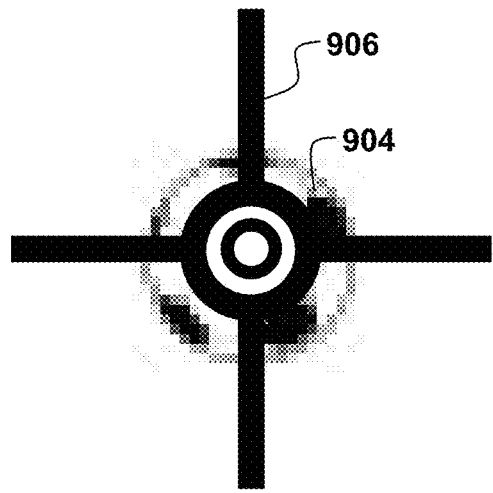
FIG. 11A  FIG. 11B
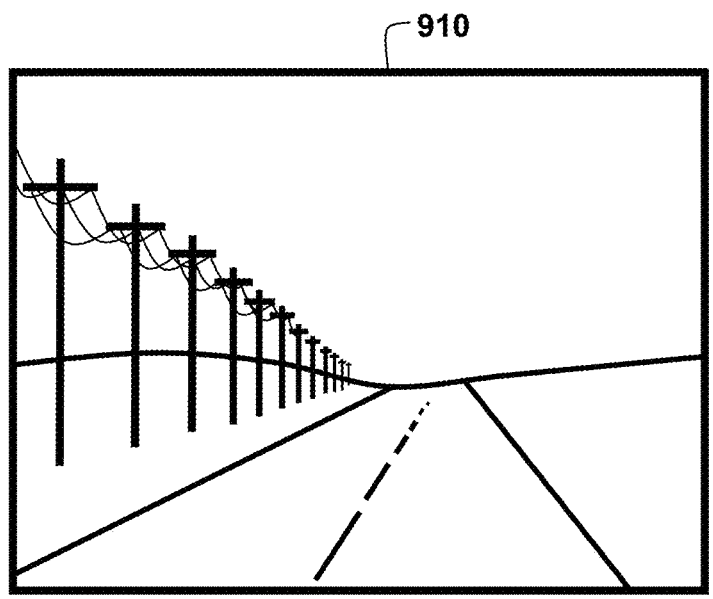
FIG. 12

SYSTEMS AND METHODS FOR USING VIRTUAL REALITY, AUGMENTED REALITY, AND/OR A SYNTHETIC 3-DIMENSIONAL INFORMATION FOR THE MEASUREMENT OF HUMAN OCULAR PERFORMANCE

CROSS REFERENCE TO RELATED APPLICATIONS

This is a Continuation-In-Part of U.S. patent application Ser. No. 15/162,300, filed 23 May 2016, which is a Continuation-In-Part of U.S. patent application Ser. No. 14/326,335, filed 8 Jul. 2014, now U.S. Pat. No. 9,370,302, issued 21 Jun. 2016, the entire disclosures of which are incorporated by reference herein for all purposes.

BACKGROUND

The present invention relates to systems and methods that use virtual reality, augmented reality, and/or a synthetic computer-generated 3-dimensional information (VR/AR/synthetic 3D) for the measurement of human ocular performance. Examples of human ocular performance measurements that can be measured using VR/AR/synthetic 3D include vestibulo-ocular reflex, saccades, visual pursuit tracking, nystagmus, vergence, eye-lid closure, dynamic visual acuity, kinetic visual acuity, retinal image stability, foveal fixation stability, and focused position of the eyes.

1. Definitions. The definitions that follow apply to the terminology used in describing the content and embodiments in this disclosure and the related claims.

Virtual reality (VR) can be defined as a computer-generated simulation of a three-dimensional image or environment that can be explored and interacted with by a user. The user becomes part of the virtual scene or immersed within the environment. While being part of the virtual environment, he or she can interact within a seemingly real or physical way, to use or manipulate objects or special electronic equipment. An example would be to perform a series of actions with a device or use a glove fitted with sensors or to wear a helmet with a projected virtual screen inside. Virtual reality environments can be implemented stereoscopically using an opaque display system, i.e. the user only sees the virtual scene and cannot see through the scene. The peripheral vision can be blocked to decrease any distraction from the user experience. Virtual reality can be used in simulators. Virtual display images or visual elements may be actively streamed from an attached computer, a wireless computer source, a smartphone, a smart display pad, or directly with digital camera systems and virtual camera systems. Virtual reality can also be created using holographic or volumetric three-dimensional displays.

Augmented reality (AR) can be defined broadly as the integration of digital information with the user's environment in real time. It refers to technology that incorporates real-time inputs from the existing world to create an output that combines both real-world data and some programmed, interactive elements that operate on those real-world inputs. Augmented reality will respond contextually to new external information and account for changes to users' environments, interpret gestures and actions in real time, with minimal to no explicit commands from users and will be presented in a way that does not restrict users' movements in their environment. It overlays information on an image being viewed through a device. Unlike virtual reality, which creates a totally artificial environment, augmented reality uses the existing environment and overlays new information on top of it.

A synthetic computer-generated 3-dimensional information (synthetic 3D) is a computer generated 3D model of visual information or images on a plane with X, Y and Z axes. A synthetic 3D model could be rotated and viewed from any angle. Synthetic objects don't need to exist in nature. These objects could be totally synthetic or partially synthetic. These objects or images can be realistic three-dimensional representations of the outside world. Synthetic 3D information can include integrated guidance symbologies. 3D synthetic information can be static and/or dynamic.

A display can be defined as a device that presents characters, images, or graphics representing data in a computer memory. Displays can present visual information in two dimensions or in three dimensions. In this document a three-dimensional display (3D display) is a display that conveys depth perception information to a user. 3D displays can be holograms, volumetric displays, or can use other technologies for presenting depth information in combination with the traditional two-dimensional information, such as stereoscopic displays. Examples of volumetric displays can include: multiplanar displays that have multiple display planes stacked up; and rotating panel displays where a rotating panel sweeps out a volume.

A stereoscopic display is a display system that presents offset 2D images separately to the left and right eye. Both of these 2D offset images are then combined in the brain to give the perception of 3-dimensional depth. Examples of stereoscopic display technologies and devices can include:

(a) Presenting a left eye image and a right eye image on separate screens in a head-worn unit.

(b) Presenting a left eye image and a right eye image on a single display and having the user wear glasses that separate the left-eye image and the right eye image. Examples of technologies that can be used for this image separation are color filters, polarizing filters, and time-dependent shutters that open for one eye when a left image is being presented on the display and open for the other eye when the right image is being displayed.

(c) A lenticular display that presents the images for the left eye and right eye in a unit that is not worn by the user. Instead the image for the left eye and the right eye are produced by a single device in a way that causes the left image to be projected at an angle visible to the left eye and causes the right image to be projected at an angle visible to the right eye.

Holograms can be described generally as three-dimensional images that do not require any structure worn by a user for the display of the 3D image to a user. A hologram is physical structure that diffracts light into an image. The term 'hologram' can refer to both the encoded material and the resulting image. It can be described as a photographic recording of a light field, rather than of an image formed by a lens, and it is used to display a fully three-dimensional image of the holographed image or object. The hologram itself is not an image and it is usually unintelligible when viewed under diffuse ambient light. It is an encoding of the light field as an interference pattern of seemingly random variations in the opacity, density, or surface profile of the photographic medium. When suitably lit, the interference pattern diffracts the light into a reproduction of the original light field and the objects that were in it appear to still be there, exhibiting visual depth cues such as parallax and perspective that change realistically with any change in the relative position of the observer. In its pure form, holography requires the use of laser light for illuminating the subject and for viewing the finished hologram. A holographic display can have the ability to address all four of the following eye mechanisms: binocular disparity; motion parallax; eye accommodation; and eye convergence. In a holographic display, the 3D objects can be viewed without wearing any special glasses and no visual fatigue will be caused to human eyes.

Vestibulo-ocular reflex (or VOR) refers to the ocular (e.g. human visual motor system) response to stimulus of the vestibular (e.g. inner ear) system, in which the eye movement response is caused by head movement. More specifically, VOR is an involuntary movement of the eyes in response to rotational movements of the head detected by the inner ear balance system. As will be described further in this disclosure, measures of VOR can include gain, phase, symmetry, and saccadic responses to head movements at various frequencies. The VOR stabilizes the visual image on the back of the eye (retina) during head movement by producing an eye movement in the direction opposite to head movement, thus preserving the image on the center of the visual field (e.g. on the fovea). This allows a person to visualize objects clearly during brief head movements. A simplistic view of the VOR involves a 3-neuron arc that consists of the vestibular ganglion, vestibular nuclei, and oculomotor nuclei. When the head moves, the VOR responds with an eye movement that is equal in magnitude but opposite in direction. For example, when the head moves to the right, the eyes move to the left and when the head moves up the eyes move downward. Head movements, rotational and translational, stimulate the VOR. With a rotational movement, the head moves relative to the body. Examples of this include turning the head back and forth, nodding, and bringing the ear in contact with the shoulder. Translational movements occur when the entire body, including the head, is moved in tandem. Translational movements may occur when an individual stands on a moving sidewalk. Thus, rotational VOR responds to angular motion of the head and results from stimulation of the semicircular canals, whereas translational VOR responds to linear motion of the head and results from stimulation of the otolithic organs. Some head movements may involve a combination of both translational VOR and rotational VOR. The VOR is a reflex that acts at short latency to generate eye movements that compensate for head rotations in order to preserve clear vision during locomotion. The VOR is the most accessible gauge of vestibular function. Evaluating the VOR requires application of a vestibular stimulus and measurement of the resulting eye movements. For example, when the head moves to the right, the eyes move to the left, and vice versa. The VOR normally serves to stabilize gaze in space during head movements by generating equal and opposite compensatory eye movements. The VOR has both rotational and translational aspects. When the head rotates about any axis (horizontal, vertical, or torsional) distant visual images are stabilized by rotating the eyes about the same axis, but in the opposite direction. When the head translates, for example during walking, the visual fixation point is maintained by rotating gaze direction in the opposite direction, by an amount that depends on distance. Eye movements generated by the human VOR system are intended to stabilize the image on the retina and specifically on the fovea during brief, non-sustained head movements. In order to see the surrounding world clearly, the retinal images on the fovea must remain stable, within certain margins. Stability is affected, however, by the continuous movements of the head, which may cause motion blur. In order to prevent motion blur, head movements are counter-balanced by compensatory eye movements. These are mediated by two reflexes, the VOR, which senses head rotations in the labyrinth, and the optokinetic reflex (OKR), which directly senses visual image motion. Vestibulo-ocular eye movements that reflexively occur in the direction opposite a head movement can also be included within eye signal controls during voluntary head movements. Measurement of the VOR is related to the semicircular canal being tested in the direction of the motion of the head movement. This most often includes both vertical and horizontal VOR tests. Eye-velocity response to the head-velocity stimulus can be seen with the VOR gain for the two directions of rotation and overt and covert saccades can also be identified and measured. During VOR testing, if the person's vestibulo-ocular response is abnormal, then their eyes will be taken off target during the head rotation, because their eyes will not rotate at the correct speed to exactly compensate for head rotation. In this instance, an abnormal VOP means that the eyes can move with the head during a passive unpredictable head turn and will be taken off target by the head turn, so that at the end of the head turn the person must make a corrective saccade toward the target.

A saccade is a fast movement of an eye, head or other part of the body or of a device. It can also be a fast shift in frequency of an emitted signal or other quick change. Saccades are quick, simultaneous movements of both eyes in the same direction. Humans do not look at a scene in fixed steadiness, the eyes move around, locating interesting parts of the scene and building up a mental, three-dimensional 'map' corresponding to the scene. When scanning the scene in front of you or reading these words right now, your eyes make jerky saccadic movements and your eyes stop several times, moving very quickly between each stop. We cannot consciously control the speed of movement during each saccade; the eyes move as fast as they can. One reason for the saccadic movement of the human eye is that the central part of the retina (known as the fovea) plays a critical role in resolving objects. By moving the eye so that small parts of a scene can be sensed with greater resolution, body resources can be used more efficiently. The saccade that occurs at the end of a head turn with someone who has an abnormal VOR is usually a very clear saccade, and it is referred to as an overt saccade. An overt saccade is indicative of abnormal semicircular canal function on the side to which the head was rotated. For example, an overt saccade after a leftwards head rotation means the left semicircular canal has a deficit. Covert saccades are small corrective saccades that occur during the head movement of a person with abnormal inner ear function. Covert saccades reduce the need for overt saccades that the end of the head movement and are more difficult to identify than overt saccades. Covert saccades are very fast. This makes them almost impossible to detect by the naked eye, and therefore sensitive eye tracking measurements are typically required to detect covert saccades. There is a rapid deceleration phase as the direction of sight lands on the new target location. Following a very short delay, large saccades are frequently accompanied by at least one smaller corrective saccade to further approach a target location. Corrective saccades can occur even if the target has been made to disappear, further supporting the projected, ballistic nature of saccadic movements. However, corrective saccades are more frequent if the target remains visible.

Accuracy, amplitude, latency and velocity can be measured with oculomotor eye movements, most commonly with saccades, vergence, smooth pursuit, and vestibulo-ocular movements. Saccades can be elicited voluntarily, but occur reflexively whenever the eyes are open, even when fixated on a target. They serve as a mechanism for fixation, rapid eye movement, and the fast phase of optokinetic nystagmus. The rapid eye movements that occur during an important phase of sleep are also saccades. After the onset of a target appearance for a saccade, it takes about 200 ms for eye movement to begin. During this delay, the position of the target with respect to the fovea is computed (that is, how far the eye has to move), and the difference between the initial and intended position, or "motor error" is converted into a motor command that activates the extraocular muscles to move the eyes the correct distance in the appropriate direction. The latency, amplitude, accuracy and velocity of each respective corrective saccade and latency totals and accuracy can be calculated.

Saccade accuracy refers to the eye's ability to quickly move and accurately shift from one target fixation to another. Saccade adaptation is a process for maintaining saccade accuracy based on evaluating the accuracy of past saccades and appropriately correcting the motor commands for subsequent saccades. An adaptive process is required to maintain saccade accuracy because saccades have too short a duration relative to the long delays in the visual pathways to be corrected while in flight.

Saccade amplitude—refers to the size of the eye movement response, usually measured in degrees or minutes of arc. The amplitude determines the saccade accuracy. This is sometimes denoted using "gain". It is also described as the angular distance the eye travels during the movement. For amplitudes up to 15 or 20°, the velocity of a saccade linearly depends on the amplitude (the so-called saccadic main sequence). Saccade duration depends on saccade amplitude. In saccades larger than 60 degrees, the peak velocity remains constant at the maximum velocity attainable by the eye. In addition to the kind of saccades described above, the human eye is in a constant state of vibration, oscillating back and forth at a rate of about 60 Hz.

Saccade velocity—this is the speed measurement during the eye movement. High peak velocities and the main sequence relationship can also be used to distinguish micro-/saccades from other eye movements like (ocular tremor, ocular drift and smooth pursuit).

Saccade latency—this is the time taken from the appearance of a target to the beginning of an eye movement in response to that target. Disorders of latency (timing) can be seen with saccades, VOR and visual pursuit.

Saccadic Inhibition. Studies of eye movements in continuous tasks, such as reading, have shown that a task-irrelevant visual transient (for example a flash of a portion of the computer display) can interfere with the production of scanning saccades. There is an absence or near-absence of saccades initiated around 80-120 ms following the transient. This inhibitory effect (termed saccadic inhibition SI) is also observed in simple saccade experiments using small visual targets and it has been suggested that SI may be similar to, or underlie, the remote distractor effect.

Visual pursuit means the movement of the eyes in response to visual signals. Smooth pursuit eye movements allow the eyes to closely follow a moving object. It is one of two ways that humans and other visual animals can voluntarily shift gaze, the other being saccadic eye movements. Pursuit differs from the VOR, which only occurs during movements of the head and serves to stabilize gaze on a stationary object. Most people are unable to initiate pursuit without a moving visual signal. The pursuit of targets moving with velocities of greater than 30°/s tend to require catch-up saccades. Most humans and primates tend to be better at horizontal than vertical smooth pursuit, as defined by their ability to pursue smoothly without making catch-up saccades. Most humans are also better at downward than upward pursuit. Pursuit is modified by ongoing visual feedback. Smooth pursuit is traditionally tested by having the person follow an object moved across their full range of horizontal and vertical eye movements.

Visual pursuit tracking can be defined as measuring a person's eye movement ability to match a visual element or target of interest movement. Visual pursuit eye movements utilize some of the vestibulo-ocular reflex pathways and require a visual input to the occipital cortex in order to permit locking of the eyes onto a visual element or target of interest. Pursuit movements are described to be voluntary, smooth, continuous, conjugate eye movements with velocity and trajectory determined by the moving visual target. By tracking the movement of the visual target, the eyes maintain a focused image of the target on the fovea. A visual stimulus (the moving visual target) is required to initiate this eye movement. Pursuit gain, which is the ratio of eye velocity to target velocity, is affected by target velocity, acceleration and frequency. Visual pursuit tracking may be related to factors that are difficult to quantify, such as the degree of alertness present in persons, visual acuity or the visibility of the pursuit target. Visual pursuit tracking can be decayed with alcohol, centrally acting medications such as anticonvulsants, minor tranquilizers, preparations used for sleep. It is also clear that visual pursuit performance declines with age and can be adversely affected by vestibular dysfunction, central nervous system disorders and trauma, such as concussions and traumatic brain injury (TBI).

Visual pursuit accuracy is defined by the ability of the eyes to closely follow a moving object. The pursuit of targets moving with velocities of greater than 30°/s tends to require catch-up saccades. Smooth pursuit accuracy, represents how closely the percentage of time the smooth pursuit velocity value remains within the target velocity value.

Visual pursuit movements are much slower tracking movements of the eyes designed to keep the moving stimulus on the fovea. Such movements are under voluntary control in the sense that the observer can choose whether to track a moving stimulus. Although it may appear that our eyes are not moving when we fixate an object, in fact they are in continual small-scale motion, showing irregular drift and tremor, interspersed by miniature saccadic movements (less than 0.5 degrees). These fixational eye movements are essential to prevent our visual percept from fading. Pursuit consists of two phases—initiation and maintenance. Measures of initiation parameters can reveal information about the visual motion processing that is necessary for pursuit.

Visual pursuit acceleration—this is the rate of change of the eye velocity. The first approximately 20 milliseconds of pursuit tends to be the same regardless of target parameters. However, for the next 80 milliseconds or so, target speed and position has a large effect on acceleration.

Visual pursuit velocity—After pursuit initiation, speed of the eye movement (velocity) usually rises to a peak and then either declines slightly or oscillates around the target velocity. This peak velocity can be used to derive a value for gain (peak velocity/target velocity). It is usually near the velocity of the target. Instead of using peak velocity, it is also sometimes of interest to use measures of velocity at particular times relative to either target appearance or pursuit initiation. Eye velocity up to 100 milliseconds after target appearance can be used as a measure of prediction or anticipation. Velocity measured 100 milliseconds after pursuit begins reveals something about the ability of pursuit system in the absence of visual feedback.

Visual pursuit latency—is defined by the time from target appearance to the beginning of pursuit. The difficulty here is defining when pursuit begins. Usually it is measured from traces of eye velocity. It is often calculated by finding the intersection between two regression functions one fitted to velocity about the time of target appearance, and the second fitted over the initial part of the pursuit response.

Nystagmus is a description of abnormal involuntary or uncontrollable eye movement, characterized by jumping (or back and forth) movement of the eyes, which results in reduced or limited vision. It is often called "dancing eyes". Nystagmus can occur in three directions: (1) side-to-side movements (horizontal nystagmus), (2) up and down movements (vertical nystagmus), or (3) rotation of the eyes as seen when observing the front of the face (rotary or torsional nystagmus).

Vergence is the simultaneous movement of both eyes in opposite directions to rapidly obtain or maintain single binocular vision or ocular fusion, or singleness, of the object of interest. It is often referred to as convergence or divergence of the eyes, to focus on objects that are closer or further away from the individual. The maintain binocular vision, the eyes must rotate around a vertical axis so that the projection of the image is in the center of the retina in both eyes. Vergence measurements can easily be performed. Normally, changing the focus of the eyes to look at an object at a different distance will automatically cause vergence and accommodation, known as accommodation-convergence reflex. Convergence is the simultaneous inward movement of both eyes toward each other, usually in an effort to maintain single binocular vision when viewing an object. Vergence tracking occurs in the horizontal, vertical, and/or cyclorotary dimensions. Vergence requires that the occipital lobes be intact and the pathway involves the rostral midbrain reticular formation (adjacent to the oculomotor nuclei) where there are neurons that are active during vergence activities. It comprises a complex and finely tuned interactive oculomotor response to a range of sensory and perceptual stimuli. There is an important interaction between the vergence system and vestibular (inner ear balance) system. In order to keep the eyes focused on a visual element or object of interest, while the head is moving, the vestibular system senses head rotation and linear acceleration, and activates the eyes to counterrotate so as to keep gaze constant even though the head is moving. As an example, this is what enables us to see a tennis ball while moving our head. The problem becomes more difficult at near vision, because the eyes are not located at the center of rotation of the head, but rather are about 10 cm anterior to the axis of rotation. Therefore, when a person is focused on a near target (such as 10 cm away), the amount of eye movement needed to keep the target fixated is much greater than the amount needed to view a similar object 100 cm away. This additional eye movement is supplied by the otoliths (linear acceleration sensors) that produce eye movement that are roughly inversely proportional to the distance of the target from the center of the eye. Persons with disorders of their otoliths, might reasonably have a selective problem with stabilizing their vision while the head is moving, at near vision. Vergence can be also be adversely affected by other factors including aging, visual abnormalities, concussion and traumatic brain injury (TBI).

Eyelid closure refers to the distance between the margins of the upper and lower eyelid and is often measured by palpebral fissure height, marginal reflex distance, levator function and upper eyelid crease. The palpebral fissure height (PF) is the distance between the upper and lower eyelid margins at the axis of the pupil. Normal measurement is 9 to 12 mm defined as being either voluntary or involuntary eye-lid movement. Marginal reflex distance (MRD) is the distance between the central corneal light reflex and upper eyelid margin with eyes in primary position. The severity of ptosis is better determined with MRD than PF measurements as lower lid malpositions are eliminated. Normal MRD is 4-5 mm. Levator function is measured as the distance in millimeters (mm) of the upper lid margin when looking downward and when looking upward. Upper eyelid crease position is the distance from the upper eyelid crease to the eyelid margin. It is normally 7-8 mm in males and 9-10 mm in females.

The eyelids act to protect the anterior surface of the globe from local injury. Additionally, they aid in regulation of light reaching the eye; in tear film maintenance, by distributing the protective and optically important tear film over the cornea during blinking; and in tear flow, by their pumping action on the conjunctival sac and lacrimal sac. The closure of the eyelids is facilitated by the protractors of the eyelids: circumferential orbicularis oculi muscle, which is innervated by the facial (seventh cranial) nerve. The elevators of the upper eyelid are the levator palpebrae superioris and the Muller's muscle. The levator palpebrae superioris is the main upper eyelid elevator and is innervated by the oculomotor (third cranial) nerve. The Muller's muscle is a smooth muscle that arises from the undersurface of the levator and inserts into the superior tarsus. The Muller's muscle is innervated by the sympathetic nervous system. The muscle is responsible for the over-elevation of the eyelid when a patient becomes excited or fearful and leads to mild ptosis with fatigue or inattention.

Active movements related to eye-lid closure can be referred to as eyelid contractions, twitches or blinks and can occur spontaneously, reflexively, or voluntarily. Spontaneous blinking which is done without external stimuli and internal effort. This type of blinking is conducted in the pre-motor brain stem and happens without conscious effort. A reflex blink occurs in response to an external stimulus, such as contact with the cornea or objects that appear rapidly in front of the eye. A reflex blink is not necessarily a conscious blink either; however, it does happen faster than a spontaneous blink. Reflex blink may occur in response to tactile stimuli, optical stimuli or auditory stimuli. Voluntary blink is larger amplitude than Reflex blink, with the use of all 3 divisions of the orbicularis oculi muscle. Generally, between each blink is an interval of 2-10 seconds; actual rates vary by individual averaging around 10 blinks per minute in a laboratory setting. However, when the eyes are focused on an object for an extended period of time, such as when reading, the rate of blinking decreases to about 3 to 4 times per minute. This is the major reason that eyes dry out and become fatigued when reading. Blinks affect not only horizontal saccades but also vertical saccades, vergence eye movements, and saccade-vergence interaction in humans. While the saccade and vergence duration is increased during blinks, the peak velocity, acceleration and deceleration is decreased. In contrast, the amplitude of saccades and vergence does not appear to change during blinks. Blinks during gaze straight ahead elicited an eye movement toward the nose and downward. Blinks have a maximum effect when elicited ~100 ms before eye movements. All blink-elicited eye movements started with the blink onset but were completed before the end of the blink. Blink speed can be affected by elements such as fatigue, eye injury, medication, and disease. For example, blepharospasm is any abnormal contraction or twitch of the eyelid. In most cases, symptoms last for a few days then disappear without treatment, but sometimes the twitching is chronic and persistent, causing lifelong challenges.

Apraxia of eyelid opening is a condition in which patients who have otherwise normal eyelids have difficulty opening the eyelids. Pure apraxia of lid opening (which is not associated with blepharospasm) is very rare. However, apraxia of lid opening is commonly associated with blepharospasm.

Visual acuity (VA) refers to acuteness or clearness of vision, which is dependent on optical and neural factors, i.e., (i) the sharpness of the retinal focus within the eye, (ii) the intactness and functioning of the retina, and (iii) the sensitivity of the interpretative faculty of the brain. A Snellen chart (eye chart that uses block letters arranged in rows of various sizes) is frequently used for visual acuity testing and measures the resolving power of the eye, particularly with its ability to distinguish letters and numbers at a given distance as well as the sharpness or clearness of vision.

The dynamic visual acuity (DVA) can be used interchangeably with kinetic visual acuity (KVA) as they both have the same meaning. In this document, DVA will be used to assess impairments in a person's ability to perceive objects accurately while actively moving the head, or the ability to track a moving object. It is an eye stabilization measurement while the head is in motion. In normal individuals, losses in visual acuity are minimized during head movements by the vestibulo-ocular system that maintains the direction of gaze on an external target by driving the eyes in the opposite direction of the head movement. When the vestibulo-ocular system is impaired, visual acuity degrades during head movements. The DVA is an impairment test that quantifies the impact of the vestibulo-ocular system pathology on a user's ability to maintain visual acuity while moving. Information provided by the DVA is complementary to and not a substitute for physiological tests of the VOR system. The DVA quantifies the combined influences of the underlying vestibulo-ocular pathology and the person's adaptive response to pathology. DVA testing is sometimes obtained for those persons suspected of having an inner ear abnormality. Abnormalities usually correlate with oscillopsia (a visual disturbance in which objects in the visual field appear to oscillate or jump while walking or moving). Currently with DVA testing, worsening of visual acuity by at least three lines on a visual acuity chart (e.g., Snellen chart or Rosenbaum card) during head turning from side to side at 1 Hz or more is reported as being abnormal. In normal individuals, losses in visual acuity are minimized during head movements by the vestibulo-ocular system that maintains the direction of gaze on an external target by driving the eyes in the opposite direction of the head movement When the vestibular system is impaired, visual acuity degrades during head movements. Individuals with such ocular performance deficits can improve their dynamic acuity by performing rapid "catch-up" saccadic eye movements and/or with predictive saccades.

Dynamic visual stability (DVS) and retinal image stability (RIS) can be used interchangeably. In this document, DVS will be used to describe the ability to visualize objects accurately, with foveal fixation, while actively moving the head. When the eye moves over the visual scene, the image of the world moves about on the retina, yet the world or image observed is perceive as being stable. DVS enables a person to prevent perceptual blurring when the body moves actively. The goal of oculomotor compensation is not retinal image stabilization, but rather controlled retinal image motion adjusted to be optimal for visual processing over the full range of natural motions of the body or with head movement. Although we perceive a stable visual world, the visual input to the retina is never stationary. Eye movements continually displace the retinal projection of the scene, even when we attempt to maintain steady fixation. Our visual system actively perceives the world by pointing the fovea, the area of the retina where resolution is best, towards a single part of the scene at a time. Using fixations and saccadic eye movements to sample the environment is an old strategy, in evolutionary terms, but this strategy requires an elaborate system of visual processing in order to create the rich perceptual experience. One of the most basic feats of the visual system is to correctly discern whether movement on the retina is owing to real motion in the world or rather to self-movement (displacement of our eyes, head or body in space). The retinal image is never particularly stable. This instability is owing to the frequent occurrence of tremors, drifts, microsaccades, blinks and small movements of the head. The perceptual cancellation of ocular drift appears to primarily occur through retinal mechanisms, rather than extra-retinal mechanisms. Attention also plays a role in visual stability, most probably by limiting the number of items that are fully processed and remembered.

Foveal Fixation Stability (FFS) refers to the ability to maintain an image on the fovea, which is crucial for the visual extraction of spatial detail. If the target image moves 1° from foveal center, or if random movement of the image on the fovea exceeds 2°/sec, visual acuity degrades substantially. Either of these conditions may occur if deficiencies in oculomotor control compromise the ability to maintain target alignment within these limits. Many aspects of oculomotor function do change with age. For example, smooth pursuit movements slow with age, and the range of voluntary eye movements becomes restricted, especially for upward gaze. DVA, FFS, and the vestibulo-ocular reflex decline with age.

Focused position of the eyes can be defined as the position or orientation of the eyes to provide a clear image of a visual element or target of interest on the fovea.

2. Limitations of the Prior Art for a Non-Clinical Environment

Prior art systems for tracking head and eye movements have serious limitations due to the bulkiness of the equipment being used and the high number of the components required. Prior art systems for tracking eye movement include electro-oculography, magnetic scleral search coils, infrared video-nystagmography, and other video eye-tracking devices requiring umbilical attachments to computer systems and light bars or laser pointing systems for eye focusing. Some also utilize solid lights (such as "dots") without specific features to enable a person to focus upon. Additionally, prior art utilizes only two-dimensional images for the person to visualize. Some systems only test one (1) eye, making the measurement of ocular movements and reflexes less accurate. Testing with some prior art systems and methods has little complexity features, has not advanced with available technology and cannot provide images or visual scenes familiar to the person's life activities. These prior art techniques do not allow for more robust and more accurate testing of human ocular performance.

Current clinical eye response measuring equipment is highly specialized, bulky and requires multiple pieces of equipment in a dedicated laboratory. There is need to have a more advanced and robust system and method of measuring human ocular performance. The use of VR/AR/synthetic 3D can greatly advance the measurement of human ocular performance with the potential for helping a person improve his/her ocular performance. Systems and methods incorporating VR/AR/synthetic 3D can be more accurate, by measuring the movements of both eyes with head tracking and can provide a variety of features to the visual elements or targets of interest for the individual to focus upon. Having a stronger visual element can enhance the visual fixation ability during the test being performed on the individual and can improve test accuracy. The use of VR/AR/synthetic 3D can provide unique complexity to the visual elements and to the background scenes to make a more engaging testing environment.

BRIEF DESCRIPTION OF THE DRAWINGS

For a more complete understanding of the present invention and the advantages thereof, reference is made to the following description taken in conjunction with the accompanying drawings in which like reference numerals indicate like features and wherein:

FIG. 11A shows an unaltered visual element;

FIG. 11B shows the visual element of FIG. 11A that has been altered by defocusing the visual element and superimposing a target;

FIG. 12 shows a scene that can be used for optokinetic testing;

Figure 1:
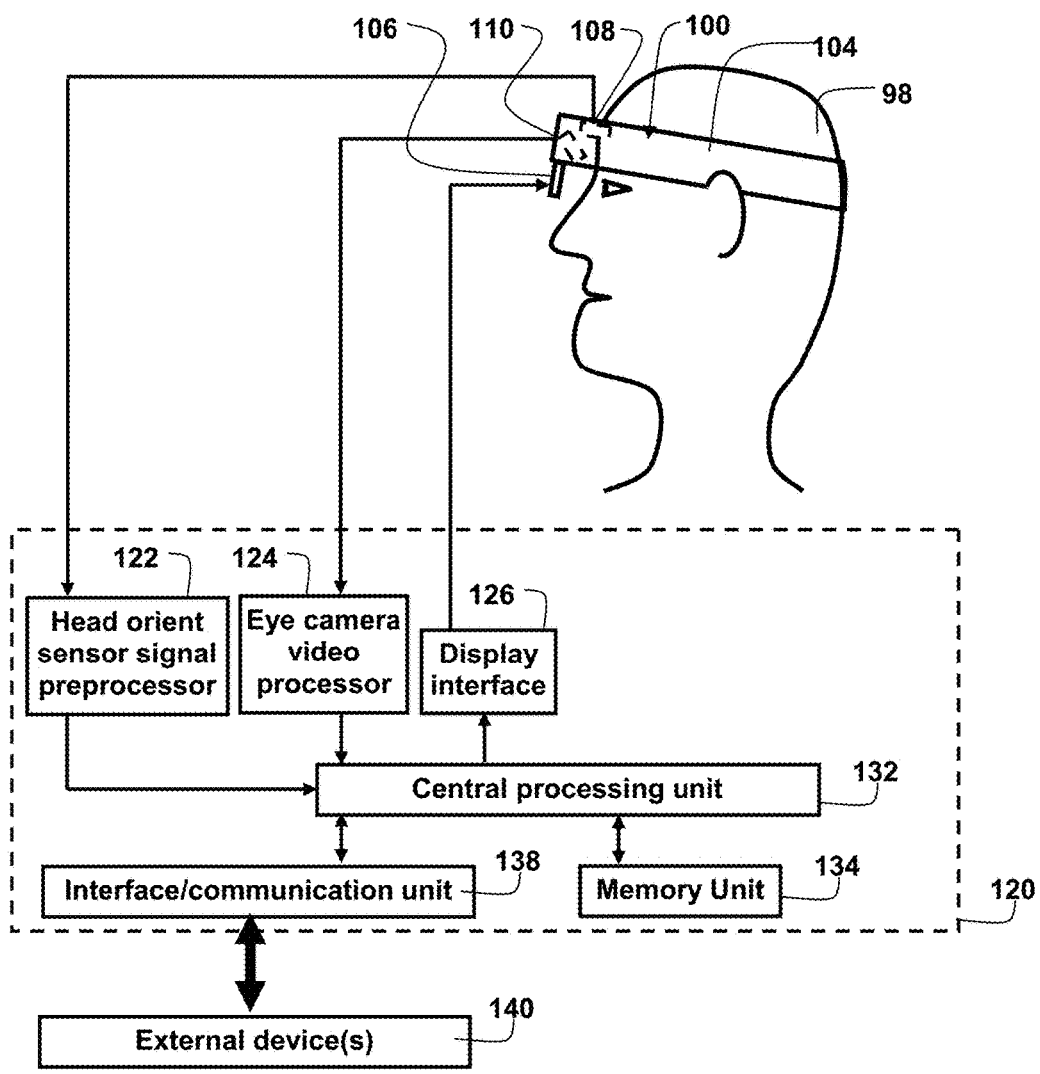
FIG. 1 shows a person wearing an augmented reality ocular performance measuring unit.

It should be understood that the drawings are not necessarily to scale. In certain instances, details that are not necessary for an understanding of the invention or that render other details difficult to perceive may have been omitted. It should be understood that the invention is not necessarily limited to the particular embodiments illustrated herein.

DETAILED DESCRIPTION

The ensuing description provides preferred exemplary embodiment(s) only, and is not intended to limit the scope, applicability or configuration of the disclosure. Rather, the ensuing description of the preferred exemplary embodiment(s) will provide those skilled in the art with an enabling description for implementing a preferred exemplary embodiment.

It should be understood that various changes could be made in the function and arrangement of elements without departing from the spirit and scope as set forth in the appended claims. Preferred embodiments of the present invention are illustrated in the Figures, like numerals being used to refer to like and corresponding parts of the various drawings. Specific details are given in the following description to provide a thorough understanding of the embodiments. However, it will be understood by one of ordinary skill in the art that the embodiments may be practiced without these specific details.

1. Overview of Embodiments of the System and Method.

In one embodiment, the present invention comprises a device for measuring a person's ocular performance by:

(a) Presenting virtual reality, augmented reality, or synthetic computer-generated 3-dimensional information (VR/AR/synthetic 3D) on a display;

(b) tracking head movement; and (c) tracking eye movement as the visual VR, AR, or synthetic 3D information is presented.

VR, AR, or synthetic 3D devices incorporating eye tracking can provide more realistic and immersive methods for identifying and measuring eye movement or oculomotor responses to changes in head orientation. Ocular measurements using VR, AR, or synthetic 3D images can be used to predict human performance, to determine candidacy for specific jobs or tasks, or for neurologic health status assessment (such as alcohol and drug usage, the need for rehabilitation, or for the detection, assessment, or management of concussions and/or traumatic brain injury). Such devices can be an engaging method for human performance assessment and treatment. For example, all six semi-circular canals can be evaluated for normal function, hypofunction, hyperfunction, for the presence of abnormalities such as BPPV, and to help determine if a person has a peripheral vestibular disorder or central disorder. By using such a device with a data interface, all of the information obtained by using the device can be directly shared to other devices or uploaded to remote locations. With these immersive systems of assessment, accuracy of measurement and methods of treatment can easily be provided by visualizing the correct head position and providing the person using these devices an enhanced fixation ability to reposition the otoconia back into the utricle and out of the affected semicircular canal or cupula.

In embodiments of the present invention, vestibular ocular performance (VOP), saccades, visual pursuit performance, nystagmus, vergence, eyelid closure, dynamic visual acuity, dynamic visual stability, retinal image stability, foveal fixation stability, and focused position of the eyes could be measured in a VR, AR or synthetic 3D environment. The embodiments provide an opportunity to create ocular performance tests with a variety of advantages. For example, in an AR/VR environment, tracking can easily be done not only in a purely horizontal or vertical direction, but also using any pattern combining horizontal (i.e. x-direction), vertical (i.e. y-direction), or depth (i.e. z-direction) movement, including but not limited to sinusoidal, pendular, and diagonal scan paths in a three-dimensional space. When testing, the eye tracking sensor or sensors can automatically establish an electronic 'lock-on' to the person's eye. Different speeds of for testing can be available, such as 2 Hz, 4 Hz or 6 Hz. Accuracy of the shift of the eyes from target fixation to another can be measured. Analysis for gain and phase of tracking can also be measured. Peak velocity, amplitude, latency, duration, and inhibition of saccades can additionally be measured. The remote distractor effect can be detected. The slow component velocity (SCV) with optokinetic and gaze testing can also be measured. Smooth pursuit accuracy movements, velocity, acceleration and latency can also be measured. Measurement of oculomotor movement can be performed either with traditional methods or by using variety of pattern, directions and frequency of the image presentation. Oculomotor assessment and measurement in these systems can provide potential higher level of evaluation that what was available in the prior art and this can be performed with static or dynamic methods, both for the object being viewed, as well as for the person using the device and engaged in the testing. Additionally, realistic images can be used to simulate the target of interest or visual element being viewed or the environment in which the person would normal be engaged in when performing his or her activities of choice or occupation. For example, ocular testing can be performed in a mode where the object is static and the person moves the head in a horizontal or vertical manner, or the object can be dynamically changing in size, position, or other features, while the person is rotating the head. Natural or realistic images can be used in the visualized scene, as well as with the target of interest being viewed and measurement of the eye's ability to focus on the target can easily be measured. One can determine a fixation or distraction factor. A person who has a high amount of distraction would most likely not be able to perform as well as another person who had a high fixation factor, in the presence of high distraction scene content.

Embodiments of the present invention can include systems and methods that measure reaction times and/or responses for head, eye, eyelid movements, and/or changes in pupil geometry. Such systems and methods can include eyewear or headwear that comprise one or more eye-tracking cameras for monitoring the position and geometry of at least one eye and its components of the user, one or more scene cameras for monitoring the user's surroundings, and/or one or more processors to determine reaction times. Optionally, the system may include one or more of a multi-axis accelerometer to monitor head movements, one or more light sources to trigger visual evoked responses, and/or electronic inputs that may be used to indicate the time of occurrence of external reference events 2. Detailed Description of the Figures.

Referring now to the figures, FIG. 1 illustrates a person 98 wearing a head-worn augmented reality system for measuring and/or improving vestibular performance, ocular performance, and/or vestibulo-ocular performance. Referring in more detail to FIG. 1, the person is wearing a headband head worn unit 100, which comprises a headband 104, a see-through display 106, a head orientation sensor 108, and an eye measuring sensor 110. The headband 104 is a head attachment element that is designed to fit snugly on the head of the person 98 so that all changes in head orientation result in equal changes in orientation of the head-worn unit 100. The head orientation sensor 108 is rigidly attached to the headband 104. In at least one embodiment, the head orientation sensor 108 senses (is responsive to) pitch, roll, and/or yaw. Pitch can be described as upward or downward movement of the face. Roll can be described as rotation of the face when viewed from the front. Yaw can be described as leftward and rightward movement of the face when viewed from the front. The head orientation sensor 108 can be constructed from one or more elements or it can be monolithic. The head orientation sensor 108 can use one or more accelerometers, gyroscopes, magnetometers, or any other relative or absolute position, velocity, or acceleration sensing device capable of being understood by anyone skilled in the art. In one embodiment, the orientation sensor comprises a micro-electro-mechanical system (MEMS) integrated circuit.

Further referring to FIG. 1, in one embodiment, the eye sensor 110 is more specifically an eye tracking digital video camera that is pointed at the eyes of the person 98. The eye sensor can be responsive to any eye position, including vertical movement of the eyes (which represents pitch), rotation of the eyes (which represents roll), and horizontal movement of eyes (which represents yaw). It can also be responsive to eyelid position. There can be one eye sensor camera 110, that monitors only one eye, one eye sensor camera 110 with a wide angle, that can monitor both eyes, or two cameras, one to monitor each eye. There can also be multiple cameras, to monitor different areas of each eye (e.g. eye response sensors tracking pupil features and corneal reflection surface(s). The eye sensor video camera 110 can be positioned anywhere around the eye, and can utilize visible or invisible light.

In the embodiment shown in FIG. 1, the see-through display 106, head orientation sensor 108 and eye tracking camera 110 are connected to an electronic module 120. The electronic module comprises a head orientation sensor signal pre-processor 122 that is connected to the head orientation sensor 108, an eye camera video processor 124 that is connected to an eye tracking camera (110) connected to an eye camera video processor (124) and a display interface that is connected to the display 106. Inside the electronic module 120, the head orientation sensor signal preprocessor 122, the eye measuring camera video processor 124 and the display interface 126 are connected to a central processing unit 132. Also connected to the central processing unit 132 is a memory unit 134 and an interface and/or communications unit 138. The memory unit 134 can store multiple readings and results, which can be used for data logging, tracking of multiple users, and tracking of performance at various times. The interface and/or communications unit 138 can be connected to an external device 140. Transmission of signals between the communications unit 138 and the external device can be through a wired connection or a wireless connection using any connection method and/or protocol capable of being understood by anyone skilled in the art, including, but not limited to a serial protocol (such as USB), an ethernet protocol (such as TCP/IP), and a cellphone protocol (such as LTE). Additional elements that are not shown, but might be included in the electronic module 120 can be a battery, a battery charge level indicator, and a power management module. The battery in the electronic module could be wirelessly charged. The worn device can contain a dual-purpose charging/connection port and this port could comprise a USB-C or a USB-Micro B connection. The connector on the other side of the charging cable could be a standard rectangular USB connector. The connection could be USB 3.0 or better. Communication between the electronic module 120 and the head worn unit can be through a wired connection or a wireless connection using any connection method and/or protocol including, but not limited to those described for the connection between the electronic module 120 and the external device 140.

Figure 2:
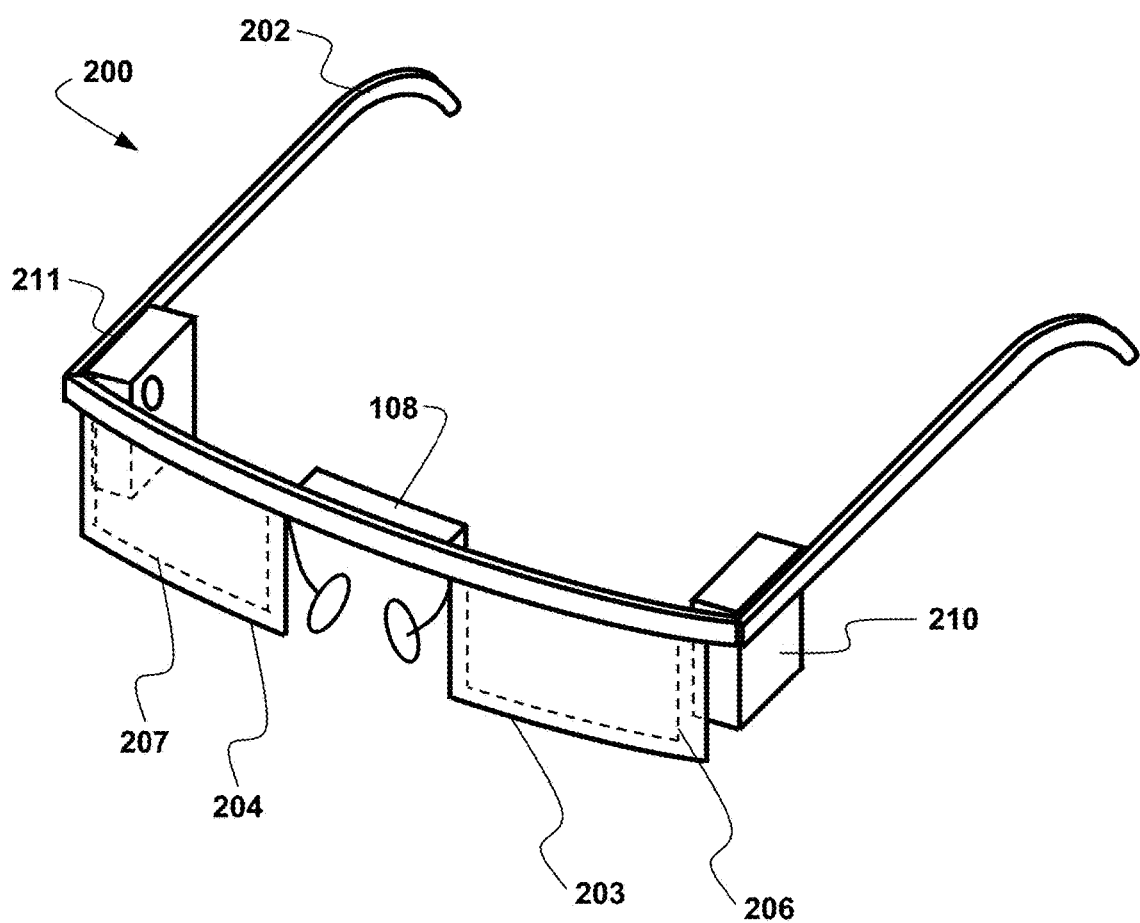
FIG. 2 shows an eyeglasses embodiment of a head-worn augmented reality unit.

FIG. 2 shows an eyeglasses embodiment of a head-worn augmented reality unit 200. The eyeglasses unit 200 shown in FIG. 2 is similar to the headband unit 100 shown in FIG. 1 and could have any of the features and attributes of the unit shown in FIG. 1. The eyeglasses unit 200 could be electronically coupled to an electronic module 120 in FIG. 1 and this electronic module 120 could be part of the eyeglasses unit 200, or the electronic module could be external to the eyeglasses unit 200 and communicate through a wired or wireless connection. The eyeglasses unit could be used for measurement of any human ocular performance parameter. The eyeglasses unit 200 comprises a spectacles frame 202, which serves as the equivalent of the head attachment element (headband) for the embodiment shown in FIG. 1, a left eyeglass 203, and a right eyeglass 204. The left and/or right eyeglasses could be lenses, they could be clear windows, or they could be translucent windows. Also shown are a left display 206 and a right display 207. In the embodiment shown in FIG. 2, the displays, 206 and 207, are see-through displays that are located between the left and right eyeglass, 203 and 204, and the eyes of the person. When the displays, 206 and 207, are in this location, it is not as obvious to an outsider that the unit 200 is an augmented reality unit. The displays, 206 and 207, could also be external to the left and right eyeglasses 203 and 204. In another embodiment, the displays, 206 and 207, could be located within the eyeglass unit, 204 and 205. There could be only one display, 206 or 207. The display could be off-bore and only visible in a person's peripheral vision, such as in the version of Google Glass® that was available in 2014-2015.

Further referring to FIG. 2, the eyeglasses unit also comprises a head orientation sensor located in the bridge 108, a left eye tracking digital video camera 210 and a right eye tracking digital video camera 211. All of these components can be connected similarly and in any configurations and combinations that were described with reference to FIG. 1. In the augmented reality units of FIG. 1 and FIG. 2, the display could be see-through or opaque. If it is opaque, it could cover part or all of the field of view. If it is see-through or opaque and covers only part of the field of view, it could be in one eye or both eyes. If it is opaque and covers the entire field of view, it can only be in one eye. In the embodiments shown in FIG. 1 and FIG. 2, the augmented reality display provides an image of interest or a target for the user to focus on. This image of interest (or target) could be a circular object, such as a pool ball. This image of interest or target could be static (not moving) in the field or view or it could be dynamic (i.e. moving in the field of view).

Figure 3A:
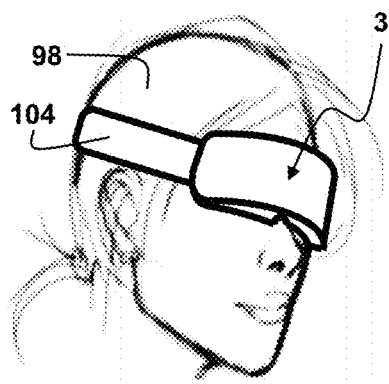
FIG. 3A shows a goggles embodiment of a head-worn virtual reality unit.
Figure 3B:
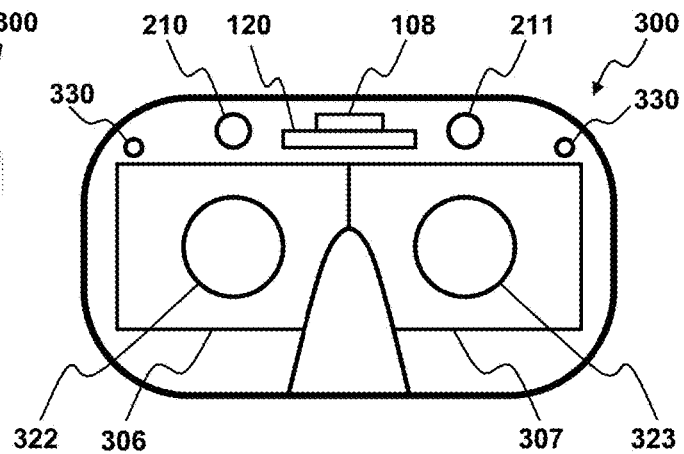
FIG. 3B shows the VR unit of FIG. 3A when viewed from the inside of the goggles looking outward.

FIG. 3A and FIG. 3B show a virtual reality (VR) goggles embodiment of a head-worn device for measuring human ocular performance. FIG. 3A shows the head-worn VR device 300 attached to a person 98 with a strap or headband 104. FIG. 3B shows the head-worn VR device 300 when looked at from the inside looking outward. In the augmented reality (AR) devices of FIG. 1 and FIG. 2, the display (206 and/or 207) is either see-through, or it is opaque, but only covering one eye or part of an eye. In the VR device of FIG. 3A and FIG. 3B, shown at 300, the display, shown at 306 (left display) and 307 (right display), is opaque and the person 98 is typically completely immersed in the scene being displayed. Other than the difference in displays, the VR goggles embodiment 300 can have many of the same elements and configurations that were described with respect to FIG. 1 and FIG. 2 including, but not limited to the head orientation sensor 108, the eye tracking video camera(s) 210 (left eye camera) and 211 (right eye camera), and the electronic module 120. In order for the person's eyes to be able to focus on the displays (306 and 307), there are typically two lenses 322 (left eye lens) and 323 (right eye lens) between the person's eyes and the displays, 306 and 307, when the VR device 300 is worn normally by the person 98. Because the interior of the VR device 300 is not exposed to external light, there can be one or more illumination source(s) 330 to provide light that can be used by the video camera(s) 210 and 211 to sense ocular parameters such as eye or eyelid position or eye motion or any of the other ocular parameters described in other parts of this document. The illumination source or sources 330 can use infrared, near infrared, or visible light.

Referring specifically to the left and right eye tracking digital video cameras, 210 and 211 in FIG. 3B, these cameras (more generally eye sensors) can be used for more than just the tracking of eye position in response to head movement. The eye sensors 210 and 211 can also be used to perform the following functions:

(a) The eye sensors could be used to provide control information. For example, the position of one or both of the eyes (or the orientation or movement of the eyes or eyelids) could be used to determine which of a plurality of choices a user has selected in a menu of options presented on a display. This selection could be to change the scene being displayed to the user. This selection could be used to turn something on or off.

(b) The eye sensors could be used to image one or both retinas of the person 98, to capture anatomic features of a retina, to capture motion and/or orientation of a retina, and/or to determine retinal image stability and/or foveal fixation.

Embodiments of the present invention could also be implemented with eye trackers (also described herein as eye sensors), shown for example at 210 and 211 in FIG. 1, FIG. 2, and FIG. 3B, which are not video cameras. Examples of non-video camera eye trackers can include electromyography trackers and electromagnetic trackers.

Figure 4:
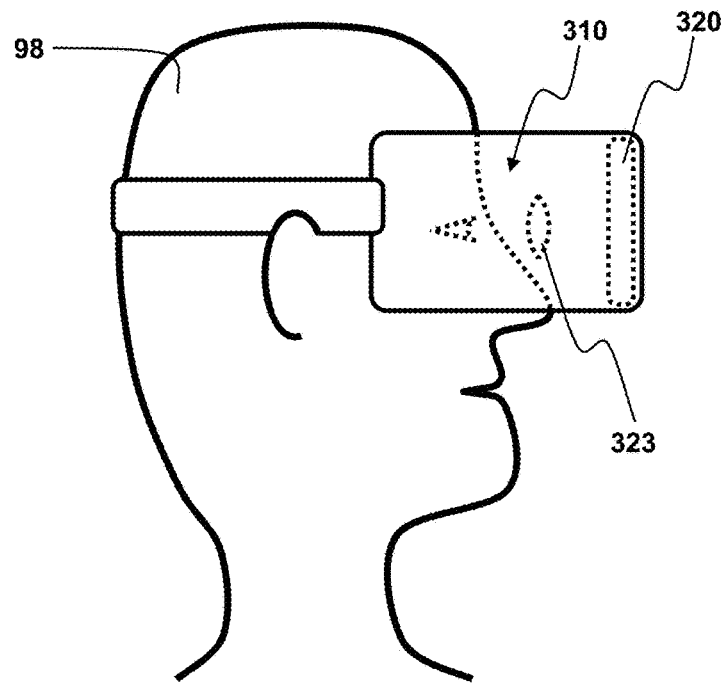
FIG. 4 shows head-worn virtual reality goggles comprising a smartphone.

FIG. 4 shows head-worn virtual reality goggles 310 comprising a smartphone 320. These goggles 310 use the smartphone 320 to provide the display, the eye tracking digital video camera, and the head tracker functionality, and doing many, or all, of the functions of the electronic module. To help the person's eyes focus on the display of the smartphone 320, these virtual reality goggles further comprise one or two lenses 323 that sit between the eyes of the person 98 and the smartphone 320. In the embodiment shown in FIG. 4, the smartphone 320 can contain embedded software to perform all of the necessary functions of measuring all eye movements and/or ocular functions as well as measuring head movements.

Figure 5:
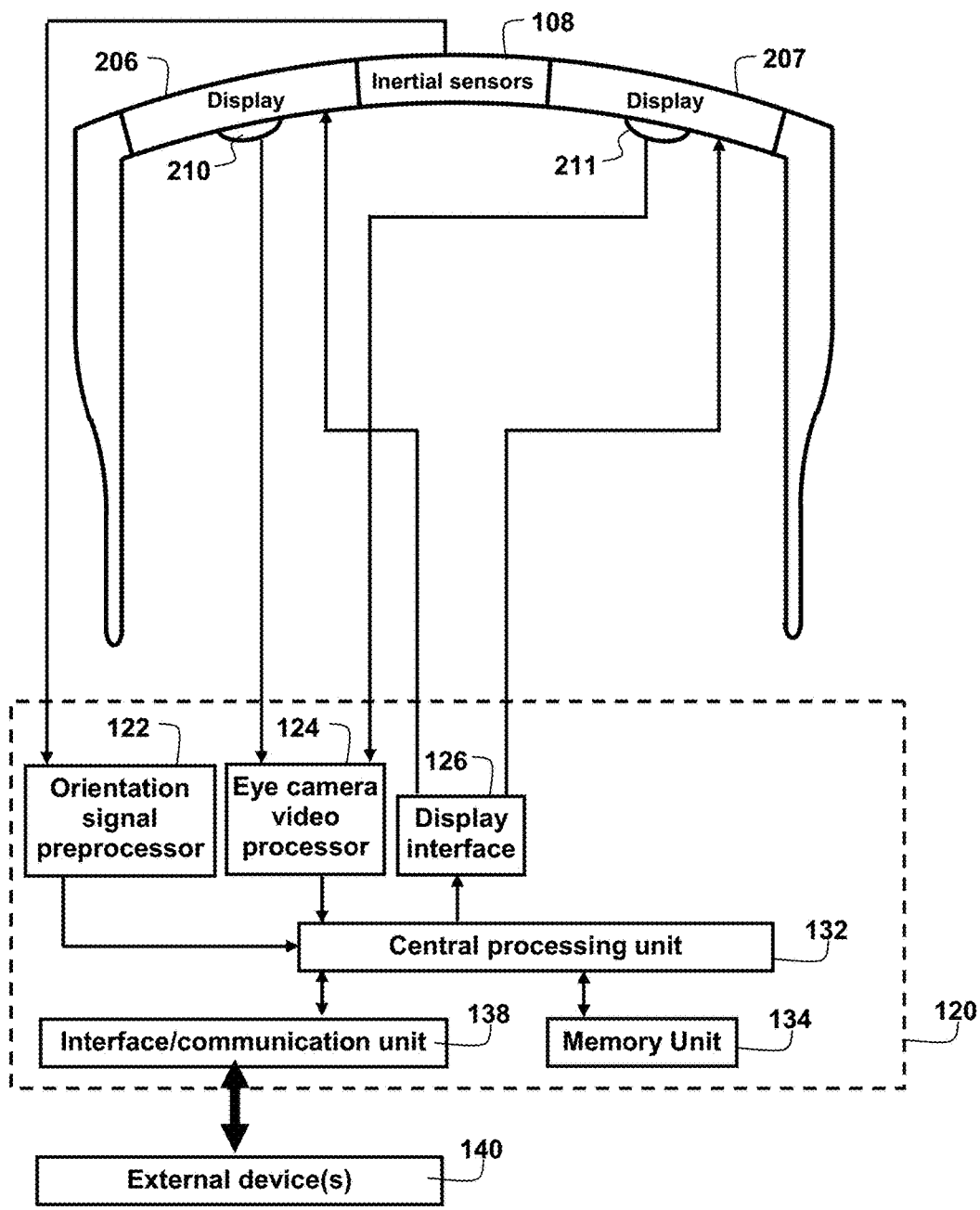
FIG. 5 shows a top view of an augmented reality or virtual reality system.

FIG. 5 shows a top view of an augmented reality or virtual reality system that also includes the main elements that were shown with respect to FIG. 1 to FIG. 4 including a head orientation sensor 108, a left display 206, a right display, a left eye tracking digital video camera 210, a right eye tracking digital video camera 211, an electronic module, an orientation signal preprocessor 122, an eye camera video processor 124, a display interface 126, a central processing unit 132, a memory unit 134, an interface/communication unit 138, and an external device 140.

It should be noted that the AR and VR embodiments of the invention in FIGS. 1-5 can also be implemented using computer-generated 3-dimensional synthetic information instead of the monoscopic or stereoscopic "reality" information used for augmented reality (AR) and virtual reality embodiments discussed with reference to FIGS. 1-5.

Figure 6:
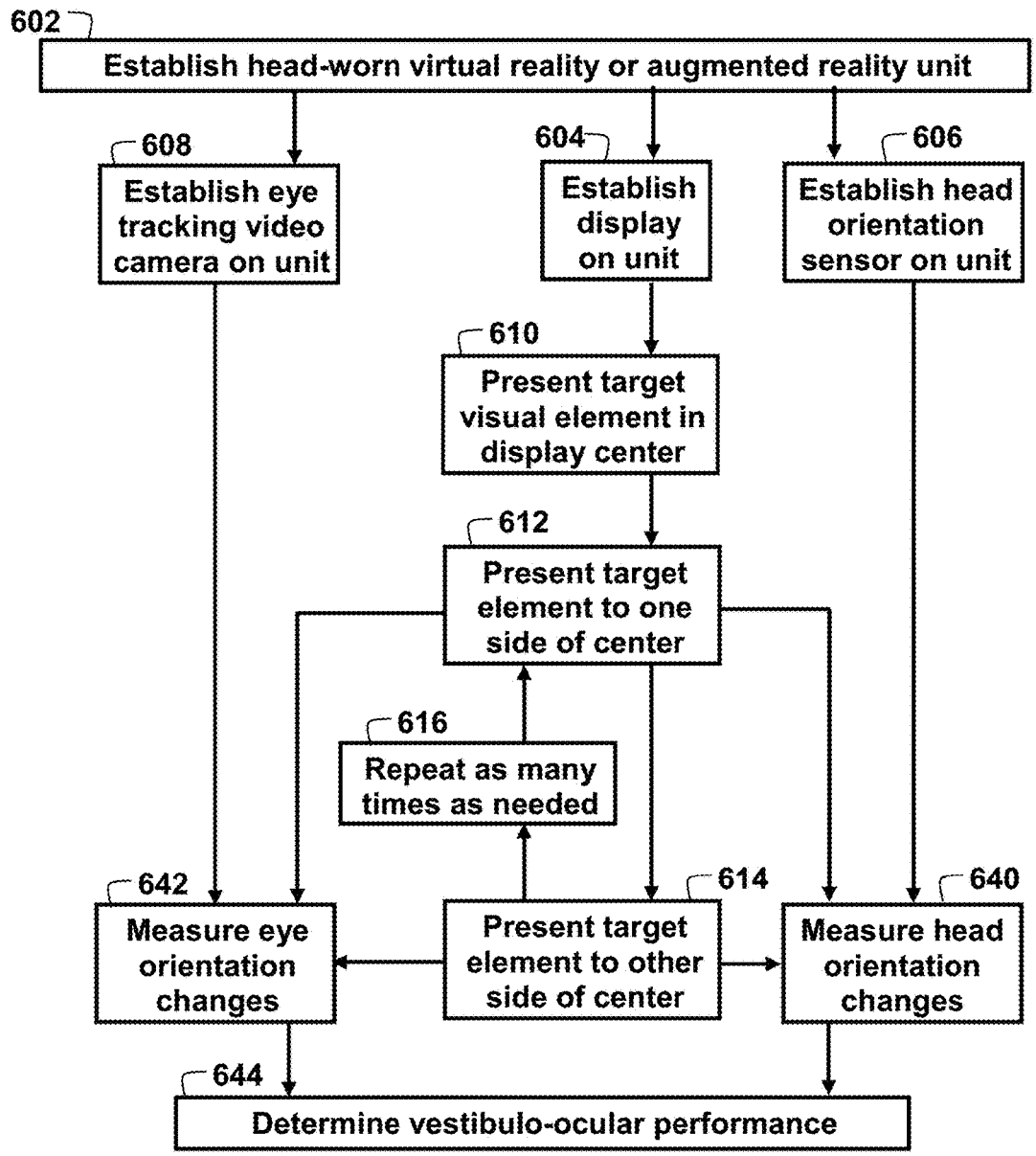
FIG. 6 shows an ocular performance calibration test method.

FIG. 6 shows a vestibulo-ocular performance calibration test that can be implemented using a head-worn AR/VR unit. This test comprises the following configuration and steps:

The AR/VR unit 602 comprises a display 604, a head orientation sensor 606, and an eye tracking video camera 608.

Head: In this test, the subject is asked to keep his/her head motionless or the head is constrained to keep it motionless. The head orientation sensor 640 is used to verify that the head is stationary.

Eyes: The subject is asked to track a visual target element of interest by moving his/her eyes. The eye sensor (typically a video camera) measures the subject's eye movement 642 as visual elements are displayed.

Display: The display background is subdued, plain, solid, and/or non-distracting. In this test, the display background is similar to the background that has been used in prior art VOR testing in which the subject is asked to look at a solid colored wall in the clinician's office which has a bright white circular dot (the target visual element of interest) projected on it. In the AR/VR embodiment of this test, the display background on the head-worn device is similar to the wall of the prior art test. The display also presents a target visual element of interest that can be similar the projected white circular dot of the prior art clinical test or it can be visually enhanced for better image or target eye fixation. The target visual element of interest then behaves in the following way:
1. The target visual element is initially displayed centrally 610.
2. It is then displayed off center on a first side (left or right) of the display center as the central image is dimmed, as shown at 612. This is typically about 20-25 degrees off center.
3. It is then displayed off center on the opposite (or second) side of the display center as the previous image to the first side is dimmed, as shown at 614. This is also typically about 20-25 degrees off center.
4. This process of dimming the target visual element of interest on one side and displaying it on the opposite side is repeated as many times as needed, as shown at 616.
5. This test can be conducted in the vertical, as well as the horizontal direction.

Processor: The processor in the AR/VR system then compares eye movement to timing and appearance/disappearance of visual elements on display, and the location of these visual elements to determine vestibulo-ocular performance 644. Performance could be measured as accuracy, gain, phase, symmetry, velocity, saccades, and/or visual acuity.

Figure 7:
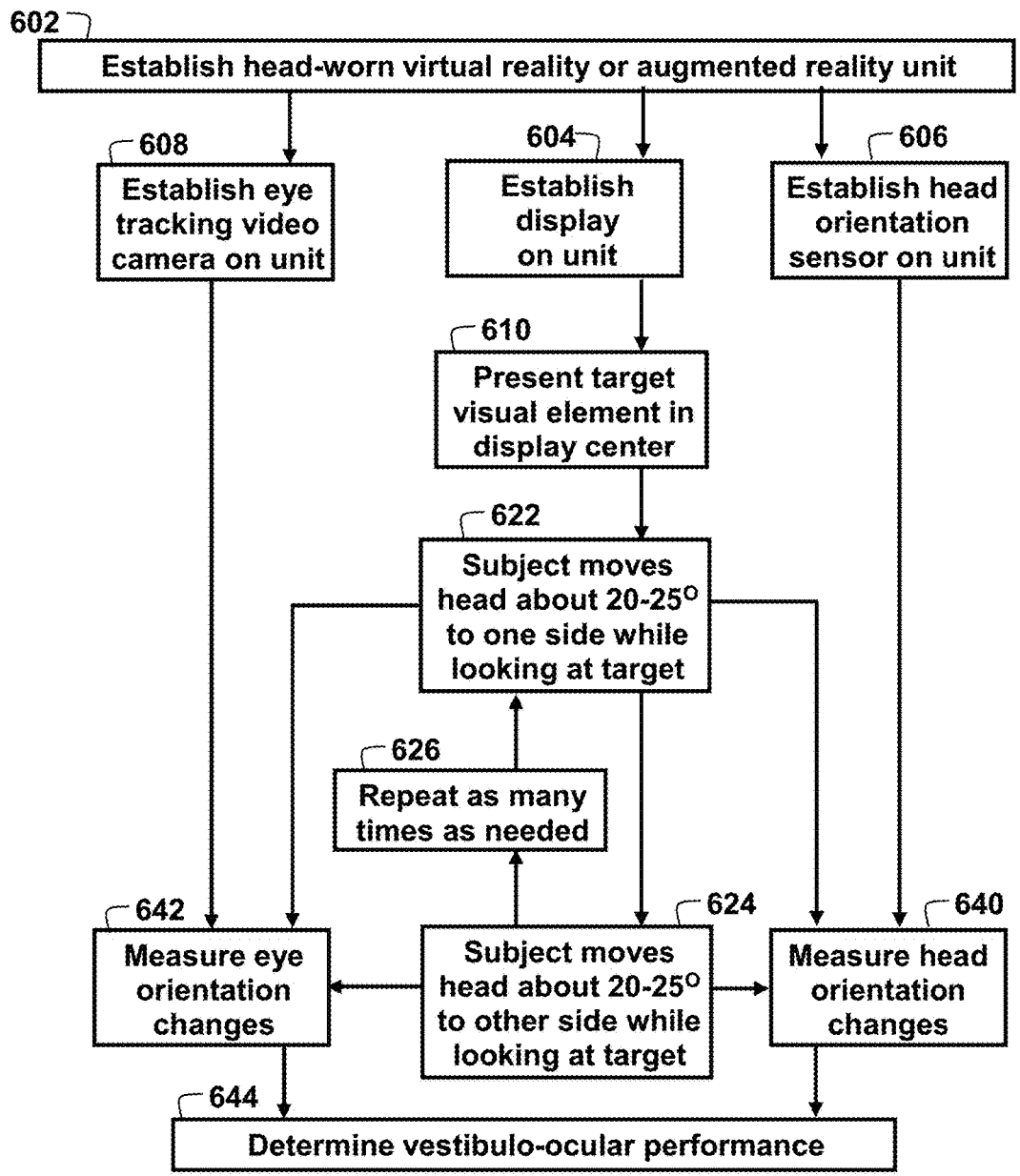
FIG. 7 shows a static active ocular performance test method.

FIG. 7 shows a static active vestibulo-ocular performance test that can be implemented in a head-worn AR or VR unit. This test comprises the following configuration and steps:

The head-worn AR/VR unit 602 comprises a display 604, a head orientation sensor 606, and an eye tracking video camera 608.

Display: In this test, the display is static—neither the background nor the target visual element of interest move or change in any way. The display comprises a subdued background and a centered white circular dot or visually enhanced target element 610, similar to what was described with reference to the test shown in FIG. 6A.

Head: In this test, the subject is asked to actively move his/her head each time he/she is given a cue signal. The head should typically move about 20-25 degrees off center about a vertical axis (i.e. left or right). The head orientation sensor measures changes in head pitch, roll, and/or yaw 640.

Eyes: The subject is instructed to keep his/her eyes focused on the target visual element as the head moves. The eye sensor (typically a video camera) measures eye movement 642 relative to head movement 640.

Cues are provided to tell the subject when to move the head. These cues can be audio cues. The cues could be haptic (i.e. tap on the hand). The cues could be visual (i.e. change of color or intensity of the visual target element of interest). The cues are typically timed randomly so the subject doesn't try to anticipate the timing.

The test sequence is as follows:
1. The subject is instructed to move the head about 20-25 degrees in one direction when a first cue is given, and to hold the head in this new position 622.
2. The subject is instructed to move the head back about 20-25 degrees when the second cue is given 624.
3. The subject is instructed to move the head the first direction a second time when the third cue is given.
4. The process is repeated as many times as needed 626.
5. This test can be conducted in the vertical, as well as the horizontal direction.

Processor: The processor in the AR/VR system then compares eye movement to timing and appearance/disappearance of visual elements on display, and the location of these visual elements to determine vestibulo-ocular performance 644. Performance could be measured as accuracy, gain, phase, symmetry, velocity, saccades, and/or visual acuity.

Figure 8:
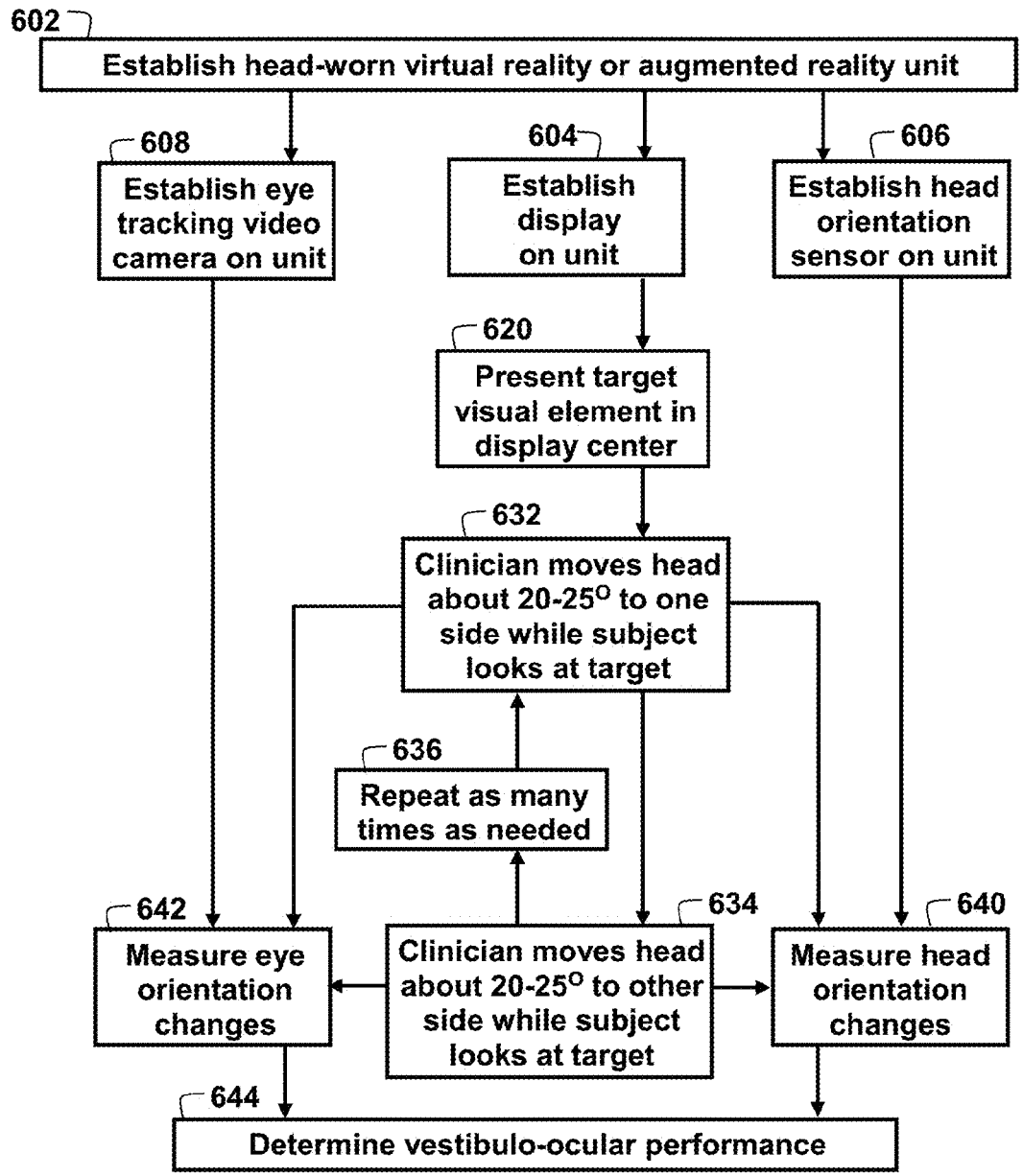
FIG. 8 shows a static passive ocular performance test method.

FIG. 8 shows a static passive vestibulo-ocular performance test that can be implemented in a head-worn AR or VR unit. This test comprises the following configuration and steps:

The head-worn AR/VR unit 602 comprises a display 604, a head orientation sensor 606, and an eye tracking video camera 608.

Display: In this test, the display is the same as for the test described with reference to FIG. 6B, with a target visual element presented in the center 610.

Head: In this test, the clinician holds the subject's head and moves it about 20-25 degrees each time 632. The head orientation sensor measures changes in head pitch, roll, and/or yaw 640.

Eyes: The subject is instructed to keep his/her eyes focused on the target visual element as the head moves. The eye sensor (typically a video camera) measures eye movement relative to head movement 642.

The test sequence is as follows:
1. The clinician moves the subject's head about 20-25 degrees in one direction and then holds it in this new position 632.
2. The clinician then moves the head back 20-25 degrees and holds it 634.
3. The clinician moves the head the first direction a second time.
4. The process is repeated as many times as needed 636.
5. This test can be conducted in the vertical, as well as the horizontal direction.

Processor: The processor in the AR/VR system then compares head movement and eye movement to determine vestibulo-ocular performance 644. Performance could be measured as accuracy, gain, phase, symmetry, velocity, saccades, and/or visual acuity.

There can be many additional embodiments of the ocular performance tests described with reference to FIG. 6, FIG. 7, and FIG. 8. Some of these embodiments can include combinations of the variations listed here:

a. The visual target element (an example of which would be a white dot or a visually enhanced target element) can be any other shape, size, or coloring or have any other features capable of being understood by anyone skilled in the art. Examples of these variations in the target visual element could include:
   A different shape (such as a shape comprising a cross hair);
   Different contrast, either more or less;
   Different intensity;
   Different size;
   Different focus, either more in-focus or out of focus;
   Having one or more features in the visual element that move relative to the rest of the visual element;
   The appearance of a natural object (such as a baseball, a basketball, or a bird); and/or;
   Any combination of any of the above.

b. The test shown in FIG. 7. or FIG. 8 could be run with the target visual element not being stationary. This would make the overall test more similar to a natural environment in which the head, the eyes, and the visual world are all moving relative to one another and relative to a stationary reference frame at all times. When implemented on a display in an AR/VR environment, this would mean that the target visual element could:
   Move with the head movement;
   Move contrary to the head movement;
   Move perpendicular to head movement; and/or
   Move in any random pattern not associated with head movement c. The background (traditionally a subdued, plain, solid, and/or non-distracting wall of a clinician's) office could be presented on the display of the AR/VR system as any other background understood by anyone skilled in the art. Examples of variations of the background can include embodiments in which the background is more natural and similar to actual scene and/or any of the variations in the following list:
   The background can be completely static;
   The background can have moving and/or flashing elements;
   The background can be enhanced with auditory distractions consistent with the imagery being displayed;
   The background can be in or out of focus;
   The background can be low intensity/contrast or high intensity/contrast relative to target of interest;
   The object of interest or image can utilize foveated rendering, in which only the target of interest which the user is visualizing is seen clearly, where the fovea is focused, and the remainder of the adjacent region is less detailed.

Visual acuity, visual fixation ability, DVA (dynamic visual acuity) and FVS (foveal visual stability) can be tested using a system and method similar to the vestibulo-ocular performance (VOP) test shown in FIG. 7. The following are the main elements of a DVA or FVS test performed in this way using a VR or AR environment:

Step 1. Perform a routine vision test by presenting a Snellen chart, or something similar, using the display of the AR/VR unit. This is needed to establish a baseline visual acuity in a static environment. This static test does not necessarily need to be done with a Snellen chart (the standard chart used by optometrists and ophthalmologists), it could also be done by asking the subject to identify characters of various sizes, positions, and/or locations.

Step 2. The subject is presented a visual element (such as a number or letter) in the display center in a manner similar to step 610 of FIG. 7, but in the case of a DVA or FVS test, the target visual element also comprises a character that the subject must identify.

Step 3. The size and character of the target visual element in the display center changes at random times while the subject is performing the steps described at 622 and 624 in FIG. 7.

Step 4. The subject speaks out the character observed each time it changes.

A VR/AR environment can also be used for positional testing. For example, VR goggles can be configured to display a background that has illumination, but no definable image that might provide orientation information to the subject. The subject, could then be asked to turn the head left, right, lie supine, while supine head turns right, head turns left, then turn the body (roll) right and turn the body (roll) left. During each positional change, the eyes are tracked using the AR/VR system to look for abnormal eye movements. If a target visual element was visible during this testing the nystagmus would be suppressed. However, elements with poor contrast can be displayed to provide a more immersive test environment. Visual elements in this instance should not have defining characteristics that might enable eye fixation.

A subject can be tested for BPPV using the method shown in FIG. 8 with the clinician moving the head in a specific pattern that allows the individual semicircular canals to be tested. Note that this means the head is not moved the 20 degrees side-to-side, but is instead moved based on standard protocol for the specific semicircular canal being tested.

Figure 9A:
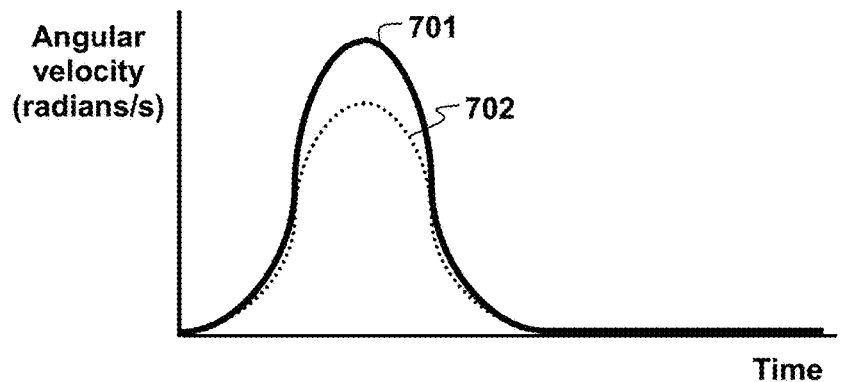
FIG. 9A shows vestibulo-ocular gain measurement.
Figure 9B:
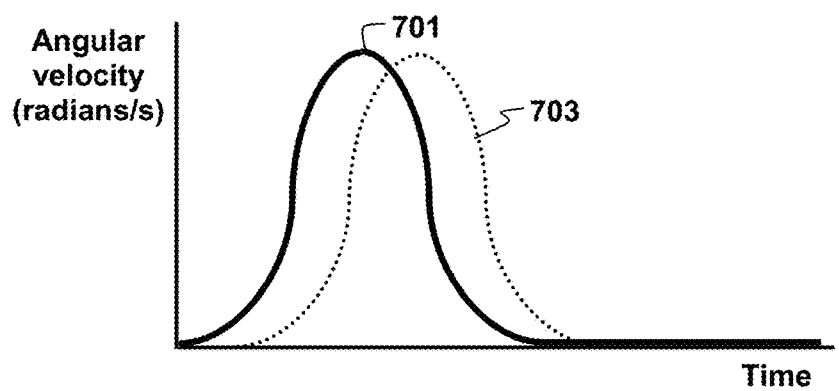
FIG. 9B shows how vestibulo-ocular phase is measurement.
Figure 9C:
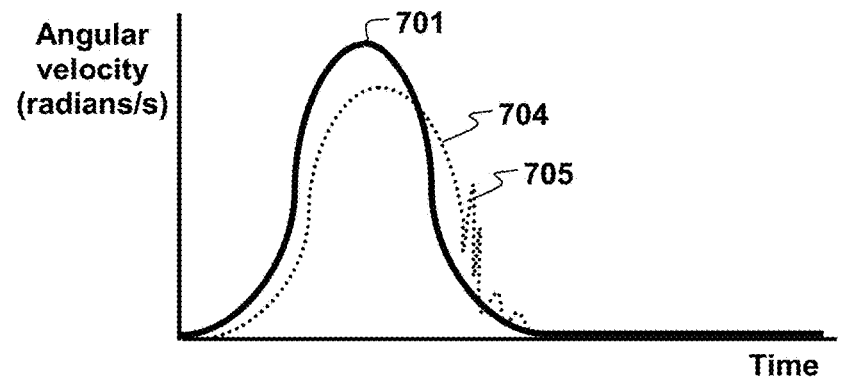
FIG. 9C shows ocular saccades.

FIG. 9A, FIG. 9B, and FIG. 9C provide graphs of time versus angular velocity that show how ocular response to a vestibular input can be measured. In these figures, the input is a rotation of the head, which is shown as the solid line at 701. This head rotation information would typically be measured using the head orientation sensor 108 that has been shown in FIG. 1, FIG. 2, and FIG. 5. The output is the eye response to the head rotation, which is shown as the dotted line at 702, 703, and 704, and would typically be measured using the eye sensor, which is typically an eye tracking digital video camera 110, such as that shown in FIG. 1. The actual eye response is in the direction opposite of the head rotation, 701, but it has been plotted in the same direction to make it easier to compare the input and output of a person's vestibulo-ocular system. In FIG. 9A, the velocity of the eyes is slower than that of the head, which results in a gain of less than 1.0. In FIG. 9B there is a delay between the rotation of the head and the rotation of the eyes, which results in a phase lag. In FIG. 9C, the eye rotation also lags the head rotation as shown at 704, but is caught up by saccades 704 near the end of the rotation.

Figure 10A:
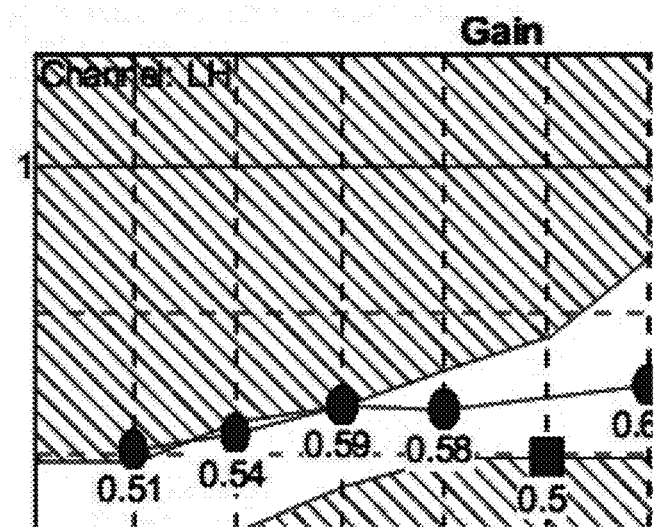
FIG. 10A illustrates an example of the left eye gain of a healthy person's vestibulo-ocular response to motion between 0.1 Hertz and 1.28 Hertz.
Figure 10B:
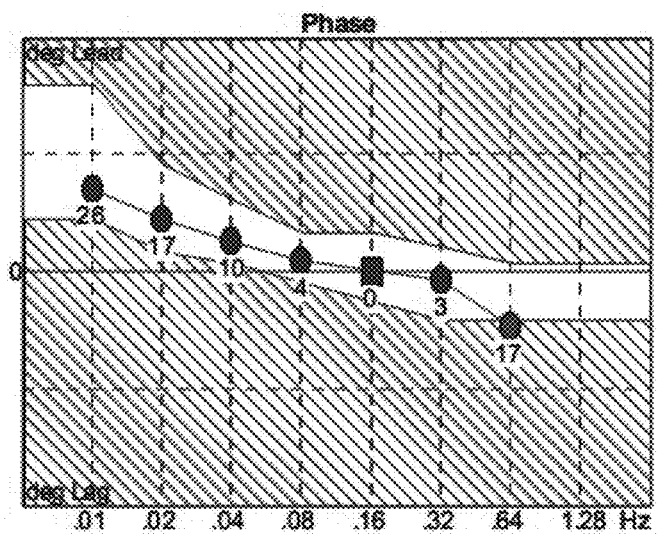
FIG. 10B illustrates an example of the phase lead and lag for a health healthy person's vestibulo-ocular response to motion between 0.1 Hertz and 1.28 Hertz.
Figure 10C:
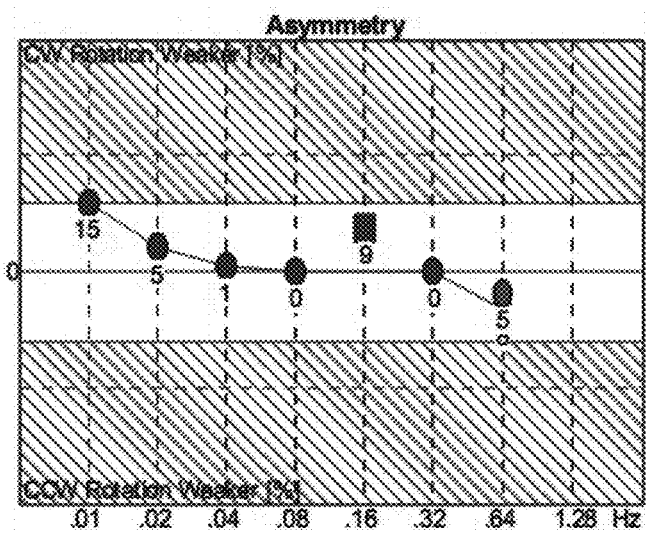
FIG. 10C illustrates an example of the asymmetry readings between counterclockwise and clockwise horizontal rotation of a healthy person's vestibulo-ocular response to motion between 0.1 Hertz and 1.28 Hertz.

The measures shown in FIG. 9A, FIG. 9B, and FIG. 9C, can be plotted at different frequencies and compared between the left eye and the right eye to create the plots shown in FIG. 10A, FIG. 10B, and FIG. 10C, which illustrate some typical eye responses to oscillation of a healthy person's head (e.g. vestibulo-ocular responses) in a horizontal plane at frequencies ranging from 0.1 Hertz (1 cycle every 10 seconds) to 1.28 Hertz (approximately 5 cycles every 4 seconds). More specifically, FIG. 10A shows the gain at these frequencies, FIG. 10B shows the phase lead and lag at these frequencies, and FIG. 10C shows the relative symmetry (or asymmetry) between clockwise and counter-clockwise oscillations. It should be noted that 0.1 Hertz to 1.28 Hertz is typical for the range of frequencies being used by prior art VOR testing systems. The embodiments described in this disclosure can include any frequency in the range of 0.01 Hertz (1 cycle every 100 seconds) to 15 Hertz (approximately 15 cycles every second).

FIG. 11A, FIG. 11B, FIG. 12, FIG. 13, FIG. 14, and FIG. 15 relate to targets or visual elements that could be presented on a VR or AR display to facilitate measurement and/or improve ocular performance parameters such as vestibulo-ocular function. These targets or visual elements can be designed to enhance the eye fixation on the displayed image when the head is motionless and the visual element is in motion. These targets or visual elements could also be designed for when the head is in motion and the visual element is motionless or when both the head and the visual element are in motion. In either VR or AR the displayed targets or visual elements can be static in a position or location or the displayed targets or visual elements can be dynamically changing in position, depending on the specific test being performed or rehabilitation method being used. The targets or visual elements, upon which the eyes are attempting to focus, can be of a variety of colors, sizes, shapes, and forms. They can change in color, size, shape, and form. They can contrast with other items being displayed to be more or less dominant in order to provide visual weight to enable fixation. These targets or visual elements can use specific colors with more saturation and can change in scale and proportion, all in an effort to draw the fovea toward a specific point of fixation on the target or visual element. With stereoscopic or 3-dimensional viewing, foveated rendering can also allow the image of interest to be seen in detail seen clearly and the remaining adjacent region is less detailed. Without using such enhancements to what is displayed, when performing VOR, DVA, or other ocular performance testing, the eyes tend to wander and have more microsaccades, which decrease the fixation ability and lessens the attentiveness of the person performing the test and the accuracy of testing. Generally, it is important to have some small point of focus to lessen the microsaccades and enhance the fixation ability. These same targets or visual elements can be used for any oculomotor or ocular performance testing including VOR re-training when a VOR abnormality exists.

The ideas expressed in the previous paragraph can best be explained by looking at some examples. FIG. 11A shows an example of a target or visual element in the form of a soccer ball 902. This soccer ball could be part of an existing scene viewed on a VR or AR display or viewed through an AR display or the soccer ball could have been added to the scene. The soccer ball could be spinning, which might make the pattern on the ball distracting. FIG. 11B shows the visual element (soccer ball) of FIG. 11A that has been altered by defocusing the ball 904 and superimposing a target in the form of a cross-hair 906 that is easier for the eyes to focus on. It would be easier for the eyes to focus on the element shown in FIG. 11B than the element shown in 11A due to the shape, size, contrast, and suppression of the pattern on the ball. Although this example has been done using a black and white image, color and color contrast can be more effective. For example, the visual element seen in the VR or AR platform display could be a red colored ball and within the center of the ball a dark cross-hair surrounded by a lighter yellow circle could be placed. This strongly contrasted central focal point could help the eye focus on a specific point and lessen the "eye scanning" while undergoing any ocular performance measurement such as VOR testing or VOR re-training. In another example, the element being viewed can be in the shape of a familiar object, such as a basketball, football, helmet or object used in one's occupation. It can also have a centered focal point, created by high contrast and high color saturation compared to the surrounding background to maintain the foveal fixation duration attractiveness and lessen microsaccades.

FIG. 12 shows a scene that can be used for optokinetic testing in a virtual or augmented environment. In traditional optokinetic testing, a person's head is motionless while seated inside a moving drum with alternating black and white vertical lines or alternatively, a hand-held drum, with alternating black and white vertical lines, is placed in front of the person. The drum is slowly rotated. The alternating lines induce nystagmus and cause visually induced motion sickness. The movement of the eyes is measured as the drum rotates left and then right. Measurements can be at different drum speeds. This same test can be performed using an AR or VR platform by creating a visual image that includes elements that work just like the vertical lines in the drum. Examples of natural scenes that are similar to the drum with lines can include examples such as being seated in a car and watching a train go by or driving and watching the telephone poles move by, such as the scene 910 shown in FIG. 12. Similarly flying objects can be visualized as moving across the visual field or along another plane of motion beside the person. These visual elements can also change in size, color or other dimensions, as the person gets closer to the virtual object or further from the visual element. Motion can occur in any direction relative to the person, as the eye movement is being assessed and measured.

Figure 13:
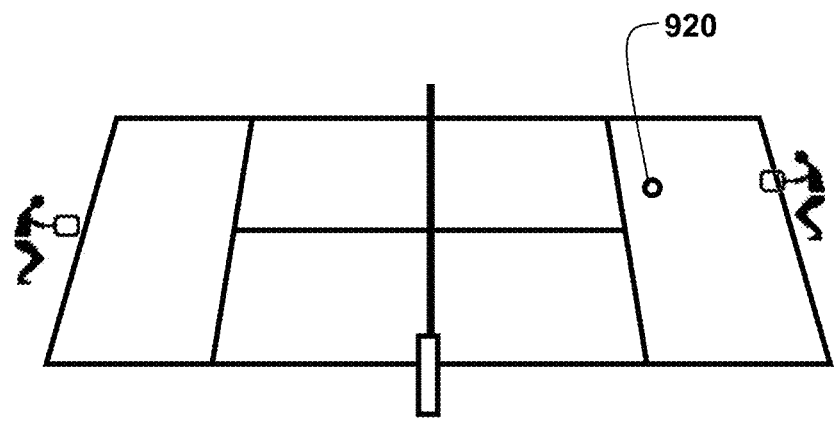
FIG. 13 shows a scene that can be used for testing eye-tracking performance.
Figure 14:
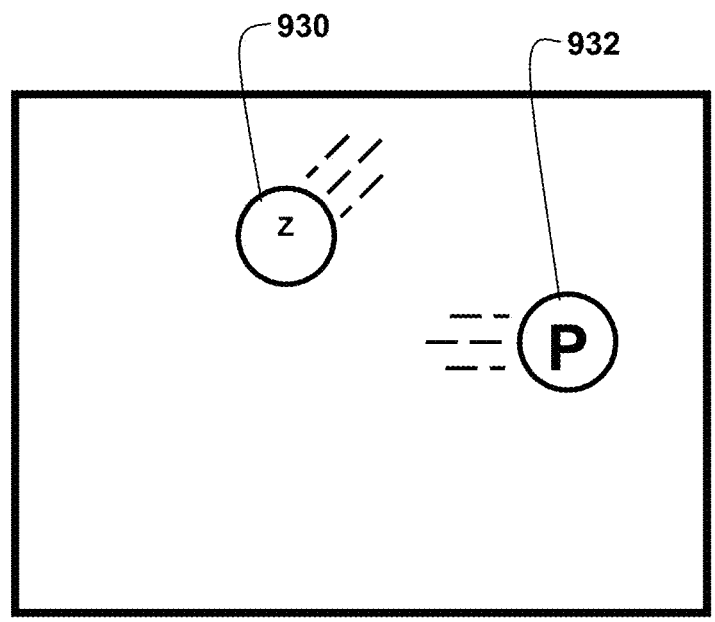
FIG. 14 shows a scene that can be used for dynamic visual acuity testing.
Figure 15:
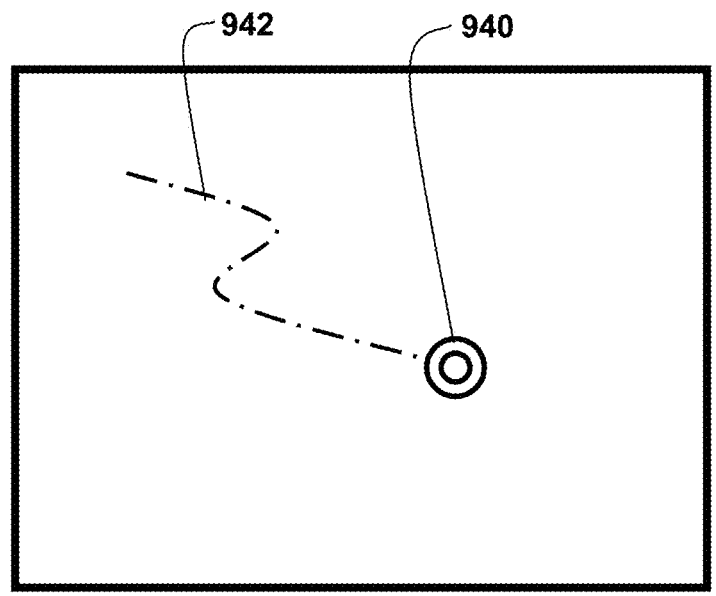
FIG. 15 shows a scene that can be used for scan path tracking.

FIG. 13, FIG. 14, and FIG. 15 illustrate other AR/VR/synthetic 3D display scenes that can be used for ocular performance testing such as VOR, DVA, visual pursuit, and/or fixation ability testing. These scenes can include a test environment comprising natural background features combined with a visual element or target whose shape, color, size, motion, or other attributes have been selected or added to facilitate testing of vestibulo-ocular performance. FIG. 13 shows an example of a scene which illustrates what this type of ocular performance testing, such as with visual pursuit, DVA and/or VOR might look like. In the example shown in FIG. 13, the static scene can be a tennis court and the moving target is the tennis ball 920. The visual element (e.g. tennis) can remain motionless in the center, surrounded by a static court with 2 players on each side. The individual being tested would rotate his/her head in the horizontal and vertical plane while focusing on the visual element. Alternatively, as the person focuses on the static visual element in front of the player on one side of the court, it can suddenly become dimmed and re-appear on the other side of the court. The individual being tested is required to rotate the head each time the visual element reappears. This action can occur in a back and forth manner until the measurement is complete. For more complex testing, the surrounding courtside scene can be filled with fans who are in motion. For As another example, if the VOR is being tested on a basketball player, the dynamic background features may be a basketball court surrounded by fans, who are yelling and moving and the visual element (e.g. basketball) may suddenly appear in the hands of a player on one side, then dimmed and then alternatively appear in the hands of another player on the other side, requiring the individual being tested to move the head in a horizontal manner. Visual pursuit can also be virtually measured using the basketball as the visual element to be tracked as it is in motion from player to player and being thrown upwards to the basketball hoop. This can be a more realistic method of assessing ocular performance with VOR and visual pursuit measurement. DVA measurement can also be performed with dynamic changes of the target or visual element of interest, requiring the person to identify characteristics of the element while it is in motion and the person is in motion and comparing this to the SVA prior to the onset of the DVA test. FIG. 14 shows letters that could be superimposed onto the moving element (such as the tennis ball in FIG. 13) to test DVA. The target visual element 920 in FIG. 13, 930 and 932 in FIG. 14, or 940 in FIG. 15 could move in different trajectories, the letters could be of different sizes, and the ball could move at different speeds and accelerations to provide a meaningful test as shown by comparing visual element 930 with visual element 932. The targets can be static or rapidly moving is a specific plane or scan path for (such as watching a tennis ball move across the court or with tracking tests that have a rotating target visual element) depending on the ocular parameter being tested.

DVA testing could be performed with lettered optotypes and as the head rotates back and forth, the letters can rotate in position. Alternatively, numbers can be used as well as other familiar images of objects. The images can also be native or natural to the background environment displayed. As the head rotates back and forth, the target or visual element is more difficult to visualize. If there is a VOR abnormality, for example the eyes will not be able to focus on the target or visual element of interest and will subsequently have less fixation and more errors in identifying a visual element. Measurement can also be performed with the visual element stationary and the head in motion or both the visual element and head in motion, which would be more realistic with everyday experiences. Static visual testing (SVT) can be performed to obtain a normal visual test. The visual acuity can be obtained, while the head and the visual element, or optotype being displayed are both motionless. Similar to a standard eye exam, an AR/VR platform can enable a person's static visual acuity (SVA), a component of DVA testing, by asking a person to identify a multitude of images or optotypes (letters, symbols, characters, figures of different sizes, shapes, orientation) on the visual screen.

Visual pursuit testing can be performed with similar targets or visual elements of interest as have been described previously. Smooth pursuit testing has traditionally been performed with the head motionless and the eyes following a moving light or finger moving across a visual field. FIG. 15 shows a scene that can be used for scan path tracking in a virtual or augmented environment. An enhanced target visual element 940 can be sent across the scene along a specific path 942, while the measured eye movement follows the visual element. The path of these visual images or elements can assume any pattern, such as a zigzag, a saw toothed, or a square wave, or have a scan path that is snake-like, curved, circular, sinusoidal or rotational to provide a realistic and natural method of assessment of visual pursuit.

Figure 16:
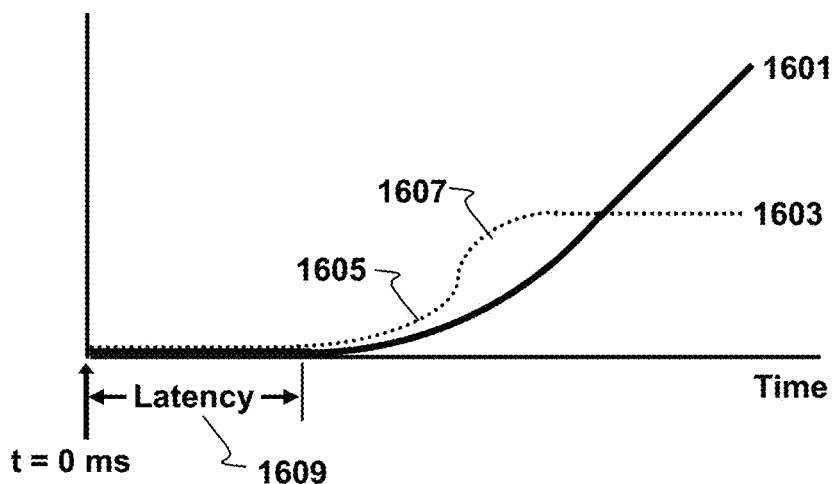
FIG. 16 shows the relationship between target movement, eye position, eye velocity, and eye acceleration for smooth pursuit.

FIG. 16 shows the relationship between target movement, eye position 1601, eye velocity 1603, and eye acceleration for smooth pursuit. The time when the target is moved is identified as t=0 ms. The eye position 1601 and eye velocity 1603 can then be tracked as a function of time. Latency 1609 is the delay from the time the target moves to the time the eye starts to move. Then the eye velocity 1603 will first accelerate 1605 and decelerate 1607 until the eye velocity 1603 matches the target velocity.

Figure 17A:
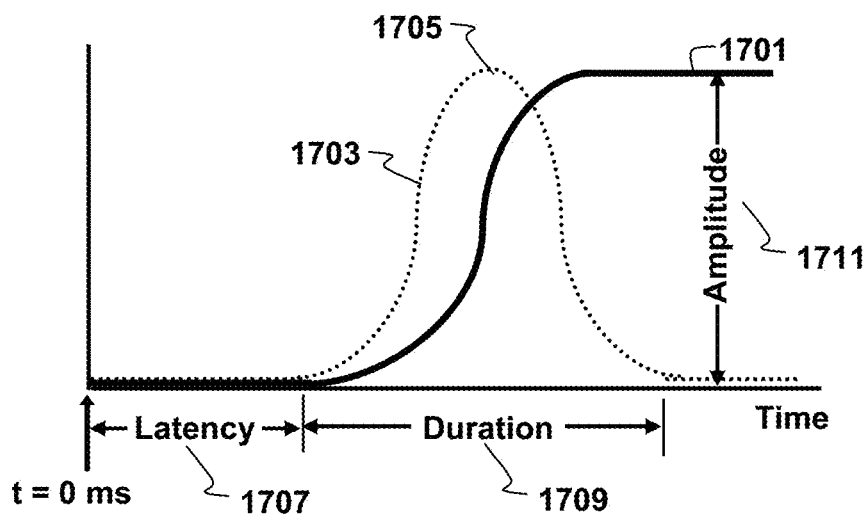
FIG. 17A shows the relationship between target movement, eye position, and eye velocity for a saccade.
Figure 17B:
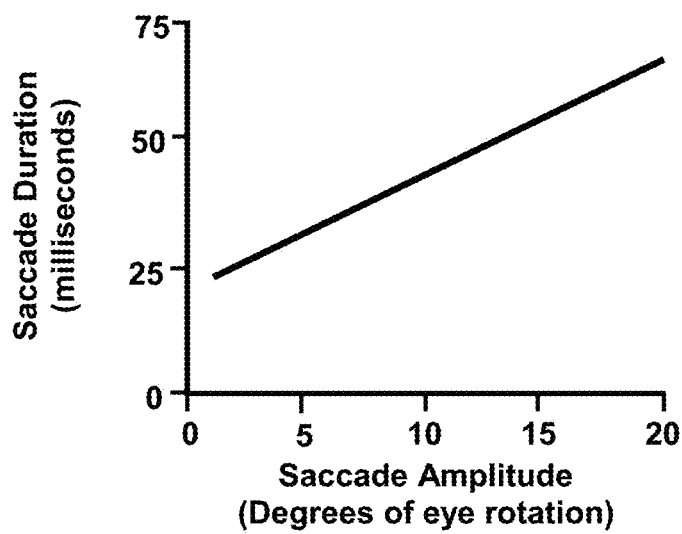
FIG. 17B shows the typical relationship between saccade amplitude and saccade duration.

FIG. 17A shows the relationship between target movement, eye position 1701, and eye velocity 1703 for a saccade. The time when the target is moved is identified as t=0 ms. The eye position 1701 and eye velocity 1703 can then be tracked as a function of time. Latency 1707 is the delay from the time the target moves to the time the onset of a saccade. As shown, the saccade eye velocity 1703 increases, reaches a peak velocity 1705, and then returns to zero. The length of time from the start to the end of this velocity curve is called the saccade duration 1709. The saccade eye position 1701 changes during this duration 1709 to reach a new position that differs from the initial eye position by a distance that can be defined as a saccade amplitude 1711. FIG. 17B shows the typical relationship between saccade amplitude and saccade duration.

Note that any of the testing described for any of these embodiments can be done with static targets or visual elements being viewed, or with dynamic targets or elements. The images or elements viewed may be familiar objects, such as balls, or objects more familiar to one's occupation. The visual target or visual elements may be displayed in a manner that is native or natural to the background.

Figure 18:
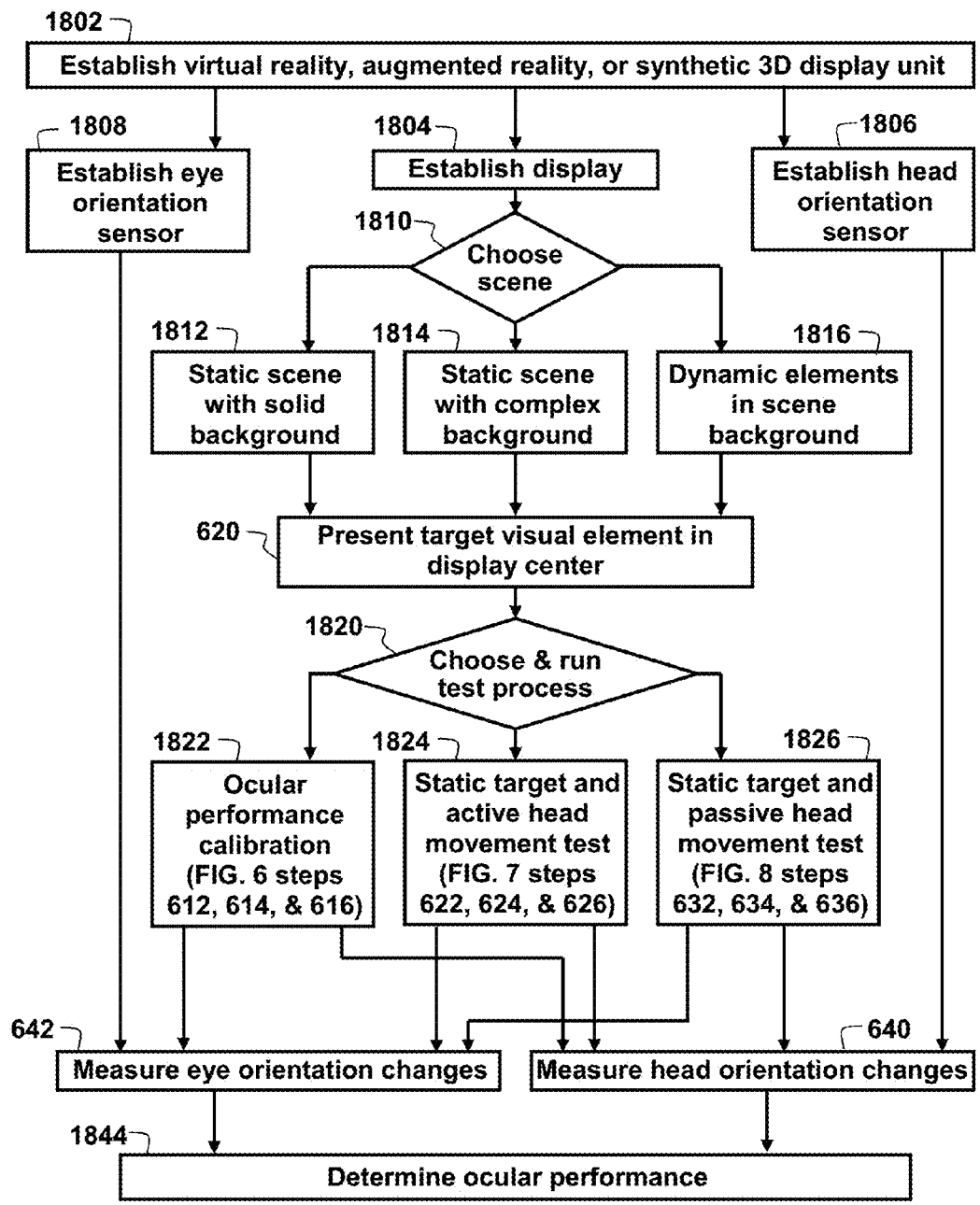
FIG. 18 shows a generalized method for ocular testing using virtual reality, augmented reality, or a synthetic 3-dimensional scene on a display.

FIG. 18 provides a more generalized embodiment of the system and method that was presented in FIG. 6, FIG. 7, and FIG. 8. Referring to FIG. 18, the head-worn virtual reality or augmented reality unit that was shown at 602 in FIG. 6, FIG. 7, and FIG. 8, can more generally also be a synthetic computer-generated 3D display unit and it does not necessarily need to be head-worn. Thus, it could be a VR/AR, or synthetic 3D display unit, as shown at 1802 in FIG. 18. The eye tracking video camera on the unit that was shown at 608 in FIG. 6, FIG. 7, and FIG. 8 can more generally be an eye orientation sensor and it does not need to be mounted as part of the unit. Thus, it could be simply an eye orientation sensor, as shown at 1808. Similarly, the display 604 and head orientation sensor 606 that were shown in FIG. 6, FIG. 7, and FIG. 8 do not necessarily need to be on the unit. They could be located somewhere else as shown at 1804 and 1806 in FIG. 18. As shown in FIG. 18, the process can further include the step of choosing a scene 1810 and the choices of scenes can comprise a static scene with a solid background 1812, a static scene with a complex background 1814, and/or scene with dynamic (i.e. moving) elements in the background 1816. The process shown in FIG. 18 includes the step of presenting a target visual element in the display center 620, just like the processes shown in FIG. 6, FIG. 7, and FIG. 8.

Further referring to FIG. 18, the method can comprise the step of choosing which ocular test to run on a subject as shown at 1820, and the choices can include ocular performance calibration 1822, static target and active head movement testing 1824, and/or static target and passive head movement testing 1826. Each of these three test processes (1822, 1824, and 1826) involves measuring eye orientation changes 642 and head orientation changes 640, just like the processes shown in FIG. 6, FIG. 7, and FIG. 8. The output of the process illustrated in FIG. 18 can more broadly (than FIG. 6, FIG. 7, and FIG. 8) comprise any ocular performance parameter. These ocular performance parameters can include any of the following parameters that have been discussed in other parts of this disclosure, including but not limited to:

(a) vestibulo-ocular reflex;
(b) saccades;
(c) pursuit tracking during visual pursuit;
(d) nystagmus;
(e) vergence;
(f) eyelid closure;
(g) dynamic visual acuity;
(h) dynamic visual stability;
(i) retinal image stability;
(j) foveal fixation stability; and
(k) focused position of the eyes.

In an alternate embodiment to the configuration shown in step 1824 in FIG. 18, the visual target of interest can be dynamic and the head movement can also be dynamically moving in the same direction as the visual target movement. The process is repeated as many times as needed. This test can be conducted in the vertical, horizontal or any other direction.

Figure 19:
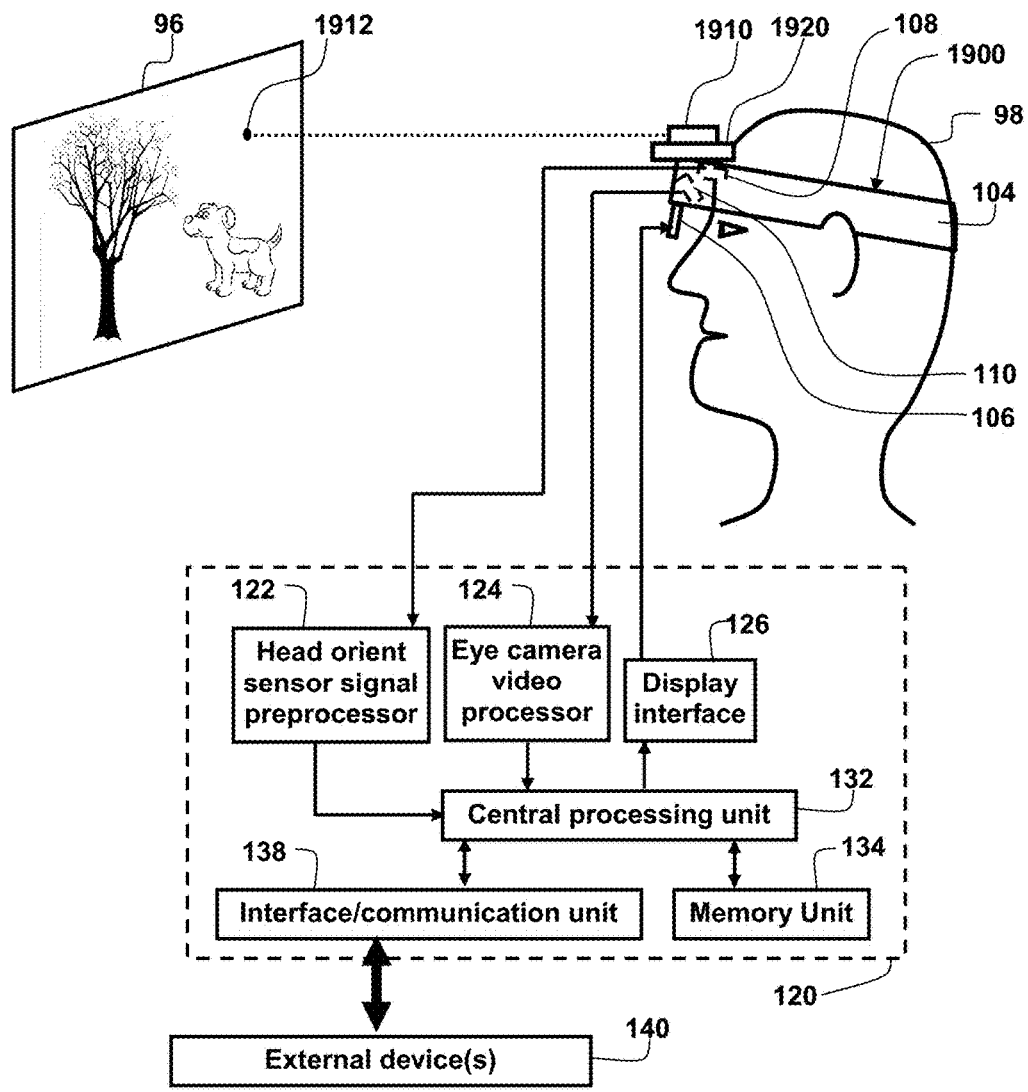
FIG. 19 shows an embodiment similar to that shown in FIG. 1 and FIG. 2, that further comprises a forward-facing camera and a light beam projector.

FIG. 19 shows an augmented reality system, similar to the embodiments described with reference to FIG. 1 and FIG. 2. The system shown in FIG. 19 can be used for ocular performance tests as described in other parts of this document. FIG. 19 also shows a scene 96 that is visible to the user 98. The scene example 96 shows a tree and a dog. The scene 96 can be blank. The scene 96 could be comprised exclusively of static images, such as the tree. The scene 96 could include dynamic (i.e. moving) images, such as the dog.

In addition to all of the items described with regard to FIG. 1, the embodiment of the augmented reality system 1900 shown in FIG. 19 also comprises a light beam projector, shown at 1910, and a forward-facing camera, shown at 1920. The light beam projector 1920 can be a laser pointer or any other source of a light that can be projected from the head-worn device into the user's field of view, as depicted by the scene 96. The projected light can produce a spot or shape in the user's field of view that can serve as a reference point, a projected object that the user can focus on, as shown at 1912. The reference point or projected object generated by the light beam projector 1912 can be used as a target that the user is asked to follow or focus on as part of an ocular performance test. This reference point or projected object 1912 can be in addition to any information presented by the AR display 106, or it can substitute for one or more of the functions of the AR display 106. For clarity, no connection has been shown between the light beam projector 1920 and the electronic module 120. However, it should be clear to anyone who understands the art that the light beam projector 1920 could be responsive to communication from the electronic module 120. Signals from the electronic module could travel to the light beam projector via a wired or a wireless connection. Such signals could control light intensity, size, shape, color, location, and motion of the object 1912 generated by the light beam projector 1920, or any other parameter of the object capable of being understood by anyone skilled in the art.

The forward-facing camera 1920 can be configured to record an image of what the user is seeing. The forward-facing camera 1920 can be configured to adjust its field of view, focal length, or to zoom in or out in response to an eye sensor. The electronic module 120, using the central processing unit 132, could control the forward-facing camera 1920. This control of the forward-facing camera 1920 could be through wired or wireless electronic signals. The forward-facing camera 1920 could transmit video information to the electronic module 120 and this video information could analog or digital information and could be transmitted through a wired or a wireless connection. Any other component in the system shown at 1900 could also be controlled through the forward-facing camera. The information collected and/or recorded by the forward-facing camera 1920 could also be used, in conjunction with other information collected by the system 1900 for studies after the test on a user has been completed.

Figure 20:
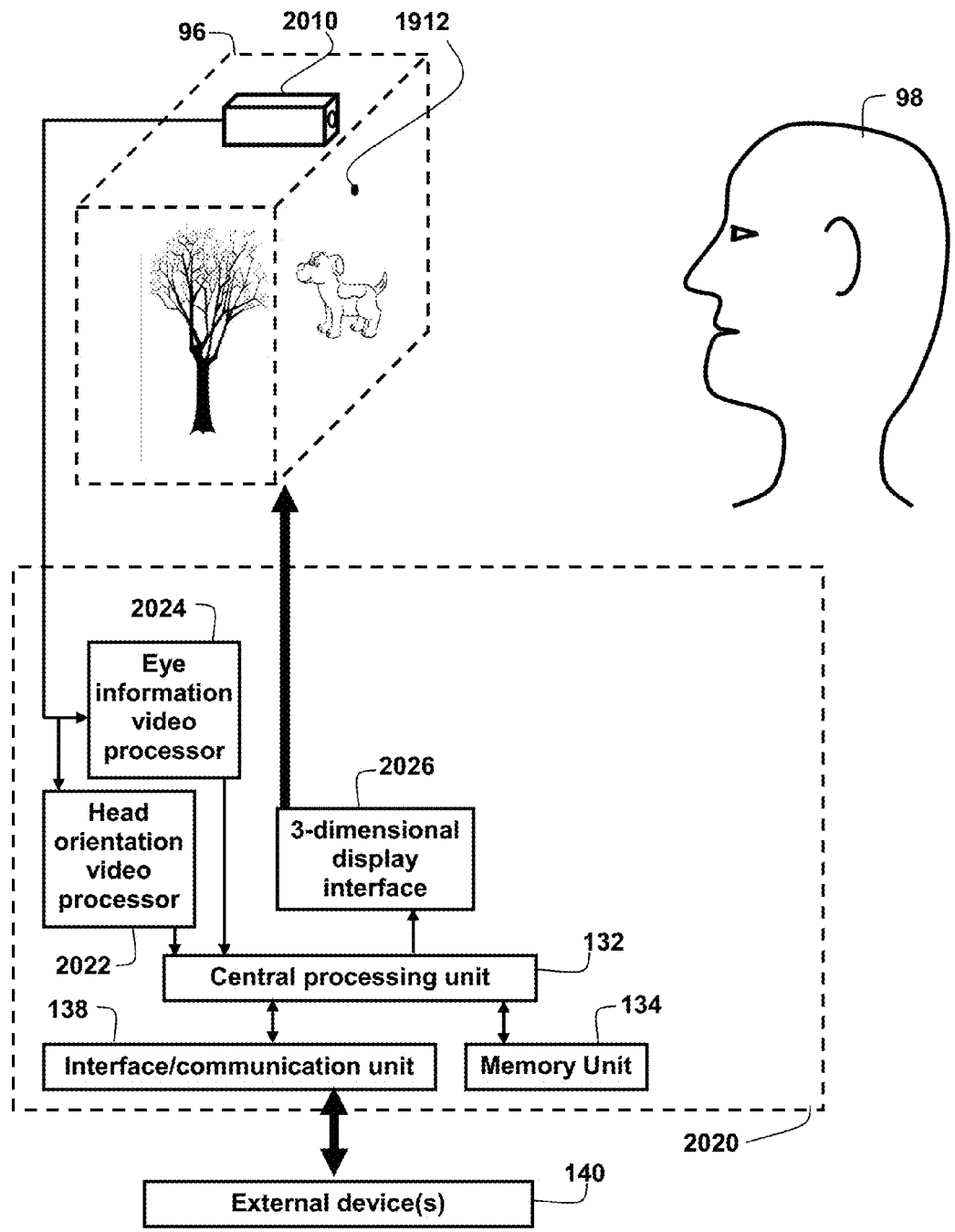
FIG. 20 shows an embodiment of a system similar to the ones described previously that requires no head-worn components.

FIG. 20 shows an embodiment of a system and method using AR/VR/3D simulation that is similar to the embodiments illustrated in FIGS. 1-19. In the embodiment shown in FIG. 20, the functions illustrated and described with reference to FIGS. 1-19 are performed without a head-worn device. In the embodiment shown in FIG. 20, the scene 96 is produced using an electronic module 2020 that comprises a 3-dimensional display interface (or device) 2026 for presenting the information. This 3D display interface/device 2026 could use any 3D display technology capable of being understood by anyone skilled in the art, including any of the 3D display technologies discussed in other parts of this document. Holography is one example of such a 3D display technology. Due to the realism available through the use of a 3D display device/technology, the person (or subject, or user) 98 feels that they are immersed in the scene 96. Non-user-worn eye tracking can be accomplished using any of the technologies discussed in other parts of this document. The use of a video camera located above the scene 2010 is one example of such an eye tracking technology. Non-user-worn head tracking could be accomplished using any of the technologies discussed in other parts of this document. The use of a video camera located above the scene 2010 is one example of such a head tracking technology. Note that in the embodiment shown in FIG. 20, the same video camera 2010 is used for both eye tracking and head tracking. This could also be accomplished using two separate cameras and any combination of any of the technologies discussed in this document. The video camera(s) 2010 could be connected to a video processor for eye orientation video processor 124 and a head orientation video processor 2022, both of which can be connected to a central processing unit 132 in the electronic module 2020. The visual object 1912 that can serve as a target, as described with reference to FIG. 19 can be generated as part of the scene 96. This target 1912 could be stationary (static) or it could be dynamic (moving). The electronic module 2020, through the display interface 2026, can control the target 1912. The electronic module 2020, comprising a central processing unit 132 and a memory unit 134, can also be used to record display information, head orientation information, and eye information to keep a record of a test for subsequent analysis. The system shown in FIG. 20 can further comprise an interface and/or communication unit 138 which can be configured to communicate with an external device or devices 140. Ocular performance measurements with the system shown in FIG. 20 can be done using any of the methods described in other parts of this document.

Further referring to FIG. 20, ocular performance can be measured using static or dynamic images projected in the display scene 96, either with the head motionless or moving. The 3-dimensional scene can comprise a solid unobtrusive background or a background resembling typical natural activity. Any of the visual targets or visual elements previously discussed can be applied to this configuration. The 3-dimensional background scene, provided by the 3D display, can be limited or fully immersive with images that extend around 360-degrees around the subject as well as above the subject in a full hemispherical or spherical configuration that surrounds the subject viewed images.

In one embodiment, the 3D image is generated using a hologram. The user has in his visual field a holographic scene, which as an example may resemble basketball court, occupied by other players and the stands are filled with fans. The holographic scene can be varied having static or dynamic features. The user's eye movements can be measured by the remote eye sensors 2010 while visually immersed within the scene. VOR testing, pursuit tracking and other ocular parameter measurements can be performed while seemingly involved in the play activity. This type of measurement can also be performed in other environments more familiar to the user (e.g. a football field, tennis court, military activity). Alternatively, in another similar embodiment, the user can be wearing a device comprised of an eye tracker, head tracker, forward facing camera and laser projector, while the human ocular performance is measured. A synthetic 3D display system can be used using holographic imaging or a volumetric display. In this embodiment, a light beam projector or a laser hologram can be used to project a target of interest or visual element into the 3-dimensional display scene. This target of interest can be an image of a white dot, or other enhanced visual target upon which the user can focus. The ocular performance can be measured similar to that previously described in FIGS. 6, 7, 8, and 18. The measured visual element being viewed can be projected from the laser projector while the user is seemingly immersed in the scene of the holographic imaging or a volumetric display. A forward-facing camera can be oriented to capture visual images of the user's surroundings, or activate a photo or video feature of the synthetic 3-D scene and determine the intended focal point of the use. This determined intended focal point can be measured and correlated with the fixation accuracy of the eye tracking sensors. The user can also perform a predetermined action with the his/her eye(s) by focusing on a specific image or orienting the eye in a specific manner as an input control.

3. Eye Tracking

To measure specific eye responses (such as VOR, DVS, or other ocular performance measures), both eye tracking and head tracking measurements are required. Eye tracking is the process of measuring either the point of gaze (where one is looking) or the motion of an eye relative to the head position. An eye tracker is a device for measuring eye positions and eye movement. Eye tracking and/or measurement can be done in many ways, examples of which include: (a) using a device such as a contact lens that is attached to the eye; (b) using a head worn device; (c) using a remote system; or (d) using a sensor attached to another part of the body, such as a hand-held device or a smart watch. The eye tracking and/or measurement can be done: (a) in a non-contact fashion with the use of a light source (invisible light, such as with the use of an infra-red camera or light, or visible light); by using a video camera or other sensor system designed to visually capture and record the eye movement activity; (c) with a marker or sensor on a contact lens; and/or (d) with a magnetic system such as one using magnetized contacts and an external detector. If one or more video cameras are to be used for eye tracking, it is desirable to have a sampling rate at least 30 frames per second (30 Hz) and preferably at least 50/60 Hz. Many video-based eye trackers have sample rate of at least 250, 350 or even 1000/1250 Hz. These higher sampling rates may be needed in order to capture fixation of eye movements or correctly measure other saccade dynamics. In embodiments of the present invention, the video camera contained in a smart phone or tablet device could be used as an eye tracker. Since the eyes are not located at the center of head rotation, any rotation of the head requires translation of the eye relative to visual targets. For targets at optical infinity, this translation does not require any compensatory movement. For near targets this translation becomes significant and compensatory eye movements are required for stable gaze and at close target distances. One must also compensate when measuring VOR and the compensation requires knowing the distance between the center of rotation and the visual target. The relative location of the center of rotation of the eye with respect to the head mounted head tracker receiver varies for each subject because of anatomical considerations.

If a light source is used for eye tracking and/or measurement, the light source is directed toward the eye or eyes and a camera tracks the reflection of the light source and visible ocular features such as the pupil features and/or cornea surface reflection(s). The information can then be analyzed to extract eye rotation and ultimately the direction of gaze from changes in reflections. Additional information such as blink frequency and changes in pupil diameter can also be detected by the eye tracker. The aggregated data can be stored and written to a file that is compatible with eye-tracking analysis software. Graphics can be generated to visualize such findings. Beyond the analysis of visual attention, stored eye data can be examined to measure the cognitive state or other information.

A camera can be used as a sensor for detecting light in high resolution. When tracking and/or measuring the eye activity or eye movement, such as the VOR, an IR or video camera may be used and can be comprised of a single camera system or a multiple camera system. The camera can be located on the framework of the head worn device or within the lens material, or in the contacts being worn. If using a hand-held device, the video camera can be located remotely in the device being held, mounted or worn elsewhere on the body. The camera control unit can be activated by such options as: an external wireless signal, a touch unit, rapid head movement or voice activation. The control unit can also be timer actuated, triggered by an eye blink for a defined period of time, or by placing the device on the head (e.g. putting on the head-worn unit). The eye tracking system can be mounted on a head worn device, on eyeglasses framework, or partially within the lens of eyeglass or contact lens on in a hand held mobile smart device, such as a smart phone, smart pad, or limb worn computer system.

The eye tracking and/or measuring system may include hardware such as an infrared camera and at least one infrared light source, a video tracking system and recorder. The infrared camera may be utilized by the eye tracking system to capture images of an eye of the wearer. The video images obtained by the infrared camera regarding the position of the eye of the wearer may help determine where the wearer may be looking within a field of view of the head mounted display used in the system. The infrared camera may include a visible light camera with sensing capabilities in the infrared wavelengths. Infrared light or radiation is a longer-wavelength radiation than visible light. It exists just outside of the spectrum of visible light. Heat, or thermal energy, is a common source of infrared light. An infrared camera is a device specially designed to detect and display the sources of this kind of light. A thermal infrared camera converts the heat detected into electrical signals, which are then projected in an image. Many types of night vision cameras are based on infrared light. A human body will always emit heat, and infrared cameras will detect this radiation.

The infrared light source can include one or more infrared light-emitting diodes or infrared laser diodes that may illuminate a viewing location, i.e. an eye of the wearer. Thus, one or both eyes of a wearer of the system may be illuminated by the infrared light source. The infrared light source may be positioned along an optical axis common to the infrared camera, and/or the infrared light source may be positioned elsewhere. The infrared light source may illuminate the viewing location continuously or may be turned on at discrete times.

The optical system may include components configured to provide images to a viewing location, i.e. an eye of the wearer. The components may include a display pane, a display light source, and optics, such as mirrors or refractive lenses. These components may be optically and/or electrically-coupled/connected to one another and may be configured to provide viewable images at a viewing location. One or two optical systems may be provided in the system. In other words, the head mounted display may allow the wearer to view images in one or both eyes, as provided by one or more optical systems. Also, the optical system(s) may include an opaque display and/or a see-through display connected to the display panel, which may allow a view of the real-world environment while providing superimposed virtual images. The infrared camera or video camera, using visible light, coupled to the eye tracking system may be integrated into the optical system with a data storage and logging recorder.

Video-based eye trackers typically use the corneal reflection (the first Purkinje image) and the center of the pupil as features to track over time. A more sensitive type of eye tracker, the Dual-Purkinje eye tracker uses reflections from the front of the cornea (first Purkinje image) and the back of the lens (fourth Purkinje image) as features to track. A still more sensitive method of tracking is to image features from inside the eye, such as the retinal blood vessels, and follow these features as the eye rotates.

Eye sensors to track reference locations on the surface of one or both eyes to determine gaze-tracking locations, utilizing multiple illumination sources and/or multiple cameras to generate and observe glint/reflections from multiple directions can be used improve the accuracy of gaze tracking. One or more of the illumination sources can be comprised of infrared, near infrared or visible light, such as an LED and OLED projector. Eye sensors can also obtain biometric information. Eye sensors can be used to obtain anatomic structures and features of the eye, movements of the eye and eyelids, responses and reflexes of the eyes and eyelids. Eye tracking data can also be collected using a multi-camera eye gaze tracker, which is based on one-camera gaze estimation algorithm. Using an algorithm, the 3D eyeball position can be estimated by the two corneal surface reflections (or glints) of the IR lights. Each camera can estimate the gaze independently and can allow large head movement. The accuracy of this system is less than 1 degree.

Eye tracking using binocular horizontal and vertical eye position estimates can be derived from the relative positions of multiple corneal reflections and the center of the pupil. By using two eye landmarks (corneal surface reflections and pupil center) whose relative position are invariant under translation, the angular position of the eye independently of lateral motion of the video system relative to the head is able to be estimated. The optical components can be mounted on an eyeglasses frame or goggles.

The light source can be infrared, near infrared, and/or visible light, such as LED, can be directed toward one or both eyes. The camera can be used to track the reflection of the light source and visible ocular features such as the pupil features, cornea reflection features, iris registration features, limbus features or retinal data imaging. The collected data from the eye tracking system can be used to measure the movement features of the eyes or eyelids or rotation of the eye, acceleration/velocity of the eye movement, duration of the eyelid closure, rate of the eyelid closure and the direction of gaze. Additional information such as blink frequency and changes in pupil diameter can also be detected by the eye tracker. Aggregated eye tracker data can be written to a file for later analysis. Stored eye tracker data can be used to analyze the visual path across an interface such as a computer screen. In this case, each eye data observation is translated into a set of pixel coordinates. From there, the presence or absence of collected eye data points in different screen areas can be examined. This type of analysis is used to determine which features are seen, when a particular feature captures attention, how quickly the eye moves, what content is overlooked and virtually any other gaze-related data. Eye position is extracted from video images and graphics are often generated to visualize such findings. Search based on an electro-oculogram may be used. When using a video-based eye tracker, the camera can be focused on one or both eyes and used to record eye movement as a viewer looks at some kind of stimulus.

A thin prism can be used between the eye and a camera system, which acts as a light-guide altering the imaging path between the camera and the eye. The use of a thin prism can also provide on-axis illumination. This arrangement can enable an eyeglass like eye tracking device, which captures a frontal (i.e., on-axis) or near frontal image of the eye to have a visually appealing form factor.

In other embodiment multiple prisms can be used which can use a corrective optical element to eliminate any deviation or aberrations in the see-though viewing path, such that a user of the device can comfortably see through the eye-tracker normally. For example, in one of it aspects, the invention may include a wedge prism having only planar surfaces. This prism acts as a light guide to supply illumination light to the eye, as well as providing imaging light to the camera from the illuminated eye. In this embodiment a complementary prism can be arranged with respect to the thin prism such that the two prisms appear to the eye as a plane-parallel plate, or as a weakly powered optic.

In an alternative embodiment, an eye-tracker can use a free-form prism between the eye and a sensor. The freeform prism includes one or more surfaces with optical power, which are used both for imaging of the eye onto the sensor, and for optical aberration control. In certain embodiments, the freeform prism is used in conjunction with, or exclusive of, additional focusing optics such as a camera outside of the prism.

The eye-imaging camera can be mounted on the arm of an eyeglass frame or on the framework around the lens and can capture the image of the eye through reflection off of the lens. In order to properly capture the eye image through reflection off of lens, there must be sufficient clearance between the user's face and the lens surface to avoid the obstruction of the eye image by user's face or the imaging optics.

Alternatively, the camera can be mounted on the glass frame under or over the eye, and directly image the eye. This requires a more robust frame design, which must move the camera far enough away from the face to avoid interference. In this system, the camera captures an eye image at a close distance and from a slanted direction (i.e., at an angle), which results the eye image suffering keystone distortion. This arrangement also presents optical performance challenges due to the large depth of field necessary to accommodate all possible eye positions.

A beam splitter in an eyeglass lens can be used, off of which an eye is imaged by a camera positioned out of a user's line of sight. A beam splitter is an optical device that separates a beam of light into two or more different beams of light. Beam splitters are available in various forms. These include cubes, pipes and plates. What happens with a beam splitter is that it accepts the input beam and then proceeds to divide the light depending on the specified requirements. The input beam could be polarized or non-polarized light. The most commonly used is the cube beam splitter although the plate beam splitter is typically used to produce lower cost non-polarized beam splitters. These typically provide a 50-50% split ratio. The reflected and transmitted light emerging from the beam splitters are at various angles, which often necessitates external mirrors to redirect the light. Embodiments of the present invention are directed to single prism beam splitters and compound beam splitters formed from combining one or more of the single prism beam splitters. The beam splitters can be configured to produce one or more split beams of light that emerge from the prism at angles other than 90° to one another. The prisms can be configured so that the light propagating through the prisms encounters one or more intermediate planar surfaces at various angles with respect to the path of the light. A certain number of the intermediate planar surfaces can be angled so that the light transmitted along a particular path undergoes total internal reflection (TIR) at these intermediate planar surfaces. A number of other intermediate planar surfaces can be positioned or angled so that the light transmitted along a particular path does not undergo TIR. As a result, one or more beams of light propagating through the prism can be selectively split off to emerge from the prism by selectively disposing fully reflective and partial mirrors on the intermediate planar surfaces where TIR does not take place. The coating layer of a beam splitter can be made in such a way that a percentage of the light entering the beam splitter through one side can be reflected while another percentage is transmitted.

In other embodiments of the present invention, two or more of the single prism beam splitters can be combined to form compound beam splitters that split a single beam of light into three or more different beams of light. A beam splitter can have an optical multi-layer thin film, formed by laminating numerous layers in sequence. The numerous laminated layers can each be comprised of having a different refractive index.

In another embodiment, the eye tracking system can include a camera visor that is positioned in front of the eye of a user. In another embodiment, an array of optical detection elements can be placed directly onto the surface of the eyeglass-like lens located in front of an eye.

When using an eye-tracking camera, two general types of eye tracking techniques can be used: Bright Pupil and Dark Pupil. The difference between these eye-tracking techniques is based on the location of the illumination source with respect to the optics. If the illumination is coaxial with the optical path, then the eye acts as a retro-reflector as the light reflects off the retina creating a bright pupil effect similar to red eye. If the illumination source is offset from the optical path, then the pupil appears dark because the retro-reflection from the retina is directed away from the camera. Bright Pupil tracking creates greater iris/pupil contrast allowing for more robust eye tracking with all iris pigmentation and greatly reduces interference caused by eyelashes and other obscuring features. It also allows for tracking in lighting conditions ranging from total darkness to very bright. But bright pupil techniques are not effective for tracking outdoors as extraneous IR sources interfere with monitoring. In embodiments of the present invention, eye tracking might typically use a sampling rate minimally of 20 Hz. Typical sampling frequencies can include 20/30/50/60 Hz, 240 Hz, 350 Hz, and 1000/1250 Hz. The higher sampling frequencies are needed to capture the detail of the very rapid eye movement during reading, or during studies of neurology.

Embodiments of the eye tracking system can track on the cornea or further in the eye, based on using light reflected by the eye. Whether using an external source or ambient light, some of the techniques for tracking the eye include: limbus tracking, pupil tracking, Purkinje image tracking, corneal and pupil reflection relationship, corneal reflection and eye image using an artificial neural network.

Regarding limbus tracking, the limbus is the boundary between the white sclera and the dark iris of the eye. Because the sclera is (normally) white and the iris is darker, this boundary can easily be optically detected and tracked. The limbus tracking technique is based on the position and shape of the limbus relative to the head. This means that either the head must be held still or the apparatus must be fixed to the user's head. Due to the occasional covering of the top and bottom of the limbus by the eyelids, it is more helpful for precise horizontal tracking only.

Regarding pupil tracking, this technique is similar to limbus tracking. The difference is that in pupil tracking the smaller boundary between the pupil and the iris is used instead of the boundary between the white sclera and the dark iris. Once again, the apparatus must be held completely still in relation to the head. The advantages of this technique over limbus tracking is that the pupil is far less covered by the eyelids than the limbus, and thus vertical tracking can be accomplished in more cases. Also, the border of the pupil is often sharper than that of the limbus, which yields a higher resolution. The disadvantage pupil tracking is that the difference in contrast is lower between the pupil and iris than between the iris and sclera, thus making border detection more difficult.

Regarding Purkinje image tracking, when (infrared) light is shone into the user's eye, several reflections occur on the boundaries of the lens and cornea. These reflections are called Purkinje images. The first Purkinje image is also called the glint, and this together with the reflection of light off the retina, the so-called bright-eye, can be video-recorded using an infrared sensitive camera as a very bright spot and a less bright disc, respectively. When the eye is panned horizontally or vertically, the relative positioning of the glint and the center of the bright-eye change accordingly, and the direction of gaze can be calculated from these relative positions. The problems associated with this technique are primarily those of getting a good view of the eye; lateral head movement can put the video image of the eye out of focus, or even make the image of the eye fall out of view of the camera. Due to the lack of contrast, the center of the iris can be tracked instead of the center of the pupil Regarding pupil and pupil reflection relationship tracking, eye trackers can combine a camera with an infra-red light source that illuminates the eye with bursts of invisible infra-red light. Some of this infra-red light disappears into the pupil (the dark opening in the center of the iris), and some of it bounces back off the iris (the colored part of the eye), the cornea (the clear part at the front of the eye), the eyelid or the surrounding skin. All these different areas reflect different amounts of infra-red light, which is picked up by the camera. By analyzing the reflections using "a lot of very fancy matrix math" it is then possible to work out where the eye is pointing. Because eyes move in tandem, this only needs to be done for one eye. The technique is able to cope with blinking, head movements, dim light, glasses and contact lenses.

Regarding the use of artificial neural networks (ANNs) for computation, this is of the more recently developed techniques. The raw material for eye-gaze tracking is still a digitized video image of the user, but this technique is based on a more wide-angled image of the user, so that the entire head is in the field of view of the camera. A stationary light is placed in front of the user, and the system starts by finding the right eye of the user by searching the video image for the reflection of this light-the glint, distinguished by being a small, very bright point surrounded by a darker region. It then extracts a smaller, rectangular part of the video image (typically only 40 by 15 pixels) centered at the glint, and feeds this to an ANN. The output of the ANN is a set of display coordinates. The ANN requires more than the simple calibration that is required by the other techniques; it must be trained by gathering images of the user's eye and head for at least three minutes while the user visually tracks a moving cursor on the display. This is followed by an automatic training session that uses the stored images lasting approximately 30 minutes using the current technology, but then the system should not require re-calibration on the next encounter. To improve the accuracy of an ANN-based system, the corneal/pupil based calculations can be augmented with a calculation based on the position of the glint in the eye socket. The great advantage of ANN-based techniques is that due to the wide angle of the base image, user head mobility is increased.

Eye movement information from the eye tracker can be typically divided into fixations and saccades, when the eye gaze pauses in a certain position, and when it moves to another position, respectively. The resulting series of fixations and saccades can be called a called a scan path. Most information from the eye can be made available during a fixation, but not during a saccade. The central one or two degrees of the visual angle (the fovea) can provide the bulk of visual information; the input from larger eccentricities (the periphery) is typically less informative and analysis algorithms can be structured accordingly. Hence, the locations of fixations along a scan path show what information loci on the stimulus are processed during an eye tracking session.

Scan paths are useful for analyzing cognitive intent, interest, and salience. Other biological factors (some as simple as gender) may affect the scan path as well. As a participant looks at a page on the internet, the eye-tracking device can focus on the pupil of the participant's eye and determine the direction and concentration of the participant's gaze. Heat maps represent where the visitor concentrated their gaze and how long they gazed at a given point. Generally, a color scale moving from blue to red indicates the duration of focus. Thus, a red spot over an area of your page might indicate that a participant, or group of participants, focused on this part of a page for a longer time. Saccade pathways trace the eye's movement between areas of focus. The movement is not unlike watching a hummingbird move between flowers—there are periods of attention and then rapid movement. A red circle may indicate the area of focus, while a red line indicates the flight.

Another capability of the eye tracking technology is eye movement analysis, which can provide valuable insight into users' overt visual behavior and attention. The most common method for determining the location of a user's observable visual attention is by identifying the fixations and saccades that best indicate where they are focusing on the stimulus in front of them.

A linear filter may be used when processing eye-tracking data to approximate eye movement signals, at least well enough to recognize a pattern. The salient eye movements that are typically identified by eye movement analysis are fixations, saccades, and smooth pursuits. Fixations are a result of one's desire to maintain gaze on a specific, stationary object. Smooth pursuits are similar except for the object of interest is in motion. Saccades represent a voluntary shift of focus from one fixation point to another.

Saccades can be detected and measured by two means as well: the position variance method and the velocity detection method. The position variance method identifies saccades as those moments in the signal in which the position of the eye changes rapidly. The velocity detection method uses an empirically determined velocity threshold. If the velocity of the signal is calculated as higher than the threshold, it is a saccade. Similarly, if it is below the threshold (as discussed above) it is a fixation. For both fixations and saccades, the velocity method is becoming more widely used because it is more suitable for real-time applications.

Beyond the analysis of visual attention, eye data can be examined to measure the cognitive state and workload of a person. Some techniques have been validated in multiple contexts as a reliable indicator of mental effort. Driving a car, reading a magazine, surfing the interne, searching the aisles of a grocery store, playing a video game, watching a movie or looking at pictures on your mobile device are such applications of eye tracking. With very few exceptions, anything with a visual component can be eye tracked. People use their eyes almost constantly, and understanding how the eyes are used has become an extremely important consideration.

In another embodiment, the use of sensors on a contact lens can also be used for eye tracking eye responses and specifically VOP measurement. Employing multiple sensors on a contact lens can be used for detecting eye movement and contact lens orientation. The contact lenses may also employ the use of markers or the lenses could be magnetized. A multi-sensor contact lens can be placed in one or both eyes of a user and can actively determine movement activities of the eye. These sensors can be located on the surface of the lens or within the lens material. In another embodiment, an eye blink for a defined time can trigger the measurement of eye movement or turn on the device to begin the calibration for measurement. It is to be appreciated that both eyes of a human user generally blink at the same time, and thus in various embodiments only one multi-sensor contact lens is needed to generate a command to a remote device. Components on or within a contact lens can be of a shape, size, opacity, and/or positioned so as not to obstruct vision through an opening of a pupil of an eye when worn. Control features of multi-sensor contact lens can include issuing commands, adjusting content presentation, activating or deactivating options or components, or any other suitable functions. The multi-sensor contact lens can include either on or within its substrate a control circuit that can be coupled wirelessly to the multiple sensors.

In another embodiment, the multi-sensor contact lens can also communicate via a wireless network to a remote device. The remote portable smart device can include a wearable device, such as a head worn device or smart watch, or a non-wearable device, such as a remote mobile computer device, like that of a mobile smart phone, smart pad, pc and the like. The multi-sensor contact lens can use various kinds of sensors and they can be integrated in various combinations. The power component can include any suitable power source that can manage, receive, generate, store, and/or distribute necessary electrical power for the operation of various components of multi-sensor contact lenses. For example, the power component can include but is not limited to a battery, a capacitor, a solar power source, radio frequency power source, electrochemical power source, temperature power source, or mechanically derived power source (e.g., MEMS system). In another example, the power component receives or generates power from one or more of the sensors. A transceiver can transmit and receive information to and from, or within multi-sensor contact lens. In some embodiments, the transceiver can include an RF (radio frequency) antenna. In further embodiments, the video eye camera/eye tracker can be controlled remotely and/or alternatively with eye movements or voice activation or haptically. A remote device can also be used to control visual image(s) and the test procedures in embodiments of the invention. The remote device could also be used to process the data from head orientation sensors and eye tracking sensors and convert this information into the desired visual data for review.

In embodiments of the present invention, saccades can be tested by positioning two widely spaced targets in front of the person and asking the person to look back and forth between the targets. The technology in an AR/VR platform can be used to calculate corrective saccades. This system for the person is configured to collect eye images of the person in excess of 60 Hz and configured to resolve eye movements smaller than at least 3 degrees of motion. Eye movement data can include at least one fixation target presented to the subject in a defined position and configured to yield a voluntary saccadic eye response from at least one eye of the person. The latency, amplitude, accuracy and velocity of each respective corrective saccade and latency totals and accuracy is calculated. This platform can calculate, and display secondary, and higher, corrective saccades. Calculating corrective saccade measurements from the eye data can include:

(a) the total number of corrective saccades associated with the subject's eye movement to each fixation;
(b) first corrective saccade latency;
(c) first corrective saccade amplitude;
(d) first corrective saccade accuracy;
(e) first corrective saccade velocity;
(f) ratio of first corrective saccade amplitude to main saccade amplitude associated with the subject's eye movement to each fixation target; and
(g) ratio of total of corrective saccade amplitudes to main saccade amplitude associated with the subject's eye movement to each fixation target presented to the subject.

The corrective saccade measurements can include measurements for a first corrective saccade and at least a second corrective saccade. The corrective saccade measurements for each corrective saccade can include the latency, amplitude, accuracy and velocity of each respective corrective saccade. During the initiation of a saccade, a high frame rate may be required to anticipate the landing zone of a saccade. This can be used, for example, to activate grammatical elements rapidly (i.e., without the need to even perceive the target element) and/or remove a target element from the display eliminate corrective saccades and/or allow a new target to be chosen more rapidly using the so-called "gap effect."

Virtually, dynamic visual acuity (DVA), and retinal image stability (RIS), and foveal visual stability (FVS) testing can be used to determine the condition of a person's vestibulo-ocular reflex function. A DVA assessment can also include identifying a series of images or optotypes but with the addition of a head movement along an axis at a minimum rotational rate, engaging the vestibular system. The displayed images may also be dynamically moving in any direction, and can be random in position, appearance and presentation. Specifically, the image or visual element to be identified can be seen coming from any direction, randomly or with a specified pattern of motion, and may have different shapes, features, colors, sizes, orientation, patterns, or identifying characteristics, in a specific plane of axis or in variable plane, which the person must identify while the head in motion or rotating. The person can then provide feedback regarding what they see via an on-screen gesture, keyboard, smart device (e.g. defined as an electronic device, generally connected to other devices or networks via different wireless protocols such as Bluetooth, NFC, Wi-Fi, 3G, etc., that can operate to some extent interactively and autonomously), eye or other physical response or by voice response. The comparison of the smallest image, visual image or optotypes correctly identified or the comparison of the correct numbers of images, visual elements or optotypes in both the DVA and SVA tests can determine if the person has a defect in his or her vestibulo-ocular reflex functions.

In embodiments of the present invention, VR or AR platforms can have the unique advantage of measuring smooth pursuit in any plane and in a variety of scan paths. As an example, eye tracking and visual or smooth pursuit can be done by visually observing a moving image traditionally in a horizontal or vertical plane or alternatively in a saw-tooth, sinusoidal, square-wave, snake-like, torsional, looped or other non-fixed plane of motion, which is more natural to what the normal person experiences in everyday life. Convergence movements can be evaluated by having the person fixate on an object as it is moved slowly towards a point right between the person's eyes. In addition, the eyes can be observed and measured at rest to see if there are any abnormalities such as spontaneous nystagmus, dysconjugate gaze (eyes not both fixated on the same point) or skew deviation (eyes move upward (hypertropia), but in opposite directions, all resulting in diplopia (double vision). All of these evaluations can be measured with VR or AR platforms In embodiments of the present invention, pupillometry tests can easily be observed in either a VR or AR system, as the pupil can be measured on each side with variation of the levels of light. Both eye movement and peripheral vision testing can easily be measured in VR or AR systems. Eye movement testing can also be called extra-ocular muscle function testing is an examination of the function of the eye muscles. These tests observe the movement of the eyes in six specific directions. Peripheral vision testing is also called visual field testing. Testing the visual fields consists of confrontation field testing, in which each eye is tested separately to assess the extent of the peripheral field. Target detail within the peripheral field-of-view can be altered without attracting attention. In a process known as "change blindness," it is also difficult to discern visual changes (that attract attention) if the changes are introduced slowly or at times when an observer is not looking.

In embodiments of the present invention, the VR/AR system can be configured to:

(a) collect eye images in excess of 60 Hz;
(b) resolve eye movements smaller than at least 3 degrees of motion;
(c) measure when a stimulus is presented to only one eye of the subject or both eyes;
(d) yield a pupil eye response from at least one eye of the person;
(e) measure pupils in each eye independently for the person's left and right eyes; and
(f) compare pupillometry measurements for the left and right eyes.

Another embodiment involves dynamic control of the frame rate (i.e., number of images acquired per unit of time) of the one or more cameras that view regions of one or both eyes. Camera frame rate is a major determinant of the ability to determine and measure rates and directions of movement (i.e., velocities) of objects within images of an eye. The muscles within the eye are capable of movements that are the most rapid of all muscles within the human body. Thus, increased camera frame rate can be critical in some cases to more accurately and robustly measure dynamic movements of an eye and/or its components. Modern cameras are capable of operating over a wide range of frame rates. Instantaneous frame rates can also be adjusted (i.e., governed by so-called "clock" circuitry) as frequently as on an image-by-image basis. Closely aligned with camera frame rate is the acquisition time required to collect each image. The maximum time a camera can take to acquire an image is the inverse of the frame rate (i.e., the total time of a frame=1/frame rate). However, modern-day digital cameras also have the ability to limit the time over which they detect photons during the image acquisition process. Limiting the time to acquire photons is known in the art as "electronic shuttering." Shuttering light (including infrared) collection times to very brief intervals (typically in the order of microseconds to milliseconds) "freezes" images, allowing a clearer view of moving objects since object edges are spread over fewer pixels. On the other hand, longer acquisition times allow the detection of more photons during each image, increasing the amplitude (i.e., intensity within each pixel) of camera images and generally increasing signal-to-noise ratios. Although micro-movements can be useful to infer some aspects of a user's state (see below), they can interfere with directional and distance measurements of smooth pursuit and voluntary saccades. Higher frame rates allow algorithmic approaches to compensate for micro-movements by removing oscillations/movements at such frequencies or other mathematical approaches such as averaging results. Brief acquisition times can also be used to reduce image blur associated with micro-movements. The key to accurately determining initial saccadic direction and speed is the acquisition of camera images at high frame rates (typically hundreds of frames per second). Several techniques are available to acquire a rapid sequence of images immediately following a saccadic launch: 1) Once a saccadic launch is detected when sampling at a lower frame rate, the camera is immediately switched to a higher frame rate. 2) Camera circuitry (only) can be constantly run at a high frame rate, storing images within a circular buffer. Not all images are transferred out of the camera buffer and processed during normal operations. When a saccade is detected, rapidly sampled images that had been stored in the camera buffer can be retrieved for processing. 3) Frame rate can be adjusted based on the "context" of eye signal control. High frame rates can be maintained throughout these sequences.

Using an AR or VR display, one or more alphanumeric characters, halos, cursors, arrows, or other symbols may be superimposed within the display onto or adjacent to a particular object. These superimposed images or visual elements may indicate a particular meaning to the device user and this meaning may be assigned to the object so that it can be included in the eye signal language (in the same general manner as virtual icons). As examples, a halo can be placed around a physical light switch such that it can be the object of an action (e.g., turn on) or the name of a person can be displayed adjacent to the person's (real) face, allowing text or mail to be sent to that person using the eye signal language. Target or visual element fixation and image gaze data may be used within a gaze-based user interface enabled by an interaction model used with augmented reality or virtual reality. Such a user interface may also be multimodal incorporating head movement, hand movement, voice, and other physical or measurable brain-generated signals.

In further embodiments, any one of the tests, images, or visual elements described can also be visualized in a wearable display that includes a substrate guided optical device, known as the light-guide optical element system. Such a display can be a three-dimensional display. The display can be made up of an array of many small curved mirrors. Light could be delivered to that array via optical fiber. Each of the tiny mirrors could reflect some of that light to create the light field for a particular point in 3-D space, as a waveguide reflector array projector. The array could be semi-transparent to allow a person to see the real world at the same time. Multiple layers of such tiny mirrors would allow the display to produce the illusion of virtual objects at different distances. Planar wave guides or layers can be stacked to create a multifocal display in which each 2D planar wave guide, layer, column or set provides optical paths independently of other 2D planar wave guides, layers, columns or sets, allowing each to provide a respective focal or depth plane in a 3D image. This can include a series of linear or rectangular cylindrical wave guides arranged in vertical (xy) columns to create a planar 2D wave guide. This can include multiple 2D planar wave guides, columns, layers or sets, each corresponding to a different virtual depth plane. In such an embodiment using a partially transparent wave guide reflector array projector apparatus, a multiple depth plane three dimensional (3D) display system can visually provide multiple virtual depth planes at respective radial focal distances to simulate a 4D light beam field. The array of curved micro-reflectors can be oriented and positioned to project virtual images or visual elements at specified radial distances. The curved micro-reflectors typically partially reflect and partially pass electromagnetic energy, for instance optical wavelengths of light. The micro-reflectors can have one or more surface curvatures, and the surface curvatures may vary in each wave guide layer and the array can convert an input light beam from beam splitters into a stack of two-dimensional projections of virtual depth planes that recreates a three-dimensional volume on a display.

Embodiments of the invention can use miniature video cameras. The image of the eye can be tracked and allow the person's horizontal, vertical, and/or torsional (rotary) vestibulo-ocular responses to be measured. A moving visual target or visual element can provide a method for tracking, for optokinetic (OPK) testing, for saccade detection and measurement, for gaze fixation testing, for DVA measurement and for VOR testing. In the traditional Active Head Rotation (AHR) horizontal test, the subject moves their head left and right randomly to the auditory signal and visual presentation. The speed of the signals increases through 1 Hz up to a maximum of at least 5 Hz. The person will attempt to keep moving the head back and forth at the speed of the beeps. For AHR Vertical, this test is conducted in the same manner as the horizontal test above, except that the head motion is up and down rather than left and right In further embodiments, the VR/AR system can include a head mounted system with at least one, and typically two, digital camera(s) trained on the person's eyes and which the cameral can have auto-tracking. Each camera can be connected to and/or powered by a computer, such as through a "firewire" type connection. The computer may be a laptop portable computer or other digital device. The digital cameras may allow for digital centering of the person's pupil at least in one direction through concentrating on the region of interest, and can be in multiple directions. The use of digital centering eliminates the need for a mechanical adjustment mechanism in the given direction.

In another embodiment, the eye sensor can be further configured to capture a 3D image of the iris. In another embodiment, the eye sensor can be comprised of an array of transparent light detectors based on graphene. In another embodiment, the system can include an illuminator that is configured to provide illumination in a visible, LED or infrared light spectral band for the eye sensor to capture the 3D image of the iris. In further embodiments, the eye sensor can be a microlens array light field camera (LFC) or plenoptic camera. Holograms can be used to blend the digital world with the real world in the AR systems (to aid in the testing and measurement of the eye movement, acquire more immersive ways to be engaged in activity desired, and provide ways to teach, train, learn, explore, collaborate and create). This can enable a more immersive see-through multi-dimensional method for all of the visual or oculomotor tests described in this disclosure.

Embodiments of the present invention can comprise existing wearable display devices such as: (a) the VR devices manufactured by Sony, Samsung, Oculus, Carl Zeiss; (b) head mounted displays (HMDs) such as those produced by Google (e.g., Google Glass®) and Vuzix; and (c) augmented reality (AR) displays such as those manufactured by Microsoft, Vuzix, and DigiLens. Eye tracking sensors, such as digital video cameras, can be used to view such displays and to determine eye position information. Head tracking accelerometers are already commonly embedded within wearable devices of the type described herein. Acceleration and orientation relative to the earth's gravitational field based on the output of a head-mounted multi-axial accelerometer can provide information about relative head movements. When coupled with eye gaze direction and the tracking of vestibulo-ocular eye movements, absolute head position and movements referenced to viewed objects can be discerned. Within a wearable display system object position, direction, distance, speed and acceleration can be plotted. These display devices, with eye and head tracking sensors, provide a method to integrate head gestures with eye-signal control.

In embodiments of the present invention, eye movements, responses or reflexes and head movements can be detected and measured in a manner using VR and/or AR platforms, that are novel and unique compared to what has been done traditionally in the clinical laboratory. These embodiments enable a higher level of testing and measurement for these eye responses, particularly for the VOR and DVA. Embodiments of the present invention also provide unique methods to rehabilitate persons with vestibular system disorders, particularly those with peripheral vestibular disorders and especially those persons with vestibulo-ocular reflex abnormalities and/or abnormalities of the dynamic visual acuity.

In another embodiment, the images or visual elements presented for VOP tests (which can include DVA or other oculomotor measurements) can correspond to a plurality of depth planes provided to a viewer in the VR or AR display. The target image or visualized element may be different for each depth plane, which can provide a slightly different presentation of a scene or object. The target or visual element may be separately focused by each of the viewer's eyes, to provide depth cues based on the accommodation of the eye required to bring into focus different image features for the scene located on different depth plane and/or based on observing different image features on different depth planes being out of focus. These depth cues can provide credible perceptions of depth and add complexity to the testing and measurement.

4. Image Projection

Eye tracking, video recording, and specifically VOP measurement can be performed using a virtual retinal display or holograph imaging in another embodiment. A virtual retinal display (VRD), also known as a retinal scan display (RSD) or retinal projector (RP), is a display technology that draws a raster display, or bitmap, directly onto the retina of the eye. The user sees what appears to be a conventional display floating in space in front of them. However, the portion of the visual area where imagery appears must still intersect with optical elements of the display system. It is not possible to display an image over a solid angle from a point source unless the projection system can bypass the lenses within the eye. In a conventional display a real image is produced. The real image is either viewed directly or, as in the case with most head-mounted displays, projected through an optical system and the resulting virtual image or visual element is viewed. The projection moves the virtual image or visual element to a distance that allows the eye to focus comfortably. No real image is ever produced with the VRD. Rather, an image is formed directly on the retina of the user's eye. Eye movement and head inertial tracking can be measured while being connected to a virtual display system. The measurements can also be triggered with an external "microcontroller". Not only can VOR testing and DVA measurement be done with the virtual display, but it can also be used for other "immersive testing", sport training, military training, commercial medical education or teaching.

Therefore, in an alternate embodiment, the camera can track the eye movement and measure the VOR using synthetic 3D displays such as holographs or augmented reality display imaging.

Although the VRD is an output device, the technology lends itself to augmentation with eye tracking or eye gaze systems for input. The VRD system scanning light into only one eye allows images to be laid over one's view of real objects. The VRD system also can show an image in each eye with an enough angle difference to simulate three-dimensional scenes with high fidelity. The eye tracking can enable the fovea on the retina to always maintain good focus ability and as the pupil changes position, eye tracking with movement of the eye follows. As the eyes move, the foveation point can also change to achieve better tracking. Using a refractive lens can be used to prevent distortion of eye tracking. The fovea centralis, also generally known as the fovea is a part of the eye, located in the center of the macula region of the retina. The fovea is responsible for sharp central vision (also called foveal vision), which is necessary in humans for activities where visual detail is of primary importance.

In another embodiment low-persistence-of-vision display can enable a user to see images at only 24 frames per second. Even though the images flash by repeatedly, the mind fills in the blanks and the user will see (relatively) smooth motion. By reducing the amount of information the user sees, the brain can smooth out virtual reality. A head attached tracker (also known as an orientation sensor), with an adjustable sample rate, but minimally 20 Hz, and with tracker latency can be used to enhance virtual reality's realism on response time. Using a combination of 3-axis gyros, accelerometers, and magnetometers, can make it capable of absolute (relative to earth) head orientation tracking without drift. Each display to the eye can be adjusted with interchangeable lenses that allow for dioptric correction and adjustments for inter-pupillary distance requirements can be done. The mounted head tracker, when used with the eye worn virtual display can move the images to match the user's head movements, and create a greater sense of being inside a high definition LCD, LED or 1080 p OLED 3D (3 dimensional) images being displayed. A wireless interface can be used for sending the collected tracking data to a remote device. Hand held micro-controllers can also be used to manipulate the displayed images and obtain more of an immersive testing, training or rehabilitation experience.

In another embodiment, a different medium platform can be used to project the visual data for measurement of VOP, using a 3D (3 dimensional) virtual retinal display. In this embodiment, the virtual projection imaging device has no screen but can project images directly to the user's eyes. This screen-less display with the image displayed directly to the retina can also use a multiple micro-mirror design and low power light source. The image display quality can display a separate WXGA resolution (1,280×768) image directly onto the retina of each eye. The displayed images can be generated with reflected rather than emitted light. While LCD and OLED panels are emissive light, this display can project reflective light directly into the eye and mimicking more natural vision. The resolution and frame rate (minimally 240 frames/sec) can be high. Each eye can be focused independently focus and adjustments can be made to acquire a single image when wearing the device. Head inertial tracking and eye tracking can be incorporated in the head worn device. Two discrete images can be projected directly onto the retinas of the user and the optical elements can be individually adjusted.

To create an image with the VRD a photon source (or three sources in the case of a color display) can also be used to generate a coherent beam of light. The use of a coherent source (such as a laser diode) can allow the system to draw a diffraction-limited spot on the retina. The light beam can be intensity modulated to match the intensity of the image being rendered. The modulation can be accomplished after the beam is generated. If the source has enough modulation bandwidth, as in the case of a laser diode, the source can be modulated directly.

The resulting modulated beam is then scanned to place each image point, or pixel, at the proper position on the retina. Varieties of scan patterns are possible. The scanner could be used in a calligraphic (vector) mode, in which the lines that form the image are drawn directly, or in a raster mode, much like standard computer monitors or television. Use of the raster method of image scanning allows the VRD to be driven by standard video sources. To draw the raster, a horizontal scanner moves the beam to draw a row of pixels. The vertical scanner then moves the beam to the next line where another row of pixels is drawn.

After scanning, the optical beam must be properly projected into the eye. The goal is for the exit pupil of the VRD to be coplanar with the entrance pupil of the eye. The lens and cornea of the eye will then focus the beam on the retina, forming a spot. The position on the retina where the eye focuses the spot is determined by the angle at which light enters the eye. This angle is determined by the scanners and is continually varying in a raster pattern. The brightness of the focused spot is determined by the intensity modulation of the light beam. The intensity modulated moving spot, focused through the eye, draws an image on the retina. The eye's persistence allows the image to appear continuous and stable. Finally, the drive electronics synchronize the scanners and intensity modulator with the incoming video signal in such a manner that a stable image is formed.

Liquid crystal displays (LCDs) currently are often used in display devices for the presentation of information. LCDs with a display resolution of 1080 p HD or greater can provide the image quality that is best for VR or AR systems. An image that is generated electronically is viewed with the optical system of the eye. The image seen is subject not only to the quality of the optical system of the eye, but also to the quality of the display and the environment in which the display is located.

With a VRD, defects in the eye's optical system, such as damaged cornea and lens and reduced retinal sensitivity could be bypassed, as well as the problems of the display environment, such as ambient brightness, angle-of-view and display brightness. Additionally, the seen image could be augmented with other information and brightness of the system does not affect the image formed on the retina. It is believed that VRD based Laser or LED displays are not harmful to the human eye, as they are of a far lower intensity than those that are deemed hazardous to vision, the beam is spread over a greater surface area, and does not rest on a single point for an extended time. Optical damage caused by lasers comes from its tendency to concentrate its power in a very narrow area. This problem is overcome in VRD systems as they are scanned, constantly shifting from point to point with the beams focus. If the laser stops scanning, beam stays focused on one spot can cause permanent damage to the eye. This can be prevented by an emergency safety system to detect the situation and shut it off. Apart from the advantages mentioned before, the VRD system scanning light into only one eye allows images to be laid over one's view of real objects. For example, it could project an animated, X-ray-like image of a car's engine or the human body.

VRD system also can show an image in each eye with an enough angle difference to simulate three-dimensional scenes with high fidelity. VRD can refocus dynamically to simulate near and distant objects with a far superior level of realism. VRD also supports proximity sensing. This means it can provide the illusion of being able to actually be more closely involved with the projected images.

In another embodiment a virtual image projector can also be comprised of a laser configured to form a narrow beam, multiple other optics, and a controller. The multiple optics each have a diffraction grating. One optic can be arranged to receive the narrow laser beam and to project a one-dimensionally dilated beam into the second optic. The second dilation optic can be arranged to receive the one-dimensionally dilated beam and to project a two-dimensionally dilated beam, which the can provide a virtual image. The first and second redirection optics are each operatively coupled to a transducer. The video-display eyewear can resemble eyeglasses and can include a pair of projectors that project virtual display images for view by a wearer. The virtual display images are projected directly in front of the wearer's eyes. The device can include a wearable mount configured to position the projectors a short distance in front of the wearer's eyes. The device can also include controller, which controls the internal componentry of the projectors in order to form the virtual display. Projectors may project virtual display images of infinitely distant objects, where the lens of the human eye adjusts to an infinite or near-infinite focal length to focus on such objects. The projectors may be at least partly transparent, so that the wearer can see external objects as well as the virtual display images or visual elements. The glasses include lenses arranged in front of the projectors and they can be arranged in front of the projectors. The lenses may be configured to correct the focus and/or brightness of the external objects for the comfort and vision needs of the wearer. This arrangement may allow the wearer to shift his or her focus between the external objects, a finite distance away, and virtual display images an infinite distance away.

In an alternative embodiment, the controller can cause projectors to project the same virtual display image concurrently, so that the wearer's right and left eyes receive the same image at the same time. In another embodiment, the projectors may project slightly different images concurrently, so that the wearer perceives a 3 D stereoscopic image.

In another embodiment, eye movement is measured without a camera system and utilizes electrodes placed on the surface of the skin around the eye(s). It is based on the principal where the eye acts like a battery: the cornea is the positive pole and the retina is the negative pole. Electrodes located in specific peri-orbital areas (e.g. around the eye) pick up the corneal-retinal electrical potential variation caused by eye movements, which are then amplified and sent to a recording device. Two (2) or three (3) channel recording devices can be used to record all eye movements. An active electrode is placed next to the external corner of each eye and the third electrode is placed on the frontal midline in such a way that the three recording channels are configured as an isosceles triangle. Three bipolar derivations are set from the active electrodes, thereby making it possible to identify horizontal, vertical and oblique eye movements. Measuring the slow component velocity of nystagmus takes into account the directional influence of responses according to the vector projection of eye movements.

5. Head Tracking

Head tracking on a head-worn unit can be performed by using an inertial measurement unit (also called an IMU or 'tracker'). An IMU is an electronic device that measures one or more DOF (such as position, velocity, orientation, and/or gravitational force, as was described previously in this disclosure) by using one or more sensors. Sensors used in IMUs can include one or more accelerometers, gyroscopes, and magnetometers. A MEMS (micro electro mechanical system) gyroscope, a MEMS accelerometer, and a MEMS magnetometer can be used as complementary and/or redundant sensors to accurately support a full range of motion in a three-dimensional space. Accelerometers work well for measuring five DOF: linear movements in three axes; and absolute tilt about the two axes perpendicular to gravity (i.e. pitch and roll). Accelerometers cannot easily measure rotation about an axis aligned with gravity (i.e. yaw). Magnetometers work well for measuring absolute yaw providing a sixth DOF. Gyroscopes provide a stable way to measure changes the three rotational DOF (pitch, roll, and yaw). Devices that measure these three displacements and measure each of the three rotations in two different ways are typically called nine DOF IMUs. The input signals from the accelerometer(s), magnetometer(s), and gyroscope(s) in these nine DOF IMUs are often processed using a Kalman or a Madgwick filter located in a sensor pre-processing unit to provide output signals that have been optimized for accuracy, stability, and response rate.

The head tracking inertial system can be mounted to the head in numerous configurations. Examples include: at the top of the head with helmets, caps, straps or other head worn covering; in the center of eyeglasses; at the nose piece; in the side of the eyeglasses; in the ear or attached to the ear; and/or attached to the teeth with mouth guards, prosthetic attachments, or fixation with other oral appliances. In other embodiments, the head tracking can be done from sensors in a hand held smart phone, smart pad, or other sensor system attached to a body part. When used in VR and AR platforms, the head tracking technology can normally refresh on-screen images 125-1250 frames per second (or Hz). Higher frame rates reduce movement lag. For specific applications, the refresh rate may be lower than 125 frames per second (fps) or higher than 250 (fps), depending upon the platform used, the application, and type of measurement or testing being performed. For performing some tests, such as the head impulse test a sample rate or refresh rate of 250 Hz is necessary to capture the subtle eye movements, such as the covert saccades. Reducing the lag between head movement and the headset response will mitigate symptoms of motion sickness or visually induced motion sickness. The resolution use can be variable depending on the application or platform used, but may be chosen as 1080×1200 or 2160×1200-2560×1440 or higher and the latency between images should be short (20 ms or less). In further embodiments, the head tracker can be controlled remotely and/or alternatively with eye movements, or voice activation or haptically.

6. Fourier Analysis

A Fourier transform can be used to convert the relationship between an input (such as head motion) and an output (such as eye movement) in the time domain to a relationship in the frequency domain. By doing this, VOP can be measured for natural motion in a non-clinical environment. As described previously, one of the traditional ways of measuring VOR has been to oscillate a subject's head at a fixed frequency and then to measure how quickly the eyes respond. For this kind of testing, a frequency of 0.5 Hertz would correspond to one cycle every 2 seconds. A cycle corresponds to the combination of one movement to the right and one movement to the left. These movements are typically in the form of a sine wave. The gain at this frequency would be the amount of compensation that the eyes make to the movement of the head. A gain of −1 (also often written as a gain of 1) is perfect because the eyes have rotated exactly the same angle as the head, but in the opposite direction. A gain of −0.75 (often written as 0.75) means that the eyes only compensated for 75% of the head rotation. The phase or phase lag describes how much later the eyes moved than the head. A phase or phase lag of 0 would mean the eyes followed exactly. A phase or phase lag of 45 degrees at a frequency of 0.5 Hertz means that the eyes were delayed by $\frac{1}{8}^{th}$ of 2 seconds (or 250 milliseconds) because 45 degrees corresponds to $\frac{1}{8}^{th}$ of a full 360-degree cycle. To determine gain and phase at a variety of frequencies using the traditional approach of oscillating the head in a clinical environment one would repeat the above test at a variety of frequencies and record the results. This method requires control over each input frequency and measuring the gain and phase of the eye response separately for each frequency, which will not work in a non-clinical setting having natural motion.

Any time-varying signal (such as the natural motion of an object in one dimension) can be converted to a series of sine waves. This conversion from a time-varying signal to a series of sine waves is called a Fourier transform. Fourier transforms can be discrete or continuous. A continuous Fourier transform is one in which the time-varying signal is converted to an entire range of frequencies with no gaps between the frequencies. A discrete Fourier transform is one in which the time-varying signal is converted to a specific set of frequencies, such as the series 0.125 Hz, 0.25 Hz, 0.5 Hz, 1.0 Hz, and 2.0 Hz. Discrete Fourier transforms are easier to calculate using digital electronics. By converting the observed natural yaw of the head as a function of time using a Fourier transform, one can generate a graph showing the amplitude of the input signal that the eyes would need to compensate for in order to follow a stationary image or visual element. By converting the sensed horizontal movement of the eyes at this same time using a Fourier transform, one can generate a second graph showing the amplitude of the eye signal that compensates for the head movement. By comparing these two graphs mathematically, it is possible to determine gain at various frequencies directly from the natural head yaw movement. Similar mathematical calculations can be made to determine phase. The same method can be used to determine gain and phase in other dimensions such as pitch of the head versus the sensed vertical movement of the eyes, etc. Discrete Fourier transform calculations of this type can be performed by a microprocessor that receives the time-varying orientation signals from a head orientation sensor and the time-varying signals from an eye orientation sensor using mathematical calculations capable of being understood by anyone skilled in the art.

It should be noted that embodiments of the present invention can be implemented using dynamic analysis tools other than or in addition to Fourier analysis, examples of which can include band pass filters, time domain analysis, Bode plots, Nyquist plots, waterfall diagrams, Campbell diagrams, resonance analysis, power spectral density analysis, frequency response function, coherence analysis, correlation analysis, cross power spectrum analysis, impulse response analysis, octave analysis, order analysis, waveform analysis, and/or any other dynamic system analysis tool capable of being understood by those skilled in the art.

7. Other Potential System Elements

An example of a portable and wearable computing and head mounted display system can include an eye tracking and measuring system, a connected head mounted display tracking and measuring system, an optical system, peripherals, a power supply, a micro-processor, a memory, and a user interface. Components of the system may be configured to work in an interconnected fashion with each other and/or with other components coupled to respective systems. For example, the power supply may provide power to all the components of the system. The processor may receive information from and control the eye tracking system; the head mounted tracking system, the optical system, and peripherals. The processor may be configured to execute program instructions stored in the memory unit and to generate a display of images on the user interface. The display to the user can be presented as a 2D or 3D (3 dimensional) virtual display.

The system may include or be coupled to peripherals, such as a wireless communication interface, a touchpad, an integrated microphone, a high definition (HD) camera, and a speaker. A wireless communication interface may use 3G cellular communications, such as CDMA, EVDO, GSM/GPRS, or 4G cellular communications, such as WiMAX or LTE. Alternatively, wireless communication interface may communicate with a wireless local area network (WLAN), for example, using Wi-Fi. In some examples, wireless communication interface may communicate directly with a device, for example, using an infrared link, Bluetooth, near field communication, or ZigBee. In addition, other wireless interface communication can be used with "off-the-grid" networks (such are FireChat) where there is not cellular phone service or no internet connection.

The power supply may provide power to various components in the system and may include, for example, a rechargeable lithium-ion battery, solar power, mechanical power or various other power supply materials and types known in the art.

The processor may execute instructions stored in a non-transitory computer readable medium, such as the memory, to control functions of the system. Thus, the processor in combination with instructions stored in the memory may function as a controller of the system. For example, the processor may control the wireless communication interface and various other components of the system. In other examples, the processor may include a plurality of computing devices that may serve to control individual components or subsystems of the system. The processor, in conjunction with the memory unit, may perform analysis of the images obtained by the infrared camera.

In addition, the memory unit may store data that may include a set of calibrated wearer eye pupil positions and a collection of past eye pupil positions. Thus, the memory may function as a database of information related to gaze direction. Calibrated wearer eye pupil positions may include, for instance, information regarding extents or range of an eye pupil movement (right/left and upwards/downwards), and relative position of eyes of the wearer with respect to the HMD. For example, a relative position of a center and corners of an HMD screen with respect to a gaze direction or a gaze angle of the eye pupil of the wearer may be stored. Also, locations or coordinates of starting and ending points, or waypoints, of a path of a moving object displayed on the HMD, or of a static path (e.g., semicircle, Z-shape etc.) may be stored on the memory unit.

The system may include the user interface for providing information to the wearer or receiving input from the wearer. The user interface may be associated with displayed images, a touchpad, a keypad, multiple cameras, buttons, a microphone, a haptic device, and/or other peripheral input devices. The processor may control functions of the system based on input received through the user interface. The system and/or testing function controls and input connections can be in a head-worn device and/or in a remote device. The system can be activated or controlled using an electronic keypad, voice, haptic, eyelid movement, ocular orientation, and/or any body movement. The computing system could be a distributed computing system. The computing system could comprise cloud computing.

One or more of the described functions or components of the system may be divided up into additional functional or physical components, or combined into fewer functional or physical components. For example, the infrared camera may be mounted on the wearer separate from the system. Thus, the system may be part of a portable/wearable computing device in the form of separate devices that can be worn on or carried by the wearer. Separate components that make up the wearable computing device may be communicatively coupled in either a wired or a wireless fashion. In some further examples, additional functional and/or physical components may be added.

The system may be configured as, for example, eyeglasses, goggles, a helmet, a hat, a visor, a headband, or in some other form that can be supported on or from a head or parts of the head of the wearer. The system may be further configured to display images or visual elements to both eyes of the wearer. Alternatively, the system may display images or elements to only one eye, either a left eye or a right eye.

If used as part of a head mounted display (HMD), the system may include a gyroscope, a global positioning system (GPS), magnetometer, and an accelerometer. The head mounted display tracking system may be configured to provide information associated with a position and an orientation of the HMD to the processor. The gyroscope may include a micro-electromechanical system (MEMS) gyroscope or a fiber optic gyroscope as examples. The gyroscope may be configured to provide orientation information to the processor. The GPS unit can include a receiver that obtains clock and other signals from GPS satellites. The GPS unit can be configured to provide real-time location information to the processor. The HMD-tracking system may further include an accelerometer configured to provide motion input data to the processor.

8. Additional Embodiments.

In one embodiment, the device or method uses utilizes eyewear with an eye-tracking and measuring sensor, a head motion sensor and compares the gain and phase of each (e.g. an electronic circuit generates a comparison of the three axes from the head orientation sensing element with eye movement signals from the eye sensor to calculate a gain and phase of the eye movement response to head rotation, in the opposite direction). The eye orientation sensor senses vertical movement and horizontal movement of at least one eye. A visual target is provided in the eye worn lens, which can be otherwise transparent, translucent or opaque. The device or method can present this visual target to one eye (monocular) or both eyes (binocular). The device or method is sufficiently comfortable, secure to the head and lightweight to allow the user to have active head movements while wearing the device. Wearing such a mobile or portable, head worn or eye worn device requires a power source. If the power source is in the head worn device of the eye tracker or head tracker it can be rechargeable by a wireless interface.

The device can measure the relationship between motion of the head in this environment and VOP. The data acquired can be uploaded to a remote position from the user for display and interpretation or transmitted wirelessly to a smart phone, wearable display device or other hand held device or other pc computer source. The eye tracker latency delay can be in the range 1 ms-10 ms and can have options to set the latency. The device can be charged with a wireless interface. The head orientation sensor does not use an external pulsed magnetic field and senses pitch and yaw of the person's head in a range of frequencies that comprises at least one frequency greater than 0.01 Hertz and less than 15 Hertz. The head orientation sensor can comprise an IMU. The head orientation sensor can comprise one or more accelerometer(s), magnetometer(s), and/or gyroscopes.

In one embodiment, a single camera system is used for the eye tracking. In another embodiment a multi-camera system is used and the cameras can be located in the lens, framework or eye or head worn device or located remotely. The camera control unit could be activated by touch, head movement, voice, a timer, an external wireless signal, or by placing the device on the head (e.g. putting on the head-worn unit). An eye blink, for a defined time, could also trigger the camera. An algorithm measuring blinking time and duration to discriminate between voluntary and involuntary eye blinks could be used to issue a command to a controller to operate the camera system. The controller could communicate with other parts of the system to support the commands. The camera could have a resolution of at least five megapixels and could be capable of recording at 720 p or 1080 p resolutions. The camera could have a microphone for voice commands, and at least 12 GB of usable storage. The camera could support Bluetooth and/or Wi-Fi. The camera could be part of, or work with an Android or iOS smartphone. The camera could have at least a 25° field of view. The camera system could also comprise an onboard OMAP (Open Multimedia Applications Platform) processor running the Android or iOS operating system. The entire system could be a smartphone that includes an embedded eye camera sensor with a head motion sensor. Providing direct image overlay over the wearer's main line-of-sight, coupled with the motion sensors and camera, it can enable true augmented reality capability. A smartphone or similar device (such as a tablet computer) could also be used to provide wireless remote control.

In one embodiment, the eye-tracker uses the center of the pupil and infrared and/or near-infrared non-collimated light to create corneal reflections (CR). The vector between the pupil center and the corneal reflections can be used to compute the point of regard on surface or the gaze direction.

In an alternative embodiment of a binocular system, two mirror-image optical systems are mounted on each side of the eyeglasses frame. The corneal reflections are generated by illumination with two infrared LED's mounted to the glasses frame. These LED's also serve to illuminate the pupil. The use of infrared (IR) light allows for invisible illumination of the eye. The use of multiple corneal reflections extends the linear range of the system by ensuring that one corneal reflection is always visible on the spherical surface of the cornea even with eccentric gaze. The images of the pupil and corneal reflections are reflected off of an IR mirror positioned in front of the subject's eye and directed to the cameras. This mirror is transparent to visible light and thus does not interfere with normal vision. The video image is sampled by a custom charge-coupled device (CCD) array that allows images to be sampled minimally at 20 Hz. Images from the CCD camera are processed in real time to obtain estimates of the corneal reflection and pupil center locations. Calibration of the eye tracker can be performed using a light source, such as a laser pointer, and calibration procedure looking at multiple objects or points (usually 5).

Another embodiment may use an OLED-based eyewear display which enables the eye tracking of a person with the use of an embedded IR display and camera in the seethrough-lens of a head mounted/eye worn device. This can be worn as a monocular or binocular device with a transparent OLED display inside, which overlays digital information on top of the reflected light that strikes the eye. A bi-directional micro-display can be used in the head worn system for additional gaze triggered augmented-reality (AR) applications. The display contains both an active OLED matrix and integrated photodetectors that can track eye movement activity with front brightness up to 2000 cd/m$^2$.

Another embodiment can use a Liquid Crystal on Silicon (LCoS), field-sequential color, LED illuminated display. The display's LED illumination can be polarized and then shines through the in-coupling polarizing beam splitter (PBS) to the LCoS panel. The panel reflects the light and alters it to S-polarization at active pixel sites. The in-coupling PBS then reflects the S-polarized areas of light through the out-coupling beam splitter to a collimating reflector at the other end. Finally, the out-coupling beam reflects the collimated light into the wearer's eye.

In another embodiment, a low persistence OLED (Organic Light Emitting Diode) 1080 p HD 3D (3 dimensional) virtual display can be utilized for VOP measurement. The OLED display may not be as bright as an LCD display, but it has a major advantage in delivering crisp, rapid movement without any smearing or ghosting of objects. Multiple separate cameras or a single large screen, which is split in half, can be used to provide two view points for each half of the screen. The two views can then be seen separately to either eye to with lenses in the head worn device, to provide a wider field of view. Orientation and movement can be tracked with the stereo 3D (3-dimensional) head tracker with 360 degrees. The user when being tested with the 3D (3-dimensional) virtual display has a sense of being "intimately around the points of visual focal interest". An additional embodiment of using a hand held controller can also be used to sense motion anteriorly and posteriorly, with a 3D (3-dimensional) hand held mobile controller. Testing of the VOR can also be tested with pitch and roll of the head tilt. Predictive tracking (e.g. algorithm which can predict the next head position and orientation can help computing and updating) can be used to prevent latency issues and lessen motion disturbances while being tested. A bone conducting sensor incorporated in the framework can provide auditory/acoustic signals to the user. This data can then be stored, logged, interpreted and uploaded to a remote location.

The eye tracking system can be used with or without a light source. Therefore, another embodiment of eye gaze tracking can be provided with magnetized contact lenses tracked by magnetic sensors mounted on the user's eyewear and/or reflectors or markers on the contact lenses tracked by video-based sensors, also mounted on the user's eyewear. Tracking information of contact lenses from magnetic sensors and video-based sensors may be used to improve eye tracking and/or combined with other sensor data to improve accuracy of eye tracking. Contact lenses may be tracked by one or more mounted head worn cameras and/or magnetic sensors in order to resolve tracking information, such as position of the objects, the distance between the objects and a camera, and the like. Furthermore, reflective contact lenses improve blink detection while eye gaze tracking is otherwise unimpeded by magnetized contact lenses. Additionally, contact lenses may be adapted for viewing 3D (3-dimensional) information. Alternatively, another method could be to place four evenly spaced sensors on the inside of the contact lens, so they cover every angle of the eye movement. The sensors could even be embedded in the lens itself.

In further embodiments, magnetic sensors and video-based sensors may be used in combination to track a magnetized contact lens with one or more reflective patterns, provide blink detection, and eye movement. Other video-based sensors may be used to locate the head position of a user and prune noise from other magnetic or other light sources. Additionally, tracking information from contact lenses of both eyes may be used to improve accuracy.

Magnetized and reflective contact lenses may be utilized to browse menus of computer applications, control virtual characters of video games, select-drag-manipulate objects, and perform other trained or learned actions responsive to a user's eye movement or eye gaze. In further aspects, magnetized and reflective contact lenses can be used in any application that can benefit from eye and/or gaze tracking.

In one embodiment, magnetic sensors may be placed on a video game console or near the head of a user of a video game console to track the location and polarization of magnetized contact lenses. In another embodiment, video-based sensors may be used to track the location of reflective contact lenses transparent to normal light and reflecting one or more portions of the electromagnetic spectrum.

Contact lenses in embodiments can be passive (e.g., utilizing color or polarity for 3D viewing) or active, for example, using a liquid crystal layer that is normally transparent but darkens when a voltage is applied.

One of the advantages of using contact lenses for eye tracking and viewing 3D (3 dimensional) information is that they are more practical (i.e., smaller, light weight and easy to carry around) compared to some peripherals used for eye gaze tracking or for 3D information viewing. For example, glasses typically used for 3D information viewing or head-mounts typically used for eye gaze tracking can be complex and cumbersome.

In addition, contact lenses can offer highly accurate eye tracking information at low cost. For example, when contact lenses are used for eye gaze tracking, the performance can be better than the one that can be achieved with a camera-based eye tracking solution. Also, compared to camera-based solutions which require expensive high-resolution cameras, contact lenses can offer low cost solutions which make them more suitable for consumer products.

Accordingly, in various embodiments, a combination of marker-based and marker-less eye tracking techniques using contact lenses provide interacting with or controlling objects or menus of a video game, a projected visual user interface, an augmented virtual reality user interface, or the like.

In another embodiment contact lenses with embedded electronics inside such as LEDs, LCDs. or new nano-electronic materials can also be used for eye tracking. Applications of electronic contact lenses may be even more promising.

Trackers can constantly ping the sensors in the IMU to get information from them. The rate at which this happens is expressed as [samples] Hz (per second). The wearer of a head tracker may perform a gesture to indicate an attempt to unlock the head mounted camera display. For example, a gyroscope coupled to the head mounted display may detect a head tilt, for example, and indicate that the wearer may be attempting to unlock the head mounted display screen.

In one embodiment the head tracker comprises an IMU, an RGB (Red Green Blue) LED, an 800-925 nm infrared LED, a battery and wireless interface charger, a wireless interfaced micro-controller, and a transceiver. The gyroscope in the IMU can be capable of sampling rates up to 760 Hz, and the transmitter link can have the throughput to transmit that fully under 1 ms latency to the remote station.

Full positional updates (fused information from all the sensors) from the IMU can be sent at a rate of at least 500 Hz. The IMU comprises sensors that can sense roll, pitch, and yaw, as well as inertia when the IMU is moved forward/back, left/right, and up/down. The IMU could be a nine DOF IMU.

Another embodiment can use eyewear that has elements within the transparent, opaque or semi-transparent lens comprised of: calibration points, light source and video camera for recording any eye movement. In this embodiment, no mirrors are utilized. The framework provides the power source, data logging capacity, software for measurement and can include: alarm signal for movement of the head, sensors to transmit collected data to remote source and data interpretation. This can be done with passive head movements or active head movements and an alarm in the device can trigger the timing event of head movement, rather than having another person move the user's head for more of an "active head movement test". Specifically, the electronic circuit can be triggered or turned on by verbal command (auditory input), by visual means (such as prolonged eyelid closure or other specific eyelid movement), mechanically (such as by the attachment of the head worn device to the head), with timer software programming, and remotely. Additionally, this worn device can provide software to detect a value or abnormality for eye response or eye reflex, where eye response (or reflex) might be VOR, DVA, DVS, or RIS. This eye response (or reflex) output could be reported as a binary (normal or abnormal) value or it could be reported as a score on a continuous scale, such as the way in which other physiologic parameters (such as height, weight, blood pressure, temperature, and many more parameters) are reported. If a score is reported, it could be a score for a single parameter at a single frequency, such as gain or phase at 0.5 Hertz, or it could be a multi-frequency composite score (such as gain or phase or a combination of gain and phase at a range of frequencies from 0.1 Hertz to 1 Hertz). The score could be for one eye or both eyes. The score could include measurement of asymmetry. An eye response (or reflex) score on a continuous scale or on a continuous composite scale (or a simple reporting of abnormalities), could benefit from a rehabilitative VOR eye-tracking program. This can then enable the person to develop normal VOP again or enhanced eye fixation and specifically RIS on a target of interest with head rotation or head movement, or improve other ocular response or reflex capabilities while performing occupational activities.

If the device does not need to be completely portable and self-contained, one can perform inertial head position and/or orientation tracking by transmitting external signals such as pulsed magnetic fields, optical signals, or audio signals to a transducer located on the head-mounted (eye-tracker) system. The transducer can be mounted on the eyewear/head for azimuth rotation. For example, a fixed transmitting device can radiate a pulsed magnetic field into which the head mounted receiver is immersed. The field is sensed by the receiver and processed by a microprocessor to provide three-dimensional position information as well as head elevation, azimuth and roll angles. The head tracker provides absolute angular and translational position measurements and does not require calibration for each person. The head tracker can operate with multiple receivers allowing for measurement of other important parameters such as hand position in hand-eye coordination studies. Other embodiments that use external signals can include the use of external infrared and ultrasonic signals to detect the position and orientation of the head or other part of the human anatomy.

The mounted head tracker sensor in the head worn/eye worn device can include an IMU of any type cable of being understood by anyone skilled in the art. The mounting of the head tracker can be in the center of the head worn device, or in the nosepiece with eyeglass device or on the sides of the eyeglasses. The head tracker can also be mounted to a removable in-the-mouth appliance, which is fixed to the tooth. It can also be incorporated into a mouth guard or retainer device. The mouth worn device can also generate a sound signal to produce imperceptible sound vibrations that are conducted via the teeth, through bone, to the cochlea and providing the user with signals to move the head.

Another alternative embodiment of the invention is an inertial angular orientation tracking apparatus mounted to the head worn device. Drift sensitive sensors, such as angular rate sensors, produce a signal that is integrated to give a signal that represents angular position. The angular position signal may drift, due to integration of a bias or noise in the output of the rate sensors. To correct this drift, compensating sensors, such as gravimetric tilt sensors and geomagnetic heading sensor(s) can periodically measure the angular position, and this directly measured position signal is used to correct the drift of the integrated position signal. The direct angular position sensors cannot be used alone for dynamic applications because the gravitational sensors are also affected by non-gravitational accelerations, and therefore only accurately reflect angular position when under the influence of no non-gravitational accelerations. Typically, the drift sensitive sensors are angular rate sensors, (these include: rate gyroscopes and vibrating piezoelectric, magneto-hydrodynamic, optical and micro-machined silicon devices) the outputs from which are integrated once. However, other suitable drift sensitive sensors include linear accelerometers used to sense angular rate, gyroscopic angular position sensors and angular accelerometers. Typically, the compensating sensors are inclinometers, accelerometers and compasses.

In another embodiment a head orientation and/or inertial tracking device can be used that is essentially "source-less", in that it can be used anywhere with no set-up of a source, yet it enables a wider range of virtual environment-style navigation and interaction techniques than does a simple head-orientation tracker, including manual interaction with virtual objects. This device can feature a source-less orientation tracker including an inertial sensor, a tilt-sensor, or a magnetic compass sensor.

In another embodiment, the device can include a position tracker such as an acoustic position tracker, a system that tracks LEDs, optical sensors or reflective marks, a video machine-vision device, a magnetic tracker with a hand-held magnetic source and sensors integrated in the headset or vice versa, or a radio frequency position locating device.

In an alternative embodiment, the present invention not only measures VOP (as the VOR or RIS with head movement), but also rehabilitates/retrains the user when an abnormality is present, to enhance the VOR and RIS or retinal visual accuracy with specific visual stimulation and head movements. This rehabilitation can be done for specific vestibulo-ocular pathologic findings. Specifically, when there is an abnormal VOR in the horizontal plane, specific algorithms of eye fixation on a target object, while the head is moving horizontally can be used to rehabilitate the abnormality. When the abnormal VOR is seen in the vertical plane, specific algorithms of eye fixation on a target object, while the head is moving in a vertical manner can be used to rehabilitate the abnormality. As the VOR is enhanced or improved, the DVA or RIS will be enhanced.

In one embodiment, the device or method could provide a sound signal and/or visual signal to alert or trigger the user to respond by moving the eye or head. Remote sensing, see through capability with the head/eye worn device, and the rendering of a visible target in broad daylight are all features that can be incorporated in embodiments of the present technology. The head/eye worn device or method could also collect the data, which could then be uploaded to a medical doctor, trainer, coach or other person at a remote location. This remote location could then provide verbal or visual feedback to the user and this feedback could be integrated with other information provided to the user.

In one embodiment the device or method disclosed here can also be used to help a person improve his or her VOR and DVS and accuracy used during activities in daily living, routine exercise, and high level athletic/vocational activities. This can be used to help a person improve his or her balance by challenging, exercising, enhancing, and/or retraining the VOR (fixation/re-fixation) used during activities in daily living, routine exercise, and high level athletic/vocational activities and therefore improving the retinal visual stability and accuracy of the fovea to remain fixed on the visual element. Thus, embodiments of the present invention can incorporate head movements in one or a number of planes as part of a systematic program for enhancing the VOR and DVA. Using the devices and methods described here it is possible for rehabilitation programs to incorporate head movement with stable image identification and image identification movement with the head remaining stable. The data obtained from the devices and methods described here can be used for wireless communications. The data can be embedded GIS or geographic information system of the eyes or a digital map of where the eyes are located relative to the head movement.

In an embodiment of the present invention, the main functions (head orientation sensing, eye tracking, and the display of an image or images can be performed by a general purpose portable, battery operated, hand held device, such as a smartphone, computer pad, or other wearable computer device. For example, vestibulo-ocular performance could be measured in a virtual environment that was created by attaching a smartphone to a person's head, using the smartphone screen to display stereoscopic images, using the orientation sensors in the smartphone as a head tracker, and using the user-facing video camera to view and track the user's eyes. If the light from the display is insufficient, additional light could be provided by another source that could be operated using infrared (IR) or visible light. Eye tracking could also be enhanced by having the subject wear a contact lens or lenses that have markers on them that would be visible to the smartphone camera. Examples of configurations that could be adapted in this way include Google Cardboard and the Samsung Gear VR. Data on the smartphone could be stored, logged, interpreted, displayed, and/or transmitted to other devices. Transmission of data could use any of the communications technologies available on a typical smartphone including, but not limited to Bluetooth, WiFi, a cellphone signal, or a wired signal. The smartphone based system could also use auditory signals for instructions, audio cues during the test, and/or alarms. This system could be used for passive head movement testing or active head movement testing. Additionally, this portable hand held device or limb worn device can provide a software rehabilitative eye tracking program, if an abnormality is present. This can then enable the person to develop normal or enhanced eye or foveal fixation stability on a target of interest with head rotation or head movement, while performing their occupational activities. Additionally, fiduciary markers can be applied on the head to facilitate inertial head tracking.

It would also be possible for the smartphone to be handheld instead of head-mounted and provide the head orientation sensing, eye tracking, and display functions. Data on the smartphone could also be stored, logged, interpreted, displayed, and/or transmitted to other devices. Transmission of data could use any of the communications technologies available on a typical smartphone including, but not limited to Bluetooth, WiFi, a cellphone signal, or a wired signal. The smartphone-based system could also use auditory signals for instructions, audio cues during the test, and/or alarms. This system could be used for passive head movement testing or active head movement testing.

In one embodiment, the device can be calibrated before it is used. When used in the laboratory setting, calibration can be performed by focusing on a distant target, such as a light bar or laser light which is projected to the wall. The image or visual element moves horizontally, vertically and then is center located. Typically, several trials are performed to establish reproducible results. During this test, the person is instructed to rotate the head from side to side horizontally or vertically to an auditory cue at frequencies ranging from 2 to 6 Hz. Eye movements are recorded including: direction, amplitude, and velocity of eye movements. Head inertial movements are recorded by the velocity rate sensor attached to the head. Tracking eye movement from spot to spot in this way is called "active tracking". When used in a non-laboratory or a non-clinical setting, similar testing can be performed if there are objects available to serve the same purpose as the distant target in the laboratory setting. Testing of this type allows gain, phase, and asymmetry to be measured separately at each frequency. A more sophisticated approach would be to ask the subject to follow an object that is not necessarily moving at one specific frequency, but at a combination of frequencies and then using a Fourier transform to convolve the gain, phase, and asymmetry at various frequencies directly from the complex waveform that was being followed by the subject.

As described in the previous paragraph, in some embodiments of the present invention, the head movement tracked and measured can be active. Another approach is to use and measure natural movement that normally occurs during normal activities or activities associated with a person's work and to compare that to the eye movement that occurs at the same time using a Fourier transform. This approach can be called "natural tracking" A third approach is to attach the head to something that then forces the head to move in a specific pattern—which is called "passive tracking."

In embodiments of the present invention, head movement testing can sense horizontal, vertical or torsional movements at various linear velocities, angular velocities, linear accelerations, angular accelerations, or frequencies. Natural test method testing in the horizontal plane could utilize focusing on a target moving across the horizontal visual field. Watching a moving object ascend and descend in the air can serve as a natural vertical test.

Any combination of the discussed embodiments of head inertial trackers and eye tracking systems can be used to measure the ocular response (e.g. VOR) with head movement. If active tracking is used, the user visualizes a target of interest while moving the head. The target the user is focused on can be seen through a see-through lens (e.g. such as looking at a dot on a wall projected in front of them) or, if wearing other semi-transparent or non-transparent head worn applications (such as a pair of goggles), the target may be displayed as a 3D image, hologram or some other light source image. Video camera eye orientation tracking, using invisible or visible light, simultaneously can be used with head tracking. As the head moves, the ocular responses can be tracked and measured by a variety of modalities. A Fourier transform can be used to compares the inertial head movement and eye movement response at various frequencies in a complex waveform and software can analyze the data. The stored data can be displayed remotely and abnormalities of the related ocular response to the head movement can then predict the performance of the user when performing an occupational activity.

In the prior art, clinicians have looked at the VOR response and made a binary judgment (e.g. the VOR was abnormal or normal). This normal/abnormal criterion would then be used to determine whether vestibular rehabilitation was needed. A better method for evaluating the VOR response would be to measure vestibulo-ocular performance on a continuous scale, just like we measure the speed of an athlete. By doing this, one can get a subject's human performance measurement. Specifically, there can be a VOR response score that more clearly establishes the vestibulo-ocular response measurement and expresses this response measurement in language that can more appropriately be applied to human performance measurement and improvement. Establishing such a scoring system will enable people to more accurately predict human performance with specific activities. It may also help in the development of activities that improve the human performance in fields where above average VOP is of benefit. The same use of scoring on a continuous scale and multi-frequency composite scoring can apply to DVA, DVS and RIS.

9. Areas of Application

Embodiments of the systems and methods described herein could be used in a variety of areas, including but not limited to the military, sports, medical, and commercial businesses. Visual acuity tests may be performed using this system in many different ways. It can be a quick way to detect vision problems in schools or for other mass screening (e.g. military recruits, sport applications and other occupations). Within the meaning of this application, any ophthalmic eye-testing device that supplies a predetermined visual stimulus to the person in a predetermined location (which may move) is an automated ophthalmic eye-testing device. In the tests described herein, all oculomotor responses can be measured in a VR/AR/synthetic 3D system. Eye, eyelid, and head movement can be tracked. Eye movement, eye position, visual acuity, pupil function, peripheral and central vision testing can all be easily performed with this technology in these platform systems. These eye activities can be correlated with movement of the extremities to assess hand eye coordination.

Sports. Embodiments of the present invention can be used in sports/athletic environments where ocular parameter measurement can help predict performance and early detection of abnormalities such as concussions and traumatic brain injury. For example, if a player has an abnormal VOR/DVA in the horizontal plane, that person may not be able to catch a ball when competing in athletic activities that require the head to rotate in a horizontal plane. Similarly, if a player has a vertical VOR/DVA abnormality and is running downfield while looking upwards over the shoulder, the ball will not be in focus. Specifically, the retinal visual stability and accuracy would be diminished. In this instance, there would be a higher likelihood of dropping the ball compared to another athlete who has normal VOR responses with normal DVA. If a VOR abnormality was determined to be present prior to play, which could result in difficulty with foveal fixation, and athlete could undergo VOR retraining to rectify the abnormality and therefore improve play performance. Alternatively, the coaching staff could select another athlete who did not have this abnormality. For example, on game day if a football player had an abnormal VOR, with resultant decline in the DVA, in the vertical plane (e.g. lack of visual fixation on an object of interest with upwards and downwards movement of the head), then it can be predicted that the athlete is predictable not likely to catch a ball while running downfield and looking upwards over the shoulder (e.g. you cannot catch, what you cannot accurately see). This would offer some value to the coaching staff in selecting plays for the player or players for the necessary play to be performed. Additionally, if an athlete had such an abnormality and could be given some rehabilitation methods prior to play, this could correct the abnormality and increase performance in that activity. Athletes who have had concussions or TBI can have a VOP abnormality, with resultant decrements in the VOR, DVA, or RIS. Embodiments of the present invention can be an accurate method to determine when the athlete is ready to return to play activities, based on improvement of the VOR or DVA. It therefore can be utilized in TBI/concussion evaluation/assessment and management for return to play. It is also intended for athletes who wish to enhance their training and athletic/vocational performance. It can be used in fitness centers, sports training centers, athletic performance centers, and vocational performance centers.

Military personnel functioning in a high-level environment and requiring target fixation of their eyes, while performing other activities such as with head or body movement, require a normal VOR and normal DVA. If the VOR/DVA is abnormal, the individual will not demonstrate peak human performance. Embodiments of the present invention can be used by the military in places such as the pilot selection process or special operations community to aid in the selection of individuals without a VOR/DVA abnormality. VOP measurement could enable other individuals, who had normal foveal fixation ability to be chosen for a particular task that has better predictable performance for a particular duty of the day.

Medical. Similarly, any person with a motion sensitivity disorder (such as motion sickness, vection induced motion sickness, or visually induced motion sickness) or a balance problem, either of a central or peripheral origin, will have a VOR/DVA abnormality. Individuals with such an abnormality will express symptoms of dizziness, disorientation, difficulty with focusing, nausea, fuzziness, and such other complaints as not being clear headed. Embodiments of the present invention can be useful to people who have experienced a vestibular insult, vestibular dysfunction or labyrinthine dysfunction such as those caused by infection, concussive injury, traumatic brain injury, vascular disease, ototoxic or vestibulotoxic medication use, surgical complications, Meniere's disease, people experiencing chronic imbalance, such as, but not limited to, stroke victims, people with systemic illnesses, the elderly and other people who have experienced head injuries, especially those who have experienced cerebral or labyrinthine (inner ear) concussions. It can be used in physician offices to see if a gaze stabilization problem exists and can be useful in the treatment of such an abnormality when it is present. It also can be utilized other centers which perform vestibular rehabilitation and athletic/vocational enhancement environments. This VR/AR system or method described herein can be used as an objective tool for assisting in the diagnosis of traumatic brain injury (TBI), concussion and other degenerative cerebellar disorders that cause highly saccadic results.

Commercial. Embodiments can also be used in other industries where individuals are expected to perform in high activity levels, or provocative environments.

Vestibular Rehabilitation. VOR scoring can also be beneficial in determining who is likely to benefit with vestibular rehabilitation therapy. VOR scoring can also be used more objectively in determining the benefit or improvement with such therapy. The system can include improvement information that can be used by the user, a coach, a medical practitioner, or any other advisor to help interpret the scoring and provide advice and/or exercises to improve ocular reflex. Although vestibular rehabilitation therapy can improve the ocular responses, this scoring can accurately quantify the improvement and more ably predict who is able to return to their normal activity without loss of human performance. Having a VOP score can also provide feedback that helps to control abnormal VOR responses. When an ocular response is abnormal with head rotation (a VOR abnormality, for example), such a finding can also determine a need for improvement with rehabilitation. Repetitive head movement in the abnormal plane of rotation, while the eye remains fixed on a target of interest, can provide a means for improving or enhancing the VOR or other eye responses. Specifically, if a VOR abnormality is found to exist in the horizontal plane, VOR enhancement rehabilitation therapy is given in the same plane. In this instance, the user focuses on a target of interest and the user rotates the head horizontally, while continuing to look at the target. If a VOR abnormality is found to exist in the vertical plane, VOR enhancement rehabilitation therapy is also given in the similar plane of the abnormality. In this instance, the user focuses on a target of interest and the user rotates the head vertically, while continuing to look at the target. The head speed can be varied and the target, which the user is focused, can be changed. The process can be repeated as often as necessary until the VOR abnormality is corrected. This therapy can be performed in any plane where such an abnormality exists. The same use of scoring on a continuous scale and multi-frequency composite scoring can apply to DVA, DVS and RIS.

The present invention permits supernormal enhancement of these same systems where no balance disorder exists, as in the case for enhancement of athletic and vocational abilities. Such an enhancement methodology can be used in athletic/vocational enhancement or training and other training environments such as virtual reality training and the like.

While the disclosure has been described with respect to a limited number of embodiments and areas of use, those skilled in the art, having benefit of this disclosure, will appreciate that other embodiments may be devised which do not depart from the scope of the disclosure as disclosed herein. The disclosure has been described in detail, it should be understood that various changes, substitutions and alterations can be made hereto without departing from the spirit and scope of the disclosure.

What is claimed is:

1. A human ocular performance measuring device wherein:
   the device is configured for measuring an ocular performance characteristic selected from the group of:
   saccades;
   pursuit tracking during visual pursuit;
   nystagmus;
   vergence;
   eyelid closure; and
   focused position of the eyes; and
   the device comprises:
   an eye sensor wherein:
     the eye sensor comprises a video camera; and
     the eye sensor senses eye movement information selected from the group of:
     horizontal eye movement;
     vertical eye movement; and
     eyelid movement;
   a head orientation sensor wherein:
     the head orientation sensor senses a head movement selected from the group of pitch and yaw of a person's head wherein pitch represents a rotation about a first axis representing up and down movement of the person's face when the rear of the person's head moves in the opposite direction and yaw represents horizontal movement of the face when looked at from the front about a second axis substantially aligned with the spine and perpendicular to the first axis; and
     the head orientation sensor senses the head movement in a range of frequencies between 0.01 Hertz and 15 Hertz;
     the head orientation sensor comprises a micro-electro-mechanical system integrated circuit comprising a module selected from the group consisting of an accelerometer, a magnetometer, and a gyroscope;
   an electronic circuit wherein:
     the electronic circuit comprises a central processing unit, and a memory unit;
     the electronic circuit is responsive to the eye movement information received from the eye sensor;
     the electronic circuit is responsive to head movement information received from the head orientation sensor; and
     the electronic circuit uses a Fourier transform to generate a gain signal and a phase signal in response to the eye movement information and the head movement information; and
   a display wherein the display is configured for presenting information selected from the group of:
     virtual reality information;
     augmented reality information; and
     synthetic computer-generated 3-dimensional information.

2. The device of claim 1 wherein:
the device measures saccades.

3. The device of claim 1 wherein:
the device measures pursuit tracking during visual pursuit.

4. The device of claim 1 wherein:
the device measures nystagmus.

5. The device of claim 1 wherein:
the device measures vergence.

6. The device of claim 1 wherein:
the device measures eyelid closure.

7. The device of claim 1 wherein:
the device measures focused position of the eyes.

8. The device of claim 1 wherein:
the device further measures vestibular ocular reflex.

9. The device of claim 1 wherein:
the device is a head-worn device.

10. The device of claim 1 wherein:
the eye sensor senses eye movement information selected from the group of horizontal eye movement and vertical eye movement.

11. The device of claim 1 wherein:
the head orientation sensor senses pitch of the person's head and yaw of the person's head
the eye sensor senses eye horizontal eye movement and vertical eye movement;
the electronic circuit uses a Fourier transform to generate a vertical gain signal and a vertical phase signal in response to the vertical eye movement information and the pitch information; and
the electronic circuit uses a Fourier transform to generate a horizontal gain signal and a horizontal phase signal in response to the horizontal eye movement information and the yaw information.

12. The device of claim 1 wherein:
the eye sensor senses rotational movement of at least one eye where the rotational movement is a rotation of the eye when looking at the eye from the front.

13. The device of claim 1 wherein:
the device further measures visual acuity.

14. The device of claim 1 wherein:
the eye sensor further senses the position of at least one eye;
the device further comprises a forward-facing camera; and
the forward-facing camera is responsive to the eye sensor.

15. The device of claim 1 wherein:
the device further measures eye orientation.

16. A human ocular performance measuring system wherein:
the system is configured for measuring an ocular performance characteristic selected from the group of:
saccades;
pursuit tracking during visual pursuit;
nystagmus;
vergence;
eyelid closure; and
focused position of the eyes; and
the system comprises:
an eye sensor wherein:
the eye sensor comprises a video camera; and
the eye sensor senses eye movement information selected from the group of:
horizontal eye movement;
vertical eye movement; and
eyelid movement;
a head orientation sensor wherein:
the head orientation sensor senses a head movement selected from the group of pitch and yaw of a person's head wherein pitch represents a rotation about a first axis representing up and down movement of the person's face when the rear of the person's head moves in the opposite direction and yaw represents horizontal movement of the face when looked at from the front about a second axis substantially aligned with the spine and perpendicular to the first axis; and
the head orientation sensor senses the head movement in a range of frequencies between 0.01 Hertz and 15 Hertz;
an electronic circuit wherein:
the electronic circuit comprises a central processing unit, and a memory unit;
the electronic circuit is responsive to the eye movement information received from the eye sensor;
the electronic circuit is responsive to head movement information received from the head orientation sensor; and
the electronic circuit uses a Fourier transform to generate a gain signal and a phase signal in response to the eye movement information and the head movement information; and
a display wherein the display is configured for presenting information selected from the group of:
virtual reality information;
augmented reality information; and
synthetic computer-generated 3-dimensional information.

17. The system of claim 16 wherein:
the system comprises a head-worn device; and
the head orientation sensor comprises a head-worn micro-electro-mechanical system integrated circuit comprising a module selected from the group consisting of an accelerometer, a magnetometer, and a gyroscope.

18. The system of claim 16 wherein:
the head orientation sensor comprises a video camera;
the display is selected from the group of:
a volumetric display;
a hologram; and
a lenticular display.

19. The system of claim 16 wherein:
the head orientation sensor comprises the same video camera as the eye sensor.

20. A method for measuring human ocular performance comprising the steps of:
establishing a device that comprises:
an eye sensor comprising a video camera configured for sensing eye movement information selected from the group of:
horizontal eye movement;
vertical eye movement; and
eyelid movement;
a head orientation sensor configured for sending a head movement selected from the group of pitch and yaw of a person's head wherein pitch represents a rotation about a first axis representing up and down movement of the person's face when the rear of the person's head moves in the opposite direction and yaw represents horizontal movement of the face when looked at from the front about a second axis substantially aligned with the spine and perpendicular to the first axis; and
the head orientation sensor senses the head movement in a range of frequencies between 0.01 Hertz and 15 Hertz;
the head orientation sensor comprises a micro-electro-mechanical system integrated circuit comprising a module selected from the group consisting of an accelerometer, a magnetometer, and a gyroscope;
an electronic circuit; and
a display wherein the display is configured for presenting information selected from the group of:
virtual reality information;
augmented reality information; and
synthetic computer-generated 3-dimensional information.
using the electronic circuit to:
receive eye movement information from the eye sensor;

receive head movement information from the head orientation sensor; and generate a gain signal and a phase signal using a Fourier transform, the eye movement information, and the head movement information; and measure an ocular performance characteristic selected from the group of:
  saccades; pursuit tracking during visual pursuit; nystagmus; vergence; eyelid closure; and focused position of the eyes.

* * * * *